US012799167B2

(12) United States Patent
Cui et al.

(10) Patent No.: US 12,799,167 B2

(45) Date of Patent: Nov. 17, 2026

(54) VACCINE COMPOSITIONS OF HERPESVIRUS ENVELOPE PROTEIN COMBINATIONS TO INDUCE IMMUNE RESPONSE

(71) Applicant: THE HENRY M. JACKSON FOUNDATION FOR THE ADVANCEMENT OF MILITARY MEDICINE, INC., Bethesda, MD (US)

(72) Inventors: Xinle Cui, Gaithersburg, MD (US); Clifford M. Snapper, Potomac, MD (US)

(73) Assignee: THE HENRY M. JACKSON FOUNDATION FOR THE ADVANCEMENT OF MILITARY MEDICINE, INC., Bethesda, MD (US)

(*) Notice: Subject to any disclaimer, the term of this patent is extended or adjusted under 35 U.S.C. 154(b) by 0 days.

(21) Appl. No.: 18/494,219

(22) Filed: Oct. 25, 2023

(65) Prior Publication Data

US 2024/0270796 A1 Aug. 15, 2024

Related U.S. Application Data

(63) Continuation of application No. 17/165,310, filed on Feb. 2, 2021, now abandoned, which is a continuation of application No. 16/480,098, filed as application No. PCT/US2018/015459 on Jan. 26, 2018, now Pat. No. 11,572,389.

(60) Provisional application No. 62/451,396, filed on Jan. 27, 2017.

(51) Int. Cl.

| | |
|---|---|
| ***C07K 14/005*** | (2006.01) |
| ***A61K 39/245*** | (2006.01) |
| ***A61P 31/22*** | (2006.01) |
| ***C12N 7/00*** | (2006.01) |

(52) U.S. Cl.

CPC .......... *C07K 14/005* (2013.01); *A61K 39/245* (2013.01); *A61P 31/22* (2018.01); *C12N 7/00* (2013.01); *C12N 2710/16034* (2013.01); *C12N 2710/16071* (2013.01); *C12N 2710/16111* (2013.01); *C12N 2710/16123* (2013.01); *C12N 2710/16134* (2013.01); *C12N 2710/16171* (2013.01); *C12N 2710/16234* (2013.01); *C12N 2710/16271* (2013.01); *C12N 2710/16334* (2013.01); *C12N 2710/16371* (2013.01); *C12N 2710/16634* (2013.01); *C12N 2710/16671* (2013.01); *C12N 2710/16734* (2013.01); *C12N 2710/16771* (2013.01)

(58) Field of Classification Search

CPC ............ C12N 7/00; C12N 2760/16134; C12N 2710/16634; C12N 15/869; C12N 2710/16034; C12N 2710/16134; C12N 2710/16671; C12N 2700/00; C07K 14/005; C07K 14/035; C07K 14/045; C07K 16/088; A61K 39/245; A61K 39/12; A61K 35/763; A61K 38/162; A61K 49/14

See application file for complete search history.

(56) References Cited

U.S. PATENT DOCUMENTS

| | | | | |
|---|---|---|---|---|
| 4,617,379 A | 10/1986 | Dobkin et al. | | |
| 6,190,860 B1 * | 2/2001 | Spaete | C12Q 1/705 | 435/5 |
| 2008/0187545 A1 * | 8/2008 | Shenk | A61P 31/22 | 435/7.1 |
| 2009/0270268 A1 | 10/2009 | Funaro et al. | | |
| 2013/0171234 A1 | 7/2013 | Fairman et al. | | |
| 2014/0023673 A1 | 1/2014 | Weiner et al. | | |
| 2014/0030292 A1 | 1/2014 | Franti et al. | | |
| 2014/0127247 A1 | 5/2014 | Dubensky, Jr. et al. | | |
| 2014/0370026 A1 | 12/2014 | Shenk et al. | | |
| 2015/0093413 A1 | 4/2015 | Thess et al. | | |
| 2015/0174237 A1 * | 6/2015 | Mond | A61P 31/04 | 536/23.4 |

(Continued)

FOREIGN PATENT DOCUMENTS

| | | |
|---|---|---|
| WO | 2014/018858 A2 | 1/2014 |
| WO | 2015054639 A1 | 4/2015 |

(Continued)

OTHER PUBLICATIONS

Britt WJ, Jarvis MA, Drummond DD, Mach M. Antigenic domain 1 is required for oligomerization of human cytomegalovirus glycoprotein B. J Virol. Apr. 2005;79(7):4066-79. (Year: 2005).*

(Continued)

*Primary Examiner* — Rachel B Gill

(74) *Attorney, Agent, or Firm* — MH2 Technology Law Group, LLP

(57) ABSTRACT

Antigenic compositions and uses thereof can include at least two human herpesvirus (HHV) polypeptides involved in mediating HHV binding, fusion, and entry into host cells, such as gp350, gH, gL, and gB, or nucleic acids encoding the polypeptides. The two HHV polypeptides can be any combination of: a gB polypeptide; a gp350 polypeptide; a gL polypeptide; and a gH polypeptide, and optionally any one or more of the following polypeptides: gp42, gM, gN, gl, gC, gE, gD, ORF68, BMRF-2, BDLF2, UL128, UL130, UL131A, and gpK8.1. Methods of inducing an immune response or treating or preventing an HHV infection in a subject can administer to the subject at least two of the HHV polypeptides or nucleic acid(s) encoding the same. Methods can passively transfer immunity using high-titer anti-HHV antibodies or immune cells.

18 Claims, 19 Drawing Sheets

Specification includes a Sequence Listing.

(56) References Cited

U.S. PATENT DOCUMENTS

2015/0359879 A1* 12/2015 Wellnitz .............. C07K 14/005 435/367
2016/0159864 A1* 6/2016 Carfi ...................... A61P 31/22 435/325
2016/0296619 A1* 10/2016 Orlinger ................ A61P 31/22
2016/0303225 A1 10/2016 Cui et al.
2018/0311343 A1 11/2018 Huang et al.
2020/0163878 A1 5/2020 Baumhof et al.

FOREIGN PATENT DOCUMENTS

WO WO-2015089340 A1 * 6/2015 .............. A61P 43/00
WO WO-2016092460 A2 * 6/2016 ............. A61K 39/12
WO WO-2017192434 A1 * 11/2017 .............. A61P 37/04
WO 2019/055887 A1 3/2019

OTHER PUBLICATIONS

Leng SX, Kamil J, Purdy JG, Lemmermann NA, Reddehase MJ, Goodrum FD. Recent advances in CMV tropism, latency, and diagnosis during aging. Geroscience. Jun. 2017;39(3):251-259. Epub Jul. 5, 2017. (Year: 2017).*
Kabanova A, Perez L, Lilleri D, Marcandalli J, Agatic G, Becattini S, et. al. Antibody-driven design of a human cytomegalovirus gHgLpUL128L subunit vaccine that selectively elicits potent neutralizing antibodies. Proc Natl Acad Sci U S A. Dec. 16, 2014;111(50):17965-70. Epub Dec. 1, 2014. (Year: 2014).*
McVoy MA, Lee R, Saccoccio FM, Hartikka J, Smith LR, Mahajan R, Wang JB, Cui X, Adler SP. A cytomegalovirus DNA vaccine induces antibodies that block viral entry into fibroblasts and epithelial cells. Vaccine. Dec. 16, 2015;33(51):7328-7336. Epub Oct. 24, 2015. (Year: 2015).*
Chiuppesi F, Nguyen J, Park S, Contreras H, Kha M, Meng Z, Kaltcheva T, Iniguez A, et al. Multiantigenic Modified Vaccinia Virus Ankara Vaccine Vectors To Elicit Potent Humoral and Cellular Immune Reponses against Human Cytomegalovirus in Mice. J Virol. Sep. 12, 2018;92(19):e01012-18. (Year: 2018).*
Office Action dated Aug. 17, 2021 for corresponding Japanese Patent Application No. J019-540440, 6 pages with English translation.
McVoy et al., "A cytomegalovirus DNA vaccine induces antibodies that block viral entry into fibroblasts and epithelial cells", Vaccine, 2015, vol. 33, pp. 7328-7336.
Perez et al., "Novel Epstein-Barr virus-like particles incorporating gH/gl-EBNA1 or GB-LMP2 induce high neutralizing antibody titers and EBV-specific T-cell responses in immunized mice", Oncotarget, 2017, vol. 8, No. 12, pp. 19255-19273.
International Search Report and Written Opinion dated Apr. 13, 2018 from International Application No. PCT/US2018/015459 (Authorized Officer, Blaine R. Copenheaver), 21 Pages.
Fouts et al., "Antibodies against the gH/gL/UL128/UL130/UL131 Complex Comprise the Majority of the Anti- Cytomegalovirus (Anti-CMV) Neutralizing Antibody Response in CMV Hyperimmune Globulin", Journal of Virology, Jul. 2012, vol. 86, No. 13, pp. 7444-7447.
Wille et al., "A Human Cytomegalovirus gO-Null Mutant Fails to Incorporate gH/gL into the Virion Envelope and is Unable to Enter Fibroblasts and Epithelial and Endothelial Cells", Journal of Virology, Mar. 2010, vol. 84, No. 5, pp. 2585-2596.
Wussow et al., "A Vaccine Based on the Rhesus Cytomegalovirus UL128 Complex Induces Broadly Neutralizing Antibodies in Rhesus Macaques", Journal of Virology, Feb. 2013, vol. 87, No. 3, pp. 1322-1332.
Achour et al., "Human herpesvirus-6 (HHV-6) Dna in plasma reflects the presence of infected blood cells rather than circulating viral particles"; Journal of Clinical Virology, 2007, vol. 38, pp. 280-285.
Akter et al., "Two novel spliced genes in human cytomegalovirus", Journal of General Virology, 2003, vol. 84, pp. 1117-1122.
PrabhuDas et al., "Challenges in infant immunity: implications for responses to infection and vaccines", Nature Immunology, Mar. 2011, vol. 12, No. 3, pp. 189-194.
Cui et al., "Rabbits immunized with Epstein-Barr virus gH/gL or GB recombinant proteins elicit higher serum virus neutralizing activity than gp350", Vaccine, 2016, vol. 34, pp. 4050-4055.
Amy W Hudson, "Roseoloviruses and their modulation of host defenses", Current Opinion in Virology, 2014, vol. 9, p. 178-187.
Ellinger et al., "The glycoprotein B homologue of human herpesvirus 6", Journal of General Virology, 1993, vol. 74, pp. 495-500.
Chandran et al., "Chapter 23 Gammaherpesviruses entry and early events during infection", Gammaherpesviruses entry and early events during infection—Human Herpesviruses—NCBI Bookshelf, 2007, https://www.ncbi.nlm.nih.gov/books/NBK47405/?report=printable, 55 Pages.
Gilden et al., "The neurobiology of varicella zoster virus infection", Neuropathol Appl Neurobiol., Aug. 2011, vol. 37, No. 5, pp. 441-463.
Peeters et al., "Effect of Carrier Priming on Immunogenicity of Saccharide-Protein Conjugate Vaccines", Infection and Immunity, Oct. 1991, vol. 59, No. 10, pp. 3504-3510.
Santoro et al., "Interaction of Glycoprotein H of Human Herpesvirus 6 with the Cellular Receptor CD46", the Journal of Biological Chemistry, Jul. 11, 2003, vol. 278, No. 28, pp. 25964-25969.
Patrone et al., "Human Cytomegalovirus UL130 Protein Promotes Endothelial Cell Infection through a Producer Cell Modification of the Virion", Journal of Virology, Jul. 2005, vol. 79, No. 13, pp. 8361-8373.
Ryckman et al., "Characterization of the Human Cytomegalovirus gH/gL/UL128-131 Complex That Mediates Entry into Epithelial and Endothelial Cells", Journal of Virology, Jan. 2008, vol. 82, No. 1, pp. 60-70.
Yang et al., "A role for the aV integrin subunit in Varicella Zoster Virus-mediated fusion and infection", Journal of Virology, 2016, 45 Pages.
Flamand et al., "Activation of the Epstein-Barr Virus Replicative Cycle by Human Herpesvirus 6", Journal of Virology, Nov. 1993, vol. 67, No. 11, pp. 6768-6777.
P. J. Klasse, "Neutralization of Virus Infectivity by Antibodies: Old Problems in New Perspectives", Advances in Biology, 2014, vol. 2014, Article ID 157895, 24 Pages.
Magdalena Anna Krzyzaniak, "Role of The gM/gN Glycoprotein Complex in the Final Assembly and Egress of the Human Cytomegalovirus (HCMV)", a Dissertation Submitted to the graduate faculty of the University of Alabama at Birmingham, in partial fulfillment of the requirements for the degree of Doctor of Philosophy, Birmingham, Alabama, 2008, 160 pages.
Edward S. Mocarski, Jr., "Immune escape and exploitation strategies of cytomegaloviruses: impact on and imitation of the major histocompatibility system", Cellular Microbiology, 2004, vol. 6, No. 8, pp. 707-717.
Martin I. Muggeridge, "Characterization of cell-cell fusion mediated by herpes simplex virus 2 glycoproteins GB, gD, gH and gL in transfected cells", Journal of General Virology, 2000, vol. 81, pp. 2017-2027.
Ciferri et al., "Structural and biochemical studies of HCMV gH/gL/gO and Pentamer reveal mutually exclusive cell entry complexes", PNAS, Feb. 10, 2015, vol. 112, No. 6, p. 1767-1772.
Laurie T Krug, "Editorial overview: Roseoloviruses: Stopping to smell the roses—the Roseoloviruses have come of age as human pathogens", Current Opinion in Virology, 2014, vol. 9, pp. vi-vii.
Krug et al., "Roseolovirus molecular biology: recent advances", Current Opinion in Virology, 2014, vol. 9, pp. 170-177.
Caserta et al., "Roseoloviruses: unmet needs and research priorities Perspective", Current Opinion in Virology, 2014, vol. 9, pp. 167-169.
Frenkel et al., "Roseoloviruses manipulate host cell cycle", Current Opinion in Virology, 2014, vol. 9, pp. 162-166.
Becerra et al., "Immune response to HHV-6 and implications for immunotherapy", Current Opinion in Environmental Sustainability, 2014, vol. 9, pp. 154-161.

(56) References Cited

OTHER PUBLICATIONS

Prichard et al., "The development of new therapies for human herpesvirus 6", Current Opinion in Virology, 2014, vol. 9, pp. 148-153.
Leibovitch et al., "Evidence linking HHV-6 with multiple sclerosis: an update", Current Opinion in Virology, 2014, vol. 9, pp. 127-133.
Kaufer et al., "Chromosomally integrated HHV-6: impact on virus, cell and organismal biology", Current Opinion in Virology, 2014, vol. 9, pp. 111-118.
Horvat et al., "Recent developments in animal models for human herpesvirus 6A and 6B", Current Opinion in Virology, 2014, vol. 9, pp. 97-103.
Tesini et al., "Clinical impact of primary infection with roseoloviruses", Current Opinion in Virology, 2014, vol. 9, pp. 91-96.
Hill et al., "Past, present, and future perspectives on the diagnosis of Roseolovirus infections", Current Opinion in Virology, 2014, vol. 9, pp. 84-90.
Moorman et al., "Roseomics: a blank slate", Current Opinion in Virology, 2014, vol. 9, pp. 188-193.
Tang et al., "Human Herpesvirus 6 Glycoprotein Complex Formation is Required for Folding and Trafficking of the gH/gL/gQ1/gQ2 Complex and its Cellular Receptor Binding", Journal of Virology, Nov. 2011, vol. 85, No. 21, pp. 11121-11130.
Torrisi et al., "Intracellular Transport and Maturation Pathway of Human Herpesvirus 6", Virology, 1999, vol. 257, pp. 460-471.
Wills et al., "Vaccines against persistent DNA virus infections", British Medical Bulletin, 2002, vol. 62, pp. 125-138.
Extended Search Report dated Dec. 1, 2020 for corresponding European Application No. 18744000.3, 7 pages.
Backovic et al., "Structure of a trimeric variant of the Epstein-Barr virus glycoprotein B", PNAS, 2009, vol. 106, No. 8, pp. 2880-2885.
Edward S. Mocarski Jr., "Comparative analysis of herpesvirus-common proteins", Human Herpesviruses: Biology, Therapy, and Immunoprophylaxis, Cambridge: Cambridge University Press, 2007, Chapter 4, 19 pages.
Xu et al., "Seroprevalence and Coinfection with Herpes Simplex Virus Type 1 and Type 2 in the United States, 1988-1994", The Journal of Infectious Diseases, 2002, vol. 185, No. 8, pp. 1019-1024.
Cui X, Snapper CM. Development of novel vaccines against human cytomegalovirus. Hum Vaccin Immunother. 2019; 15(11):2673-2683. doi: 10.1080/21645515.2019.1593729. Epub Apr. 24, 2019. PMID: 31017831; Pmcid: PMC6930071. (Year: 2019).
Cui X, Snapper CM. Epstein Barr Virus: Development of Vaccines and Immune Cell Therapy for EBV-Associated Diseases. Front Immunol. Oct. 8, 2021; 12:734471. doi: 10.3389/fimmu.2021.734471. PMID: 34691042; PMCID: PMC8532523. (Year: 2021).
Cui X, Cao Z, Ishikawa Y, Cui S, Imadome KI, Snapper CM. Immunization with Epstein-Barr Virus Core Fusion Machinery Envelope Proteins Elicit High Titers of Neutralizing Activities and Protect Humanized Mice from Lethal Dose EBV Challenge. Vaccines (Basel). Mar. 19, 2021; 9(3):285. (Year: 2021).

* cited by examiner

VACCINE COMPOSITIONS OF HERPESVIRUS ENVELOPE PROTEIN COMBINATIONS TO INDUCE IMMUNE RESPONSE

REFERENCE TO A SEQUENCE LISTING XML

This application contains a Sequence Listing which has been submitted electronically in XML format. The Sequence Listing XML is incorporated herein by reference. Said XML file, created on Jan. 25, 2024, is named 2959612_005-US3_SL.xml and is 75,726 bytes in size.

CROSS-REFERENCE TO RELATED APPLICATIONS

This application is a continuation application of U.S. patent application Ser. No. 17/165,310 filed 2 Feb. 2021, which is a continuation application of U.S. patent application Ser. No. 16/480,098 filed 23 Jul. 2019, now issued as U.S. Pat. No. 11,572,389, which is a U.S. National Stage application of PCT/US2018/015459 filed Jan. 26, 2018, which claims the benefit of, and relies on the filing date of, U.S. provisional patent application No. 62/451,396 filed 27 Jan. 2017, the entire disclosure of which is incorporated herein by reference.

GOVERNMENT INTEREST

This invention was made with government support under grant Q574LJ15 awarded by the Uniformed Services University. The government has certain rights in the invention.

SEQUENCE LISTING

The instant application contains a Sequence Listing which has been submitted electronically in ASCII format and is hereby incorporated by reference in its entirety. Said ASCII copy, created on 25 Jan. 2018, is named HMJ-153-PCT_SL.txt and is 207,545 bytes in size.

BACKGROUND

Human herpes viruses are a group of enveloped DNA viruses responsible for significant global morbidity and mortality in humans. (Eisenberg et al., Viruses, 4:800-32, 2012). There are eight types of known human herpes virus (HHV), including: (i) Type 1 human herpes virus (HHV-1), which is herpes simplex virus-1 (HSV-1); (ii) HHV-2 which is herpes simplex virus-2 (HSV-2); (iii) HHV-3 which is varicella-Zoster virus (VZV); (iv) HHV-4 which is Epstein Barr virus (EBV); (v) HHV-5, which is human cytomegalovirus (HCMV); (vi) HHV-6; (vii) HHV-7; and (viii) HHV-8 which is Kaposi's sarcoma-associated herpesvirus (KSHV).

In humans, these viruses are known to cause the following diseases. HSV-1 causes oral herpes, HSV-2 causes genital herpes, and VZV causes chickenpox and shingles. EBV causes infectious mononucleosis and is strongly associated with several B cell lymphomas, nasopharyngeal carcinoma, and gastric adenocarcinoma. HCMV causes severe infection in immunosuppressed patients and is the leading non-genetic cause of hearing loss. HHV-6 and 7 cause *roseola infantum* (Sixth disease), and HVV-8 causes Kaposi's sarcoma in several clinical settings including in patients infected with human immunodeficiency virus (HIV).

EBV primarily infects B cells and nasopharyngeal epithelial cells. EBV infection of B cells is initiated by binding of the EBV envelope protein gp350 to the complement receptor CR2/CD21. (Hutt-Fletcher, *J. Virol.,* 81:7825-32, 2007; and Shannon-Lowe et al., *Curr. Opin. Virol.,* 4:78-84, 2014). Upon binding to B cell CR2, EBV gp42 interacts with cell surface MHC-II receptors, leading to its association with the heterodimeric EBV gH/gL protein. The heterodimer gH/gL then undergoes a conformational change upon binding gp42, leading to activation of the EBV fusion protein gB, that directly mediates viral-host cell membrane fusion. (Neuhierl et al., *Proc. Natl. Acad. Sci. U.S.A.,* 99:15036-41, 2002). Like EBV, the binding, fusion and host cell entry of other HHV family members is mediated primarily by the gB, gH, and gL polypeptides, in conjunction with other accessory proteins, which typically bind to different receptors on the host cell surface.

There is currently no prophylactic EBV vaccine in clinical use. Studies in non-human primates using gp350-based vaccination strategies have shown protection against EBV-induced lymphoma and EBV replication. (Cohen, *Clin. Transl. Immunology,* 4:e32, 2015). A phase II clinical trial conducted in EBV-seronegative young adults using a recombinant monomeric gp350 protein versus placebo suggested a partial protective effect of gp350 vaccination on infectious mononucleosis (IM) development. (Sokal et al., *J. Infect. Dis.,* 196:1749-53, 2007; and Moutschen et al., *Vaccine,* 25:4697-705, 2007). However, the vaccine did not prevent asymptomatic EBV infection. A phase I trial of recombinant monomeric gp350 protein given to children with chronic kidney disease demonstrated only a minority of subjects developing detectable neutralizing serum anti-gp350 titers. (Rees et al., *Transplantation,* 88:1025-9, 2009).

There is also no prophylactic HCMV vaccine commercially available today. Earlier clinical trials using live attenuated Towne or AD169 HCMV viral vaccines, both of which lacked expression of a pentameric complex (gH/gL/UL128/UL130/UL131A), proved to be ineffective in preventing HCMV infection in either healthy volunteers or renal transplant recipients, though some efficacy was demonstrated in overt HCMV disease in high risk Recipient-Donor+renal transplant recipients (Fu et al., *Vaccine,* 32:2525-33, 2014). New HCMV viral strains engineered to express the pentameric complex are currently being evaluated, but safety concerns persist using this approach. A phase II clinical trial using recombinant HCMV gB protein derived from the Towne strain of HCMV (Spaete R R, *Transplant Proc.,* 23:90-6, 1991) demonstrated 50% efficacy in preventing HCMV infection in HCMV seronegative women (Pass R F, *J. Clin. Virol.,* 46 Suppl 4:S73-6, 2009) and 50% efficacy in preventing HCMV viremia in solid organ transplantation patients. The HCMV gB protein used in Phase II clinical trials had been modified to remove the furin cleavage site. Thus, the gB did not assume its native trimeric conformation (Sharma et al., *Virology,* 435:239-49, 2013). Although these two studies have encouraged further evaluation of gB as a prophylactic HCMV vaccine, they indicate a compelling need for a more effective prophylactic vaccine formulation.

WO2014/018858 and WO2015/089340 describe strategies for enhancing immunity that involve multimerizing antigens. For example, WO2014/018858 describes fusion proteins comprising at least two antigens, separated by a linker sequence, and an oligomerization domain, including multimeric HHV antigens, such as gp350, gB, gH, and gL. WO2015/089340 describes a modified herpesvirus gB obtained by inserting a peptide linker at the furin cleavage site in the herpesvirus gB polypeptide extracellular domain.

Inserting the peptide linker removes the furin recognition sequence, such that expression of the modified herpesvirus gB results in the production of a homotrimeric gB complex that provides enhanced immunogenicity.

Combining multiple antigens in a vaccine does not necessarily result in enhanced immunity or even additive effects. In fact, when multiple antigens are co-administered as part of a multicomponent vaccine or as part of a sequential immunization schedule, the antibody response to one or more of the antigens may be reduced or diminished due to vaccine or immune interference. (PrabhuDas et al., *Nature Immunology,* 12(3):189-194, 2011). Similarly, when certain haptens are combined with a carrier protein, the antibody response to the hapten is often inhibited if the recipient has been previously immunized with the carrier protein. This phenomenon has been called carrier-induced epitope suppression and has been demonstrated to occur with a number of peptide-carrier protein conjugates. (Peeters et al., *Infection and Immunity,* 59(10):3504-3510, 1991). It can also occur when certain saccharides are combined with a carrier protein, particularly when the recipient is primed with a high dose of the carrier protein (i.e., a dose high enough to induce an antibody response to the carrier protein). (Peeters et al., *Infection and Immunity,* 59(10):3504-3510, 1991). Thus, often times, when two or more antigens are administered to a subject, the antibody response to one or more of the antigens is diminished due to immune interference. Therefore, when administering multiple proteins as part of a vaccination or immunization schedule, it is important to carefully evaluate the interactions between the proteins and how those interactions might affect the immune system's response.

New and improved antigen compositions for enhancing immune responses to HHV are needed.

SUMMARY

Human herpes viruses share a general strategy for infection of host cells. Specifically, the envelope membrane of the virus fuses with the plasma membrane of the host cell, with subsequent entry into the cytoplasm, or the envelope membrane of the virus fuses with the endosomal membrane after the virus is endocytosed and then enters the cytoplasm of the host cell. The core HHV envelope proteins involved in the fusion process are the conserved glycoprotein B (gB), glycoprotein H (gH), and glycoprotein L (gL). The gH and gL proteins typically form a noncovalently associated heterodimeric complex during the fusion process.

As disclosed in this application, immunization with a combination of two or more of these HHV proteins involved in mediating HHV binding, fusion, and entry into host cells, such as gp350, gH, gL, and gB, produces additive or synergistic antibody responses. These robust results are particularly unexpected in view of the art-recognized problem of vaccine or immune interference, commonly observed when administering multiple antigens as part of a multicomponent vaccine or a sequential vaccination schedule. Without intending to be bound by any theory, it appears that the combination of two or more HHV polypeptides elicits high-titer, neutralizing antibody responses that block different steps of the virus-host cell fusion process and, thus, provide improved protection against HHV infection in vivo.

Although strategies for multimerizing HHV proteins to enhance immunogenicity have recently been reported (see e.g., WO2014/018858 and WO2015/089340), we have discovered that unexpected additive and synergistic antibody responses can be obtained by combining monomeric or multimeric forms of the HHV fusion and host cell entry protein. Thus, in certain embodiments, one or more of the HHV fusion and host cell entry proteins is monomeric and/or multimeric. The HHV fusion and host cell entry proteins can be recombinant proteins or native proteins. In certain embodiments, the HHV fusion and host cell entry proteins have been modified and are not naturally occurring proteins. For example, the proteins may be truncated, multimerized, or combined in a fusion protein.

Although typically administered as polypeptides, it is also possible to administer nucleic acids encoding the HHV fusion and host cell entry proteins as a DNA vaccine, an RNA vaccine, or a viral vector vaccine. It is also possible to administer virus-like particles that express the HHV fusion and host cell entry proteins.

The present disclosure also discloses for the first time that high titer anti-HHV antibodies, such as antibodies generated in response to the HHV protein combinations disclosed herein, can passively transfer immunity and protect against HHV infection. This aspect covers methods of identifying biological samples that contain high titer anti-HHV antibodies and collecting antibodies and/or immune cells from individuals that are highly seropositive for HHV antigens, and/or individuals who have been administered the antigenic compositions disclosed herein, and administering those antibodies and/or immune cells to a subject in need thereof, thereby passively transferring immunity to the subject and protecting the subject from HHV infection, particularly in individuals who are immunocompromised or otherwise at risk of developing an HHV infection.

In a first aspect, the present disclosure provides antigenic compositions that include at least two of the following antigenic human herpesvirus polypeptides (or one or more nucleic acids encoding the same): a glycoprotein B (gB) polypeptide comprising an extracellular domain of human herpesvirus gB; a glycoprotein 350 (gp350) polypeptide comprising an extracellular domain of human herpesvirus gp350; a glycoprotein L (gL) polypeptide; and a glycoprotein H (gH) polypeptide comprising an extracellular domain of human herpesvirus gH. Such compositions may optionally include adjuvants and/or excipients common in the field of vaccine development.

The human herpes virus from which the polypeptides are obtained can be human cytomegalovirus (HCMV), Herpes Simplex Virus-1 (HSV-1), Herpes Simplex Virus-2 (HSV-2), Varicella-Zoster Virus (VZV), Epstein-Barr Virus (EBV), Human Herpes Virus 6 (HHV 6), Human Herpes Virus 7 (HHV 7), and/or Kaposi Sarcoma-related Herpes Virus (HSHV). In one embodiment, the polypeptides are EBV polypeptides.

In certain embodiments, the gB polypeptide, the gp350 polypeptide, the gL polypeptide, and/or the gH polypeptide, when present in the antigenic composition, each further comprises a corresponding intracellular domain. The extracellular domain of the selected polypeptides can be fused to the intracellular domain via a polypeptide linker sequence of about 6 to about 70 amino acids in length, or in particular about 15 amino acids in length, for example. In other embodiments, at least two, or optionally three, of the human herpesvirus polypeptides form a fusion protein, wherein the fusion protein optionally comprises a polypeptide linker sequence that covalently links the polypeptides.

In a further embodiment, the antigenic composition includes the gB polypeptide and one or more of the gp350, gL, and gH polypeptides. In various embodiments mentioned herein, the gB polypeptide can be monomeric or multimeric (e.g., dimeric, trimeric, tetrameric, etc.). In certain embodiments, the antigenic composition comprises the gB polypeptide, the gH polypeptide, and the gL polypeptide. The gL and gH polypeptides can optionally be present as a heterodimer. In certain embodiments, the heterodimer is a fusion protein. In other embodiments, the heterodimer is a non-covalently associated protein complex. In one embodiment, the gB polypeptide is monomeric, dimeric, or trimeric and the gL and gH polypeptides form a heterodimer. In another embodiment, the gB polypeptide is monomeric and the gL and gH polypeptides form a monomeric heterodimer.

In HCMV embodiments of the antigenic compositions, at least the following combinations are contemplated: gB polypeptide, the gH polypeptide, and the gL polypeptide. In one embodiment, the gB polypeptide is monomeric, dimeric, or trimeric and the gL and gH polypeptides form a heterodimer, which can be monomeric or multimeric (e.g., monomeric, dimeric, trimeric, or tetrameric). In another embodiment, the gB polypeptide is monomeric or trimeric and the gL and gH polypeptides form a monomeric or trimeric heterodimer. These antigenic compositions can further include a HCMV glycoprotein O (gO) polypeptide or an HCMV unique long 128 (UL128) polypeptide, an HCMV unique long 130 (UL130) polypeptide, and an HCMV unique long 131A (UL131A) polypeptide, and optionally an HCMV glycoprotein M polypeptide, and/or an HCMV glycoprotein N polypeptide.

In EBV embodiments of the antigenic compositions, at least the following combinations are contemplated: (a) the gp350 polypeptide and the gB polypeptide, wherein the gp350 polypeptide is monomeric or tetrameric gp350, and wherein the gB polypeptide is trimeric gB; (b) the gp350 polypeptide, the gH polypeptide, and the gL polypeptide, where (i) the polypeptides are monomeric, or (ii) the gp350 polypeptide is tetrameric, and the gH and gL polypeptides are trimeric; (c) the gB polypeptide, the gH polypeptide, and the gL polypeptide, where the gB polypeptide is trimeric gB, and where the gH polypeptide and gL polypeptide are both monomeric or trimeric; and (d) monomeric gp350 polypeptide, monomeric gH polypeptide and monomeric gL polypeptide, and trimeric gB polypeptide, where the gp350 polypeptide is tetrameric, the gH and gL polypeptides are monomeric or trimeric, and the gB polypeptide is trimeric. EBV antigen compositions can also optionally include a human EBV glycoprotein 42 (gp42) polypeptide, BDLF2 polypeptide, and/or a human EBV BamHI1-M rightward reading frame 2 (BMRF-2) polypeptide.

In HSV-1 and/or HSV-2 embodiments of the antigenic compositions, at least the following combinations are contemplated: the gH polypeptide, the gL polypeptide, and the gB polypeptide, wherein each polypeptide is monomeric or multimeric and optionally wherein the gH and gL polypeptides form a gH/gL heterodimer. In certain embodiments, the gH/gL heterodimer is monomeric, dimeric, trimeric, or tetrameric and the gB polypeptide is monomeric, dimeric, or trimeric. In one embodiment, the combination comprises a monomeric or trimeric gH/gL heterodimer and a monomeric or trimeric gB polypeptide. These antigenic compositions can also optionally include an HSV-1 or HSV-2 glycoprotein D (gD) polypeptide, in monomeric, dimeric, trimeric, or tetrameric form.

In VZV embodiments of the antigenic compositions, at least the following combinations are contemplated: the gH polypeptide, the gL polypeptide, and the gB polypeptide, wherein each polypeptide is monomeric or multimeric and optionally wherein the gH and gL polypeptides form a gH/gL heterodimer. In certain embodiments, the gH/gL heterodimer is monomeric, dimeric, trimeric, or tetrameric and the gB polypeptide is monomeric, dimeric, or trimeric. In one embodiment, the combination comprises a monomeric or trimeric gH/gL heterodimer and a monomeric or trimeric gB polypeptide. These antigenic compositions can also optionally include one or more of a human VZV glycoprotein C (gC) polypeptide, human VZV glycoprotein E (gE) polypeptide, and/or human VZV glycoprotein I (gI) polypeptide.

In HHV-6 or HHV-7 embodiments of the antigenic compositions at least the following combinations are contemplated: the gH polypeptide, the gL polypeptide, and the gB polypeptide, wherein each polypeptide is monomeric or multimeric and optionally wherein the gH and gL polypeptides form a gH/gL heterodimer. In certain embodiments wherein the gH/gL heterodimer is monomeric, dimeric, trimeric, or tetrameric and the gB polypeptide is monomeric, dimeric, or trimeric. In one embodiment, the combination comprises a monomeric or trimeric gH/gL heterodimer and a monomeric or trimeric gB polypeptide.

In KSHV embodiments of the antigenic compositions, at least the following combinations are contemplated: the gH polypeptide, the gL polypeptide, and the gB polypeptide, wherein each polypeptide is monomeric or multimeric and optionally wherein the gH and gL polypeptides form a gH/gL heterodimer. In certain embodiments, the gH/gL heterodimer is monomeric, dimeric, trimeric, or tetrameric and the gB polypeptide is monomeric, dimeric, or trimeric. In one embodiment, the combination comprises a monomeric or trimeric gH/gL heterodimer and a monomeric or trimeric gB polypeptide. These antigenic compositions can also optionally include one or more of a human KSHV glycoprotein M (gM) polypeptide, a human KSHV glycoprotein N (gN) polypeptide, a human KSHV Open Reading Frame 68 (ORF68) polypeptide, and/or a human KSHV K8.1 polypeptide.

In antigenic compositions comprising nucleic acids, the nucleic acids can be in a viral vector that permits expression of the human herpesvirus polypeptides.

Also provided are methods for preventing or treating a human herpesvirus infection in a subject by administering a therapeutically effective amount of two or more of the HHV polypeptides that comprise the disclosed antigen compositions. Further, provided are methods for inducing immunity to a human herpesvirus in a subject by administering a therapeutically effective amount of two or more of the HHV fusion and host cell entry proteins that comprise one or more of the disclosed antigenic compositions. The two or more HHV fusion and host cell entry proteins may be administered simultaneously or separately.

The treated subjects can be those who are at risk of developing post-transplantation lymphoproliferative disorder (PTLD) following hematopoietic stem cell or solid organ transplantation and/or those suffering from a primary immunodeficiency syndrome. In the disclosed methods, the antigenic compositions can be administered sequentially or concurrently.

Recombinant nucleic acid constructs for expressing the HHV polypeptides or protein complexes are also disclosed, as well as their corresponding encoded polypeptides.

In one embodiment, the recombinant nucleic acid construct includes a first nucleic acid molecule encoding a HHV gL polypeptide, a second nucleic acid molecule encoding a HHV gH polypeptide, a third nucleic acid molecule encoding a HHV UL128 polypeptide, a fourth nucleic acid molecule encoding a HHV UL130 polypeptide, and a fifth nucleic acid molecule encoding a HHV UL131A polypeptide. In certain embodiments, a pentameric gH/gL/UL128/

UL130/UL131A protein complex is formed when the polypeptides are expressed from the nucleic acid construct in a host cell. The polypeptides optionally do not include a transmembrane domain and/or an intracellular domain. In one embodiment, the recombinant nucleic acid construct further includes a first promoter operatively linked to the first nucleic acid and a second promoter operatively linked to the third nucleic acid molecule. The nucleic acid construct optionally also includes a first internal ribosome entry site (IRES) located between the first nucleic acid molecule and the second nucleic acid molecule, a second IRES located between the third nucleic acid molecule and the fourth nucleic acid molecule, and a third IRES located between the fourth nucleic acid molecule and the fifth nucleic acid molecule. Optionally, the nucleic acid construct also includes a first, second, third, fourth, and fifth nucleotide sequence encoding an IgG kappa light chain leader peptide, wherein the first, second, third, fourth, and fifth nucleotide sequence encoding the IgG kappa light chain leader peptide is in frame with the first, second, third, fourth, and fifth nucleic acid molecules, respectively. In certain embodiments, the HHV is HCMV, EBV, HSV-1, HSV-2, VZV, KSHV.

In another embodiment, the recombinant nucleic acid construct includes a first nucleic acid molecule encoding a HHV gL polypeptide, a second nucleic acid molecule encoding a HHV gH polypeptide, and a third nucleic acid molecule encoding a HHV gO polypeptide. In certain embodiments, a trimeric gL/gH/gO protein complex is formed when the polypeptides are expressed from the nucleic acid construct in a host cell. In certain embodiments, the HHV is HCMV, EBV, HSV-1, HSV-2, VZV, or KSHV.

Methods of passively transferring immunity against Epstein-Barr virus (EBV) are also disclosed. These methods are achieved by administering to a subject in need thereof immune cells or high titer anti-EBV immunoglobulins, wherein the immune cells or high titer anti-EBV immunoglobulins have been obtained from one or more blood, plasma, or serum samples, optionally human blood, plasma, or serum samples, that have been selected for the high titer anti-EBV immunoglobulins. In these embodiments, the titer of the high titer anti-EBV immunoglobulins can be up to 25-fold, 4- to 25-fold, or 10- to 20-fold, higher than the average titer of anti-EBV immunoglobulins obtained from unselected blood, plasma, or serum samples. The blood, plasma, or serum samples can be obtained from a donor who was immunized with two or more EBV fusion and host cell entry proteins. The blood, plasma, or serum samples can also be obtained from a donor who was immunized with a single multimeric EBV protein involved in mediating EBV binding, fusion, and entry into host cells, including but not limited to, tetrameric gp350, trimeric gH/gL, or trimeric gB. Subjects in need thereof can be subjects that are at risk of developing post-transplantation lymphoproliferative disorder (PTLD) following hematopoietic stem cell or solid organ transplantation, or that have or are at risk of developing nasopharyngeal carcinoma (NPC), Burkitt lymphoma, Hodgkin's lymphoma, non-Hodgkin's lymphoma, gastric carcinoma, severe infectious mononucleosis, chronic active EBV infection, multiple sclerosis, systemic lupus erythematosus, or rheumatoid arthritis. In certain embodiments, the subject is seronegative for EBV.

In one embodiment, the method of passively transferring immunity against EBV is performed on a subject that is concurrently receiving one or more of anti-CD20 antibody administration, anti-viral therapy, interferon alpha administration, radiotherapy, and chemotherapy.

In another embodiment of the passive transfer method, the method includes one or more of the following steps: (i) identifying a blood, plasma, or serum sample obtained from one or more human subjects that contain high EBV neutralizing activity; and/or (ii) collecting high titer anti-EBV immunoglobulins from the blood, plasma or serum sample containing high EBV neutralizing activity. In this embodiment and related method embodiments, the identifying step optionally includes subjecting the blood, plasma, or serum sample to a Raji B cell neutralization assay and/or a HeLa cell neutralization assay. In this embodiment, the HeLa cell neutralization assay includes the steps of infecting HeLa cells with GFP labeled EBV to yield EBV-infected HeLa cells, incubating the blood, plasma, or serum sample with the EBV-infected HeLa cells, analyzing the neutralization activity of the blood, plasma, or serum sample with flow cytometry or ELISpot assay and optionally calculating the $IC_{50}$ of the blood, plasma, or serum sample. Also in this embodiment, the blood, plasma, or serum sample is identified as containing high EBV neutralizing activity if the blood, plasma, or serum sample has an $IC_{50}$ that is 4- to 25-fold, or 10- to 20-fold, higher than the average $IC_{50}$ of unselected blood, plasma or serum samples.

In another embodiment of the passive transfer method, the method includes administering to one or more human donor subjects at least two of the following EBV polypeptides: an EBV gp350 polypeptide, an EBV gH/gL heterodimer comprising an EBV gH polypeptide and an EBV gL polypeptide, and an EBV gB polypeptide, in an amount sufficient to generate high titer anti-EBV immunoglobulin, and collecting the high titer anti-EBV immunoglobulins from the one or more human donor subjects before the step of administering to the subject the high titer anti-EBV immunoglobulins. In certain embodiments, the EBV gp350 polypeptide is monomeric, dimeric, trimeric, or tetrameric, the EBV gB polypeptide is monomeric, dimeric, or trimeric, and the gH/gL heterodimer is monomeric, dimeric, trimeric, or tetrameric.

In a further embodiment, methods are provided for passively transferring immunity against human cytomegalovirus (HCMV). The methods include the step of administering to a subject in need thereof immune cells or high titer anti-HCMV immunoglobulins, where the immune cells or high titer anti-HCMV immunoglobulins have been obtained from one or more blood, plasma, or serum samples, optionally human blood, plasma, or serum samples, that have been selected for the high titer anti-HCMV immunoglobulins. Optionally, the blood, plasma or serum samples have been obtained from a donor who was immunized with two or more HCMV fusion and host cell entry proteins. The blood, plasma, or serum samples can also be obtained from a donor who was immunized with a single multimeric HCMV protein involved in mediating HCMV binding, fusion, and entry into host cells, including but not limited to, trimeric gH/gL or trimeric gB. In one embodiment of this passive transfer method, the subject is at risk of contracting HCMV infection is a pregnant woman, a transplantation patient, a patient who is immunosuppressed during chemotherapy or radiotherapy, or a patient infected with human immunodeficiency virus (HIV).

In another embodiment of the HCMV passive transfer method, the method also includes one or more of the following steps performed before the step of administering to the subject the high titer anti-HCMV immunoglobulins: (i) administering to one or more human donor subjects at least two of an HCMV gB polypeptide, an HCMV gH/gL heterodimer comprising an HCMV gH polypeptide and an HCMV gL polypeptide, an HCMV glycoprotein O (gO) polypeptide, an HCMV UL128 polypeptide, an HCMV UL130 polypeptide, and an HCMV unique UL131A polypeptide, in an amount sufficient to generate a high titer anti-HCMV immunoglobulin response in the subject; and (ii) collecting the high titer anti-HCMV immunoglobulins from the one or more human donor subjects. In certain embodiments, the HCMV gB polypeptide is monomeric, dimeric, or trimeric, and the gH/gL heterodimer is monomeric, dimeric, trimeric, or tetrameric.

Also disclosed are methods of passively transferring immunity against Herpes Simplex Virus Type 1 (HSV-1) or Herpes Simplex Virus Type 2 (HSV-2). These methods achieve passive transfer by administering to a subject in need thereof immune cells or high titer anti-HSV-1 and/or anti-HSV-2 immunoglobulins, wherein the immune cells or high titer anti-HSV-1 or anti-HSV-2 immunoglobulins have been obtained from one or more blood, plasma, or serum samples, optionally human blood, plasma, or serum samples, that have been selected for the high titer anti-HSV-1 or anti-HSV-2 immunoglobulins. Optionally, the blood, plasma or serum samples have been obtained from a donor who was immunized with two or more HSV-1 or HSV-2 fusion and host cell entry proteins. The blood, plasma, or serum samples can also be obtained from a donor who was immunized with a single multimeric HSV-1 or HSV-2 protein involved in mediating HSV-1 or HSV-2 binding, fusion, and entry into host cells, including but not limited to, trimeric gH/gL or trimeric gB. In another embodiment of this method, the subject is at risk of developing encephalitis caused by HSV-1 or HSV-2 infection, or wherein the subject is a pregnant woman with active HSV-2 or HSV-1 infection and/or HSV encephalitis.

In another embodiment of the HSV-2 or HSV-1 passive transfer method, the method also includes one or more of the following steps performed before the step of administering to the subject the high titer anti-HSV-2 or HSV-1 immunoglobulins: (i) administering to one or more human donor subjects at least two of an HSV-1 or HSV-2 glycoprotein D (gD) polypeptide, an HSV-1 or HSV-2 gH/gL heterodimer comprising an HSV-1 or HSV-2 gH polypeptide and an HSV-1 or HSV-2 gL polypeptide, an HSV-1 or HSV-2 gB polypeptide, in an amount sufficient to generate high titer anti-HSV-1 or HSV-2 immunoglobulins; and/or (ii) collecting the high titer anti-HSV-1 and/or anti-HSV-2 immunoglobulins from the one or more human donor subjects. In certain embodiments, the HSV-1 or HSV-2 gB polypeptide is monomeric, dimeric, or trimeric, and the HSV-1 or HSV-2 gH/gL heterodimer is monomeric, dimeric, trimeric or tetrameric.

Also disclosed are methods of passively transferring immunity against VZV. These methods achieve passive transfer by administering to a subject in need thereof immune cells or high titer anti-VZV innmunoglobulins, wherein the immune cells or high titer anti-VZV immunoglobulins have been obtained from one or more blood, plasma, or serum samples, optionally human blood, plasma, or serum samples, that have been selected for the high titer anti-VZV immunoglobulins. Optionally, the blood, plasma or serum samples have been obtained from a donor who was immunized with two or more VZV fusion and host cell entry proteins. The blood, plasma, or serum samples can also be obtained from a donor who was immunized with a single multimeric VZV protein involved in mediating VZV binding, fusion, and entry into host cells, including but not limited to, trimeric gH/gL or trimeric gB. In another embodiment of this method, the subject is at risk of developing Zoster (shingles) or Varicella (chickenpox).

In another embodiment of the VZV passive transfer method, the method also includes one or more of the following steps performed before the step of administering to the subject the high titer anti-VZV immunoglobulins: (i) administering to one or more human donor subjects at least two of a VZV gH/gL heterodimer comprising a VZV gH polypeptide and a VZV gL polypeptide, a VZV gB polypeptide, a VZV glycoprotein C (gC) polypeptide, a VZV glycoprotein E (gE) polypeptide, and a VZV glycoprotein I (gI) polypeptide, in an amount sufficient to generate high titer anti-VZV immunoglobulins; and/or (ii) collecting the high titer anti-VZV immunoglobulins from the one or more human donor subjects. In certain embodiments, the VZV gB polypeptide is monomeric, dimeric, or trimeric, and the VZV gH/gL heterodimer is monomeric, dimeric, trimeric, or tetrameric.

Also disclosed are methods of passively transferring immunity against human herpesvirus 6 (HHV-6) or human herpesvirus 7 (HHV-7). These methods achieve passive transfer by administering to a subject in need thereof immune cells or high titer anti-HHV-6 or anti-HHV-7 immunoglobulins, wherein the immune cells or high titer anti-HHV-6 or anti-HHV-7 immunoglobulins have been obtained from one or more blood, plasma, or serum samples, optionally human blood, plasma, or serum samples, that have been selected for the high titer anti-HHV-6 or anti-HHV-7 immunoglobulins. Optionally, the blood, plasma or serum samples have been obtained from a donor who was immunized with two or more HHV-6 or HHV-7 fusion and host cell entry proteins. The blood, plasma, or serum samples can also be obtained from a donor who was immunized with a single multimeric HHV-6 or HHV-7 protein involved in mediating HHV-6 or HHV-7 binding, fusion, and entry into host cells, including but not limited to, trimeric gH/gL or trimeric gB. In another embodiment of the HHV-6 or HHV-7 passive transfer method, the method also includes one or more of the following steps performed before the step of administering to the subject the high titer anti-HHV-6 or anti-HHV-7 immunoglobulins: (i) administering to one or more human donor subjects at least a HHV-6 or HHV-7 gH/gL heterodimer and a HHV-6 or HHV-7 gB polypeptide, in an amount sufficient to generate high titer anti-HHV-6 or anti-HHV-7 immunoglobulins; and/or (ii) collecting the high titer anti-HHV-6 or anti-HHV-7 immunoglobulins from the one or more human donor subjects. In certain embodiments, the HHV-6 or HHV-7 gB polypeptide is monomeric, dimeric, or trimeric, and the gH/gL heterodimer is monomeric, dimeric, trimeric, or tetrameric, Also disclosed are methods of passively transferring immunity against Kaposi's sarcoma herpesvirus (KSHV). These methods achieve passive transfer by administering to a subject in need thereof immune cells or high titer anti-KSHV immunoglobulins, wherein the immune cells or high titer anti-KSHV immunoglobulins have been obtained from one or more blood, plasma, or serum samples, optionally human blood, plasma, or serum samples, that have been selected for the high titer anti-KSHV immunoglobulins. Optionally, the blood, plasma or serum samples have been obtained from a donor who was immunized with two or more KSHV fusion and host cell entry proteins. The blood, plasma, or serum samples can also be obtained from a donor who was immunized with a single multimeric KSHV protein involved in mediating KSHV binding, fusion, and entry into host cells, including but not limited to, trimeric gH/gL or trimeric gB. In another embodiment of this method, the subject is at risk of developing KSHV-associated Kaposi's sarcoma, primary effusion lymphoma, multicentric Castleman's disease, KSHV-associated inflammatory cytokine syndrome, or KSHV immune reconstitution inflammatory syndrome.

In another embodiment of the KSHV passive transfer method, the method also includes one or more of the following steps performed before the step of administering to the subject the high titer anti-KSHV immunoglobulins: (i) administering to one or more human donor subjects at least two of a KSHV gH/gL heterodimer comprising a KSHV gH polypeptide and a KSHV gL polypeptide, a KSHV gB polypeptide, a KSHV gM polypeptide, a KSHV gN polypeptide, a KSHV ORF68 polypeptide, and a KSHV K8.1 polypeptide, in an amount sufficient to generate high titer anti-KSHV immunoglobulins; and/or (ii) collecting the high titer anti-KSHV immunoglobulins from the one or more human donor subjects. In certain embodiments, the KSHV gB polypeptide is monomeric, dimeric, or trimeric, and the gH/gL heterodimer is monomeric, dimeric, trimeric, or tetrameric.

BRIEF DESCRIPTION OF THE DRAWINGS

The accompanying drawings, which are incorporated in and constitute a part of this specification, illustrate certain embodiments, and together with the written description, serve to explain certain principles of the constructs and methods disclosed herein.

FIG. 1 discloses "$(Gly_4Ser_1)3$" as SEQ ID NO: 3, "$His_6$" as SEQ ID NO: 49, and "RRRRRD" as SEQ ID NO: 55.

FIG. 7A shows survival rate of mice exposed to high-dose, live EBV infection after passive transfer of sera from rabbits immunized with tetrameric EBV gp350, trimeric EBV gH/gL, trimeric EBV gB, or adjuvant alone (control). FIG. 7B shows pooled immune sera from rabbits immunized with tetrameric EBV gp350 or trimeric EBV gH/gL decreased the copy number of EBV DNA in multiple organs of three humanized mice (geometric mean). FIG. 7C shows pooled immune sera from rabbits immunized with tetrameric EBV gp350, trimeric EBV gH/gL or trimeric EBV gB markedly decreased the EBV viral load in peripheral blood (geometric mean of 3 mice) compared to the control.

FIG. 8 discloses "GGGGSGGGGSGGGGS" as SEQ ID NO: 3, "$His_6$" as SEQ ID NO: 49, and "RTKRS" as SEQ ID NO: 53.

FIG. 10 discloses "$(Gly_4Ser)_3$" as SEQ ID NO: 3 and "$His_6$" as SEQ ID NO: 49.

DETAILED DESCRIPTION

Figure 1:
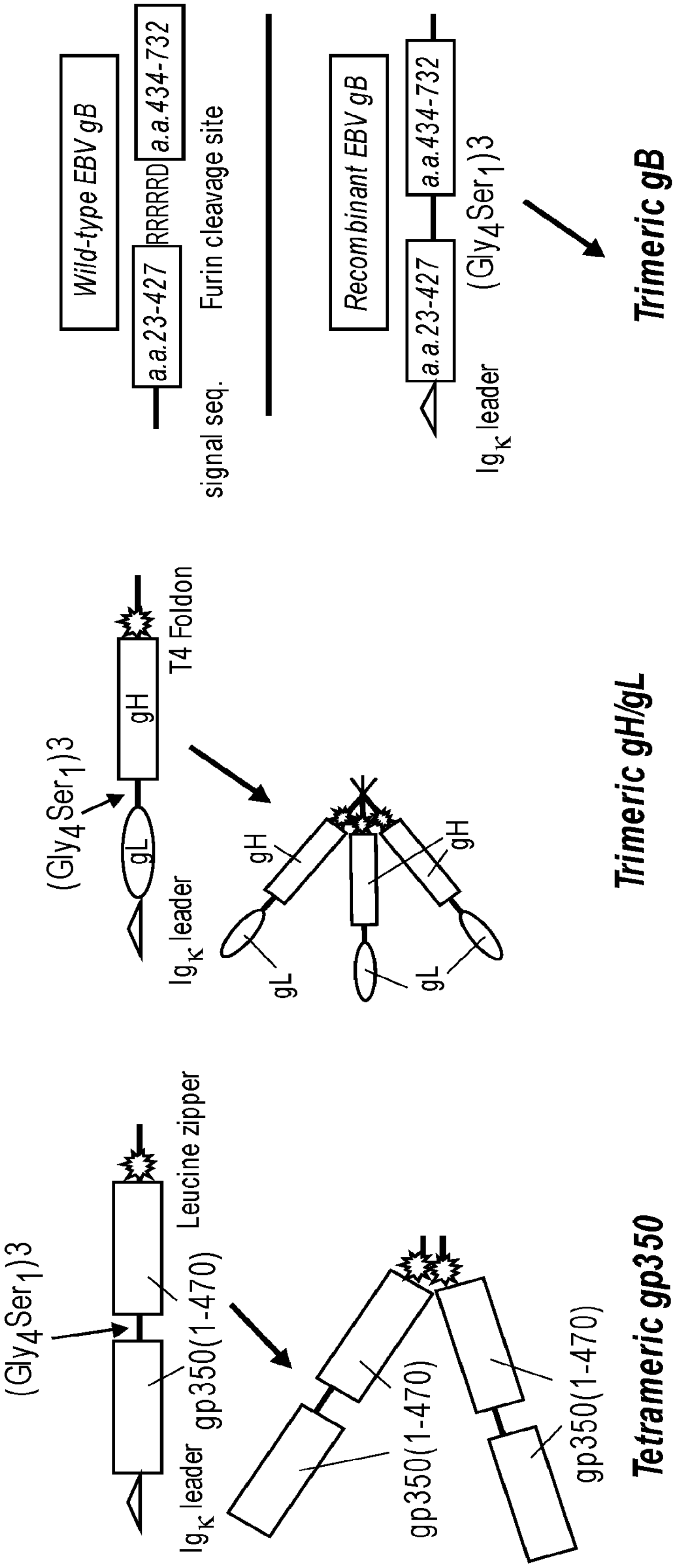
FIG. 1 shows a schematic of recombinant constructs for expressing non-limiting embodiments of multimeric EBV gp350, gH/gL, and gB.

It is to be understood that the following detailed description is provided to give the reader a fuller understanding of certain embodiments, features, and details of aspects of the invention, and should not be interpreted as a limitation of the scope of the invention.

Definitions

In order that the present invention may be more readily understood, certain terms are first defined. Additional definitions are set forth throughout the detailed description.

The term "antibody" as used in this disclosure refers to an immunoglobulin or an antigen-binding fragment thereof. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda.

The terms "antigen-binding domain" and "antigen-binding fragment" refer to a part of an antibody molecule that comprises amino acids responsible for the specific binding between the antibody and antigen. For certain antigens, the antigen-binding domain or antigen-binding fragment may only bind to a part of the antigen. The part of the antigen that is specifically recognized and bound by the antibody is referred to as the "epitope" or "antigenic determinant." Antigen-binding domains and antigen-binding fragments include Fab (Fragment antigen-binding); a $F(ab')_2$ fragment, a bivalent fragment having two Fab fragments linked by a disulfide bridge at the hinge region; Fv fragment; a single chain Fv fragment (scFv) see e.g., Bird et al. (1988) *Science* 242:423-426; and Huston et al. (1988) *Proc. Natl. Acad. Sci. USA* 85:5879-5883); a Fd fragment having the two $V_H$ and $C_H$I domains; dAb (Ward et al., (1989) *Nature* 341:544-546), and other antibody fragments that retain antigen-binding function. The Fab fragment has $V_H$-$C_H$1 and $V_L$—$C_L$ domains covalently linked by a disulfide bond between the constant regions. The $F_v$ fragment is smaller and has $V_H$ and $V_L$ domains non-covalently linked. To overcome the tendency of non-covalently linked domains to dissociate, a $scF_v$ can be constructed. The $scF_v$ contains a flexible polypeptide that links (1) the C-terminus of $V_H$ to the N-terminus of $V_L$, or (2) the C-terminus of $V_L$ to the N-terminus of $V_H$. A 15-mer $(Gly_4Ser)_3$ peptide (SEQ ID NO:3) may be used as a linker, but other linkers are known in the art. These antibody fragments are obtained using conventional techniques known to those with skill in the art, and the fragments are evaluated for function in the same manner as are intact antibodies.

As used in this application, "antigen" means a protein or fragment thereof or a polysaccharide linked to a protein carrier that, when expressed in an animal or human cell or tissue, is capable of triggering an immune response. The protein or fragment thereof may be glycosylated or non-glycosylated.

The term "extracellular domain" means refers to the portion of a full length polypeptide that extends beyond the cellular membrane and into the media in which the cell harboring the polypeptide resides. Polypeptides are known to generally contain an intracellular domain, transmembrane domain, and the remaining is the extracellular domain ("ECD"). When the term "extracellular domain" or "ECD" is used herein, it refers to the amino acids of a polypeptide that in wild type form extend beyond the cellular membrane, or any portion thereof recognizable by an antibody. Thus, the extracellular domain includes the entire domain, or any number of residues amenable to recombinant expression and inclusion in an antigenic composition, including polypeptides representing 75%, 80%, 85%, 90%, 95%, 96%, 97%, 98%, 99%, or 100% of the entire wild type extracellular domain of a polypeptide. That is, the extracellular domain may be shortened, or truncated, by known methods in the art, to remove extraneous domains, on either the carboxy-terminus or amino-terminus end, or both, of the polypeptide as needed to obtain more efficient and robust expression of the extracellular domain of the polypeptide.

The term "full length" with respect to a given polypeptide means the form of the polypeptide naturally translated from the coding DNA sequence, beginning with the ATG start codon, which encodes the first methionine in the amino acid sequence, and ending at the TGA, TAG, or TTA stop codon, or whichever stop codon employed by the organism.

The term "fusion protein" refers to a protein translated from a nucleic acid transcript generated by combining a first nucleic acid sequence that encodes a first protein and at least a second nucleic acid that encodes a second protein, where the fusion protein is not a naturally occurring protein. The nucleic acid construct may encode two or more proteins that are joined in the fusion protein to create a single polypeptide chain. The two or more nucleic acid sequences are optionally operatively linked to a single promoter, or operatively linked to two or more separate promoters.

The term "glycoprotein" means a polypeptide that has covalently attached to it one or more carbohydrate moieties, or oligosaccharide chains. The carbohydrate moieties are normally attached to glycoproteins co-translationally or as post-translational modifications.

The term "isolated," when used in the context of a polypeptide or nucleic acid refers to a polypeptide or nucleic acid that is substantially free of its natural environment and is thus distinguishable from a polypeptide or nucleic acid that might happen to occur naturally. For instance, an isolated polypeptide or nucleic acid is substantially free of cellular material or other polypeptides or nucleic acids from the cell or tissue source from which it was derived. The term also refers to preparations where the isolated polypeptide or nucleic acid is sufficiently pure for pharmaceutical compositions; or at least 70-80% (w/w) pure; or at least 80-90% (w/w) pure; or at least 90-95% pure; or at least 95%, 96%, 97%, 98%, 99%, or 100% (w/w) pure.

The term "leader sequence" refers to a short peptide sequence at the N-terminus of a recombinant protein that directs the recombinant protein to be secreted from a host cell.

The term "HHV fusion and host cell entry protein" refers to a human herpesvirus gB polypeptide, gH polypeptide, gL polypeptide, gH/gL heterodimer, or gp350 polypeptide.

The term "HHV accessory protein" refers to a human herpes virus polypeptide other than gB, gH, gL, gH/gL, or gp350 that are involved in mediating viral binding, fusion, and host cell entry including, but not limited to, gp42, gM, gN, gI, gC, gD, ORF68, BMRF-2, BDLF2, UL128, UL130, UL131A, and gpK8.1.

The term "immune cell" means any cell of hematopoietic lineage involved in regulating an immune response against an antigen (e.g., an autoantigen). In typical embodiments, an immune cell is a leukocyte, such as a white blood cell. Immune cells include neutrophils, eosinophils, basophils, lymphocytes, and/or monocytes. Lymphocytes include T lymphocytes and B lymphocytes. Immune cells can also be dendritic cells, natural killer (NK) cells, and/or a mast cell.

The term "intracellular domain" means the portion of a polypeptide that resides in the cytoplasm of a host cell. The intracellular domain includes that portion of the polypeptide that is not the transmembrane domain and is not the extracellular domain.

The term "gH/gL heterodimer" refers to a polypeptide or polypeptide complex comprising a HHV gH polypeptide and a HHV gL polypeptide. For example, the heterodimer can be a non-covalently associated complex between a HHV gH polypeptide and a HHV gL polypeptide. Alternatively, the heterodimer can be a recombinant fusion protein comprising a HHV gH protein joined to a HHV gL protein. The HHV gH protein can be joined to the HHV gL protein with a peptide linker.

As used herein, the term "modified gB polypeptide," refers to a HHV gB polypeptide in which the furin cleavage site in the extracellular domain of the gB polypeptide is replaced by a linker sequence, as described in WO 2015/089340.

The term "operatively linked" means that a promoter, or similar regulatory element, is positioned next to an expressible nucleotide sequence or coding region such that the transcription of that coding region is controlled and regulated by that promoter.

The terms "polypeptide," "peptide," and "protein" are used interchangeably herein to refer to polymers of amino acids.

The term "peptide linker" refers to a short, non-native peptide sequence that links two proteins or fragments of a protein.

The term "recombinant" when used in the context of a nucleic acid means a nucleic acid having nucleotide sequences that are not naturally joined together and can be made by artificially combining two otherwise separated segments of sequence. This artificial combination is often accomplished by chemical synthesis or, more commonly, by the artificial manipulation of isolated segments of nucleic acids, for example, by genetic engineering techniques. Recombinant nucleic acids include nucleic acid vectors comprising an amplified or assembled nucleic acid, which can be used to transform or transfect a suitable host cell. A host cell that comprises the recombinant nucleic acid is referred to as a "recombinant host cell." The gene is then expressed in the recombinant host cell to produce a "recombinant polypeptide." A recombinant nucleic acid can also serve a non-coding function (for example, promoter, origin of replication, ribosome-binding site and the like).

The term "transmembrane domain" (or "TM") means the portion of a polypeptide that naturally and completely traverses the cell membrane, which is a hydrophobic phospholipid bilayer that separates the cytoplasm from the external media in which the host cell resides. Transmembrane domains are typically between about 20 to about 25 amino acids in length, depending on the polypeptide. The transmembrane is typically lipophilic and therefore typically not included in antigenic compositions disclosed herein because it is difficult to express, purify and solubilize.

The term "pharmaceutically acceptable carrier" or "pharmaceutically acceptable excipient" means solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art. In certain embodiments, the pharmaceutically acceptable carrier or excipient is not naturally occurring.

The term "preventing" when used in the context of a disease or disease condition means prophylactic administration of a composition that stops or otherwise delays the onset of a pathological hallmark or symptom of a disease or disorder.

The term "treating" when used in the context of a disease or disease condition means ameliorating, improving or remedying a disease, disorder, or symptom of a disease or condition associated with the disease, or can mean completely or partially stopping, on a molecular level, the biochemical basis of the disease, such as halting replication of a virus, etc.

The term "therapeutically effective amount" when used in the context of an amount of an active agent means an amount that results in an improvement or remediation of the disease, disorder, or symptoms of the disease or condition.

The term "passive transfer" or "passive immunotherapy" or "passive immunity" means obtaining antibodies and/or immune cells from a subject exposed to an antigen and administering those antibodies and/or immune cells to a second subject, thereby providing the second subject with immune protection against challenge with the antigen. Antibodies or immune cells can be transferred in the form of blood, plasma, purified antibodies or immune cells, serum, etc. The second subject may be immunocompromised and/or naïve (never exposed to the antigen). (See, Keller et al., Clin. Microbiol. Rev., 13(4):602-614, 2000).

Human Herpes Viruses. Herpesviridae are subdivided into three subfamilies: alphaherpesvirus, betaherpesvirus, and gammaherpes, based on biological properties and DNA genome similarities (Davison et al., *Antiviral Res.,* 56:1-11, 2002; MacDonald et al., *Am. J. Cardiol.,* 64:359-362, 1989). (See Table 1; Willis et al., *Br. Med. Bull.,* 62(1):125-138, 2002). The alphaherpesviruses include HHV-1, HHV-2, VZV, and pseudorabies virus (PRV), and are neurotropic, i.e., they tend to infect or attack mainly the nervous system of hosts. The alphaherpesvirus family has the broadest host range and spread rapidly in a cell culture. Latent alphaherpesvirus infections are usually established in sensory neurons and lytic infection occurs in epidermal cells (Roizman B, Sears A E. Herpes simplex viruses and their replication. In: Fields B N, Knipe D M, Howley P M, eds. Fields virology. Philadelphia: Lippincott-Raven, 1996:2231-95).

TABLE 1

| Common name | Designation | Sub-family | Genome size (kb pairs) | Site of latency and persistence |
|---|---|---|---|---|
| Herpes simplex virus 1 | Human herpes virus 1 | α | 152 | Neurones (sensory ganglia) |
| Herpes simplex virus 2 | Human herpes virus 2 | α | 152 | Neurones (sensory ganglia) |
| Varicella zoster virus | Human herpes virus 3 | α | 125 | Neurones (sensory ganglia) |
| Epstein-Barr virus | Human herpes virus 4 | γ | 172 | B lymphocytes (oropharyngeal epithelium) |
| Human cytomegalovirus | Human herpes virus 5 | β | 235 | Blood monocytes (probably epithelial cells) |
| | Human herpes virus 6 | β | 170 | Monocytes, T lymphocytes |
| | Human herpes virus 7 | β | 145 | Monocytes, T lymphocytes |
| Kaposi's sarcoma associated herpes virus | Human herpes virus 8 | γ | 230 | Uncertain |

The betaherpesvirus subfamily consists of all cytomegaloviruses including human cytomegalovirus (HCMV, HHV-8), HHV-6, and HHV-7 and are commonly referred to as the roseoloviruses. The betaherpesvirus family has a restricted host range and a long infection cycle. Virus latency of betaherpesvirus is maintained in secretory glands, kidneys and other tissues (Hendrix et al., *Expert Rev. Anti Infect. Ther.,* 5:427-439, 2007).

The gammaherpesvirus subfamily is divided into the Lymphocryptoviruses, which includes EBV, Rhadinovirus, and HHV-8 (KSHV). Gammaherpesviruses have a very narrow host range, and virus replication typically occurs in lymphoblastoid cells but can also lytically infect epithelial cells and fibroblasts. The latent form of gammaherpes virus infection is primarily observed in B and T lymphocytes (Ackerman, *Vet. Microbiol.,* 113:211-222, 2006).

Gammaherpesviruses: Epstein Barr Virus (EBV, HHV-4), and Kaposi's Sarcoma Virus-Associated Herpes (KSHV, HHV-8)

Epstein Barr Virus (EBV, HHV-4). Epstein-Barr virus (EBV) is the first human cancer virus discovered, and it is strongly implicated in the etiology of post-transplant lymphoproliferative disorder (PTLD) and undifferentiated nasopharyngeal carcinoma (NPC). In both instances, the onset and severity of disease is positively correlated with the level of EBV viremia, strongly suggesting a role for lytic EBV re-activation in perpetuating disease. Epstein Barr virus (EBV), also known as human herpesvirus 4 (HHV-4), is a major, global source of morbidity and mortality, responsible for such pathologic entities as Burkitt lymphoma, nasopharyngeal carcinoma, infectious mononucleosis, a subset of Hodgkin's disease, and the lymphoproliferative syndrome in immunosuppressed patients. (Cohen J I, *Curr. Opin. Immunol.,* 1999 August; 11(4):365-70; Thorley-Lawson D A, *J., Allergy Clin. Immunol.,* 2005 August; 116(2):251-61; quiz 62; and Vetsika E K, Callan M., *Expert Rev. Mol. Med.,* 2004 Nov. 5; 6(23):1-16). EBV has a double stranded, linear DNA genome. The nucleotide sequence of the EBV genome and the amino acid sequences of the viral proteins encoded thereby are known and set forth under the NCBI Reference Number NC_009334, Version NC_009334.1, GI:139424470, which sequences are hereby incorporated by reference.

EBV is a member of the gammaherpesvirus subfamily, which is further divided into lymphocryptoviruses, of which KSHV (HHV-8) is also a member. Replication for these family members typically occurs in lymphoblastoid cells, however they can also infect epithelial cells (e.g., nasopharyngeal epithelial cells) and fibroblasts. Latent infection is primarily observed in B and T lymphocytes. (Ackerman, Vet. Microbiol., 113:211-222, 2006).

Post-Transplant Lymphoproliferative Disease (PLTD). Patients undergoing solid organ or stem cell transplantation are at risk of developing post-transplantation lymphoproliferative disorder (PTLD), characterized by uncontrolled EBV-driven B cell proliferation that can evolve into non-Hodgkin lymphoma. (LaCasce, *Oncologist,* 11:674-80, 2006). PTLD may arise from EBV reactivation in seropositive recipients, or from primary EBV infection from the donor allograft, which poses even greater risk. (Dharnidharka et al., *Am. J. Transplant,* 12:976-83, 2012). A similar phenomenon also occurs in patients with AIDS.

Most cases of PTLD involve excessive EBV-driven proliferation of B cells, with a minority (10-15%) of cases being of the NK cell/T cell type (Petrara et al., *Cancer Lett.,* 369(1):37-44, 2015; and Starzl et al., *Lancet,* 1:583-7, 1984). The frequency of PTLD ranges from 1-20% depending on the type of transplant, age of recipient, duration and type of immunosuppressive treatment (Ibrahim et al., *Adv Hematol.,* 2012:230173, 2012; and Smets et al., *Recent Results Cancer Res.,* 193:173-90, 2014). Younger patients, who are EBV seronegative, are at highest risk of developing PTLD following hematopoietic stem cell or solid organ transplantation, due to a lack of prior immunity. Patients with primary immunodeficiency syndromes are also at high risk for developing EBV-driven B cell lymphoproliferation and lymphoma (Rickinson et al., *Trends Immunol.,* 35:159-69, 2014). The WHO defines three major histological types of PTLD of increasing severity: early lesions, polymorphic (P-PTLD), and monomorphic (M-PTLD) (Harris et al., *Semin. Diagn. Pathol.,* 14:8-14, 1997), with the latter typically manifesting as non-Hodgkin lymphoma.

The initial management of PTLD is a reduction in immunosuppression. Additional therapeutic options include B cell-depleting anti-CD20 mAb treatment, anti-viral therapy, intravenous immunoglobulin (IVIg) and interferon (IFN)-γ (LaCasce A S, *Oncologist,* 11:674-80, 2006). Although IVIg in particular has been used empirically in combination with other therapies to treat PTLD, there have been no studies assessing its potential clinical benefit.

Nasopharyngeal carcinoma and EBV. The non-keratinizing variant of squamous cell carcinoma of the nasopharynx (NPC) is endemic in east and southeast Asia and in parts of north and east Africa, and in 2012 accounted for 86,500 cases of cancer worldwide. (Chua et al., *Lancet,* 387(10022):1012-1024, 2016). NPC manifests clinically as epistaxis, unilateral nasal obstruction, auditory complaints, and cranial nerve palsies, with frequent metastasis to cervical lymph nodes. Radiotherapy is the primary treatment for NPC, with additional chemotherapy utilized for more advanced cases. (Id.). 5-year survival is 70-98% depending upon the stage, but NPC has a tendency to recur.

Undifferentiated NPC is invariably associated with EBV, which is believed to play a pathogenic role in tumor development and progression. (Tsang et al., *Virol. Sin.,* 30:107-21, 2015). Establishment of latent EBV infection in pre-malignant nasopharyngeal epithelial cells appears to drive further malignant transformation. Rising levels of serum IgA specific for EBV lytic antigens such as viral capsid antigen and early antigen correlate with progression to NPC. (Ji et al., *Br. J. Cancer,* 96:623-30, 2007). The level of plasma EBV DNA is directly correlated with NPC tumor burden. (To et al.,

*Clin. Cancer Res.*, 9:3254-9, 2003). Thus, latent EBV reactivation is a key feature of NPC formation and progression, suggesting a possible role for antibody-based immunotherapy. Although multiple strains of EBV can be isolated from the blood and saliva of healthy seropositive individuals, only a single strain of EBV is typically isolated from NPC cells, consistent with its pathogenic role. (Tsang et al., *Virol. Sin.*, 30:107-21, 2015). Although strain variations in the sequences of EBNA2, 3A, 3B, and 3C have been described, the envelope proteins gp350, gH/gL, and gB are highly conserved, making these latter proteins ideal vaccine candidates for cross-strain protection. (Sample et al., *J. Virol.*, 64:4084-92, 1990; and Rowe et al., *J. Virol.*, 63:1031-9, 1989).

Circulating EBV DNA copy number is positively correlated with imminent onset of EBV-associated malignancies and clinical severity. EBV qPCR assays are commonly used post-transplantation. (Meerbach et al., *J. Med. Virol.*, 80:441-54, 2008; Tsai et al., *Am. J. Transplant,* 8:1016-24, 2008; Wagner et al., *Transplantation,* 74:656-64, 2002; and van Esser et al., *Blood* 98:972-8, 2001). Elevated EBV DNA in the blood is associated with an increased risk for PTLD, whereas decreases correlate with treatment success. (Baldanti et al., *J. Clin. Microbiol.*, 38:613-9, 2000; Hakim et al., *J. Clin. Microbiol.*, 45:2151-5, 2007; Wagner et al., *Transplantation,* 72:1012-9, 2001; and Clave et al., *Transplantation,* 77:76-84, 2004). Circulating EBV DNA is also positively correlated with adverse survival outcomes in NPC (Jin et al., *Eur. J. Cancer,* 48:882-8, 2012; Hsu et al., *Head Neck,* 34:1064-70, 2012; and Hsu et al., *Oral Oncol.*, 49:620-5, 2013), as well as Hodgkin (Kanakry et al., *Blood,* 121:3547-53, 2013) and extranodal NK/T cell lymphomas, which also linked pathogenically with EBV (Wang et al., *Oncotarget.*, 6(30):30317-30326, 2015).

In the developing world, EBV seroconversion typically occurs in infancy, whereas in developed countries it is more likely contracted in adolescence. Infectious mononucleosis typically occurs only in this latter group (Vetsika et al., *Expert Rev. Mol. Med.*, 2004 Nov. 5; 6(23):1-16). The major human reservoir for latent EBV and EBV transmission is the resting memory B lymphocyte (Babcock et al., Immunity, 1998 September; 9(3):395-404). EBV is dependent upon the gp350-CD21 binding event for viral entry into the B cell (Tanner et al., *Cell,* 1987 Jul. 17; 50(2):203-13; and Tanner et al., *J. Virology,* 1988; 62(12):4452-64), an event that is critical for infectivity and B cell neoplastic transformation (Thorley-Lawson D A, *J. Allergy Clin. Immunol.*, 2005 August; 116(2):251-61; quiz 62). Gp350 is the major EBV outer membrane glycoprotein, while CD21, also known as complement receptor type 2 (CR2), is a receptor on the surface of B cells that binds to iC3b complement protein. Sera from patients with active EBV infection contain antibody that prevent EBV entry into B cells ("neutralizing" antibody). Adsorption of these sera with gp350, eliminates most of this neutralizing activity (Thorley-Lawson et al., J. Virology, 1982 August; 43(2):730-6), indicating that gp350 serves as the major EBV antigen to which a protective hulmoral immune response is directed.

A number of studies have demonstrated that immunization of non-human primates with a subunit gp350 vaccine in adjuvant protects against experimental EBV-induced lymphoma or EBV replication. Thus, purified native gp350, injected into cottontop mannosets (CTM), in association with liposomes, ISCOM's, or muramyl dipeptide, protected against EBV-induced lymphoma. (Morgan et al., *J. Med. Virol.*, 1984; 13(3):281-92; and Morgan et al., *J. Med. Virol.*, 1989 September; 29(1):74-8). Recombinant gp350 in alum or muramyl dipeptide was similarly protective. (Finerty et al., *J. Gen. Virol.*, 1992 February; 73 (Pt 2):449-53; and Finerty et al., Vaccine, 1994 October; 12(13):1180-4). Common marmosets also showed decreased viral replication after EBV challenge following immunization with recombinant gp350 in alum. (Cox et al., *J. Med. Virol.*, 1998 August; 55(4):255-61). Non-human primate studies using gp350 expressed by adenoviral or vaccinia viral vectors have similarly shown protection against experimental EBV-induced lymphoma or EBV replication in CTM or common marmosets. (Mackett et al., *J. Med. Virol.*, 1996 November; 50(3):263-71; Ragot et al., *J. Gen. Virol.*, 1993 March; 74 (Pt 3):501-7; and Morgan et al., *J. Med. Virol.*, 1988 June; 25(2):189-95).

A pilot study in humans has also suggested a potential role for gp350 vaccination in host protection against EBV. In a study by Gu et al. (*Dev. Biol. Stand.*, 1995; 84:171-7) a single dose of gp350/220 expressed by vaccinia virus (VV) was given by scarification to 1- to 3-year-olds who were EBV-seronegative, and VV-seronegative. These children developed neutralizing antibodies to EBV (1:40-1:160). Whereas 10/10 unvaccinated controls became infected at 16 months of follow-up, only 3/9 vaccinated children became infected at this time. More recently, Phase I/II studies were conducted in which healthy EBV-seronegative adults were immunized with a recombinant monomeric gp350 protein in alum+/−monophosphoryl lipid A. (Sokal et al., *J. Infect. Dis.*, 2007 Dec. 15; 196(12):1749-53; and Moutschen et al., *Vaccine,* 2007 Jun. 11; 25(24):4697-705). Following 3 doses, up to 82% of subjects had detectable neutralizing serum anti-gp350 antibody titers. The vaccine demonstrated an efficacy of 78.0% in preventing the development of infectious mononucleosis but not in preventing asymptomatic EBV infection. Finally, an additional phase I trial of recombinant monomeric gp350 protein in alum given to children with chronic kidney disease demonstrated only a minority of subjects developing detectable neutralizing serum anti-gp350 titers. (Rees et al., *Transplantation,* 2009 Oct. 27; 88(8):1025-9).

There is currently no effective immunotherapy for EBV-associated diseases, or a clinically licensed prophylactic EBV vaccine. EBV gp350, gH/gL complex, and gB are three envelope proteins that represent potential vaccine target antigens for EBV. EBV gp350 mediates EBV attachment to B cells through its binding to CD21. EBV gH/gL and gB are involved in mediating EBV fusion and entry into both B cells and epithelial cells.

EBV gp350/gp220. The EBV glycoprotein gp350 and the related splice variant gp220 are responsible for attachment of EBV with high affinity to CR2 on B cells. Antibodies to gp350 or gp220 that block EBV binding neutralize B-cell infection. Each of gp350 and gp220 is a highly glycosylated single-pass membrane protein. As a result of alternative splicing, the viral glycoprotein appears in two forms, with approximate masses of 350 and 220 kDa. The 200 kDa splice form lacks residues 500-757 of the full length gp350. Both gp350 and gp220 retain the CR2 binding domain at the amino terminus. A truncated version of gp350 or gp220 having amino acids 1-470 of gp350 retains the ability to bind CR2 and can inhibit the binding of EBV to CR2 and can be substituted for full length gp350 or gp200 in the compositions described herein or for extracellular domain forms of gp350. (Sarrias et al., *J. Immunol.*, 2001 Aug. 1; 167(3):1490-9). In addition, portions of the gp350 and gp220 protein between amino acids 21-26 or between amino acids 372-378 of the gp350 sequence have been linked to CR2 binding. (Tanner et al., *Cell,* 203-213 (1987), and Nemerow et al., *Cell,* 61:1416-20, 1987). Thus, the term gp350 protein or gp350 antigen (or gp220 protein or antigen) refers to the full length gp350 or gp220 proteins as well as fragments or modified versions thereof that retain the ability to bind the CR2.

The amino acid and nucleic acid sequence of gp350, set forth in GenBank under Accession Number M10593, Version M10593.1, GI 330360, is hereby incorporated by reference. The amino acid sequence of gp350 is (SEQ ID NO: 1):

```
MEAALLVCQY TIQSLIHLTG EDPGFFNVEI PEFPFYPTCN VCTADVNVTI    50
NFDVGGKKHQ LDLDFGQLTP HTKAVYQPRG AFGGSENATN LFLLELLGAG   100
ELALTMRSKK LPINVTTGEE QQVSLESVDV YFQDVFGTMW CHHAEMQNPV   150
YLIPETVPYI KWDNCNSTNI TAVVRAQGLD VTLPLSLPTS AQDSNFSVKT   200
EMLGNEIDIE CIMEDGEISQ VLPGDNKFNI TCSGYESHVP SGGILTSTSP   250
VATPIPGTGY AYSLRLTPRP VSRFLGNNSI LYVFYSGNGP KASGGDYCIQ   300
SNIVFSDEIP ASQDMPTNTT DITYVGDNAT YSVPMVTSED ANSPNVTVTA   350
FWAWPNNTET DFKCKWTLTS GTPSGCENIS GAFASNRTFD ITVSGLGTAP   400
KTLIITRTAT NATTTTHKVI FSKAPESTTT SPTLNTTGFA DPNTTTGLPS   450
STHVPTNLTA PASTGPTVST ADVTSPTPAG TTSGASPVTP SPSPWDNGTE   500
SKAPDMTSST SPVTTPTPNA TSPTPAVTTP TPNATSPTPA VTTPTPNATS   550
PTLGKTSPTS AVTTPTPNAT SPTLGKTSPT SAVTTPTPNA TSPTLGKTSP   600
TSAVTTPTPN ATGPTVGETS PQANATNHTL GGTSPTPVVT SQPKNATSAV   650
TTGQHNITSS STSSMSLRPS SNPETLSPST SDNSTSHMPL LTSAHPTGGE   700
NITQVTPASI STHHVSTSSP EPRPGTTSQA SGPGNSSTST KPGEVNVTKG   750
TPPQNATSPQ APSGQKTAVP TVTSTGGKAN STTGGKHTTG HGARTSTEPT   800
TDYGGDSTTP RPRYNATTYL PPSTSSKLRP RWTFTSPPVT TAQATVPVPP   850
TSQPRFSNLS MLVLQWASLA VLTLLLLLVM ADCAFRRNLS TSHTYTTPPY   900
DDAETYV                                                  907
```

The amino acid sequence of gp220, set forth in GenBank under Accession Number M10593, Version M10593.1, GI 330360, and hereby incorporated by reference, is (SEQ ID NO: 2):

```
MEAALLVCQY TIQSLIHLTG EDPGFFNVEI PEFPFYPTCN VCTADVNVTI    50
NFDVGGKKHQ LDLDFGQLTP HTKAVYQPRG AFGGSENATN LFLLELLGAG   100
ELALTMRSKK LPINVTTGEE QQVSLESVDV YFQDVFGTMW CHHAEMQNPV   150
YLIPETVPYI KWDNCNSTNI TAVVRAQGLD VTLPLSLPTS AQDSNFSVKT   200
EMLGNEIDIE CIMEDGEISQ VLPGDNKFNI TCSGYESHVP SGGILTSTSP   250
VATPIPGTGY AYSLRLTPRP VSRFLGNNSI LYVFYSGNGP KASGGDYCIQ   300
SNIVFSDEIP ASQDMPTNTT DITYVGDNAT YSVPMVTSED ANSPNVTVTA   350
FWAWPNNTET DFKCKWTLTS GTPSGCENIS GAFASNRTFD ITVSGLGTAP   400
KTLIITRTAT NATTTTHKVI FSKAPESTTT SPTLNTTGFA DPNTTTGLPS   450
STHVPTNLTA PASTGPTVST ADVTSPTPAG TTSGASPVTP SPSPWDNGTE   500
STPPQNATSP QAPSGQKTAV PTVTSTGGKA NSTTGGKHTT GHGARTSTEP   550
TTDYGGDSTT PRPRYNATTY LPPSTSSKLR PRWTFTSPPV TTAQATVPVP   600
PTSQPRFSNL SMLVLQWASL AVLTLLLLLV MADCAFRRNL STSHTYTTPP   650
YDDAETYV                                                 658
```

EBV gH, gL, gB, and gp42. The minimal requirement for viral fusion with B cells includes EBV glycoproteins gH, gL, gB, and gp42. For infection of B cells, gp42 binds to the host cell MHC class II molecules to trigger viral cell membrane fusion. On the other hand, for infection of epithelial cells, gp42 is not required. Rather, the EBV gH, gL, and gB proteins are sufficient for viral fusion with epithelial cells. EBV gH/gL exists in certain environments as a noncovalently associated complex.

The amino acid sequence of EBV gH is (SEQ ID NO: 4):

```
MQLLCVFCLV LLWEVGAASL SEVKLHLDIE GHASHYTIPW TELMAKVPGL    50
SPEALWREAN VTEDLASMLN RYKLIYKTSG TLGIALAEPV DIPAVSEGSM   100
QVDASKVHPG VISGLNSPAC MLSAPLEKQL FYYIGTMLPN TRPHSYVFYQ   150
LRCHLSYVAL SINGDKFQYT GAMTSKFLMG TYKRVTEKGD EHVLSLIFGK   200
TKDLPDLRGP FSYPSLTSAQ SGDYSLVIVT TFVHYANFHN YFVPNLKDMF   250
SRAVTMTAAS YARYVLQKLV LLEMKGGCRE PELDTETLTT MFEVSVAFFK   300
VGHAVGETGN GCVDLRWLAK SFFELTVLKD IIGICYGATV KGMQSYGLER   350
LAAVLMATVK MEELGHLTTE KQEYALRLAT VGYPKAGVYS GLIGGATSVL   400
LSAYNRHPLF QPLHTVMRET LFIGSHVVLR ELRLNVTTQG PNLALYQLLS   450
TALCSALEIG EVLRGLALGT ESGLFSPCYL SLRFDLTRDK LLSMAPQEAM   500
LDQAAVSNAV DGFLGRLSLE REDRDAWHLP AYKCVDRLDK VLMIIPLINV   550
TFIISSDREV RGSALYEAST TYLSSSLFLS PVIMNKCSQG AVAGEPRQIP   600
KIQNFTRTQK SCIFCGFALL SYDEKEGLET TTYITSQEVQ NSILSSNYFD   650
FDNLHVHYLL LTTNGTVMEI AGLYEERAHV VLAIILYFIA FALGIFLVHK   700
IVMFFL                                                   706
```

The amino acid sequence of EBV gL is (SEQ ID NO: 5):

```
MRTVGVFLAT CLVTIFVLPT WGNWAYPCCH VTQLRAQHLL ALENISDIYL    50
VSNQTCDGFS LASLNSPKNG SNQLVISRCA NGLNVVSFFI SILKRSSSAL   100
TGHLRELLTT LETLYGSFSV EDLFGANLNR YAWHRGG                 137
```

The amino acid sequence of EBV gB is (SEQ ID NO: 6):

```
MTRRRVLSVV VLLAALACRL GAQTPEQPAP PATTVQPTAT RQQTSFPFRV    50
CELSSHGDLF RFSSDIQCPS FGTRENHTEG LLMVFKDNII PYSFKVRSYT   100
KIVTNILIYN GWYADSVTNR HEEKFSVDSY ETDQMDTIYQ CYNAVKMTKD   150
GLTRVYVDRD GVNITVNLKP TGGLANGVRR YASQTELYDA PGWLIWTYRT   200
RTTVNCLITD MMAKSNSPFD FFVTTTGQTV EMSPFYDGKN KETFHERADS   250
FHVRTNYKIV DYDNRGTNPQ GERRAFLDKG TYTLSWKLEN RTAYCPLQHW   300
QTFDSTIATE TGKSIHFVTD EGTSSFVTNT TVGIELPDAF KCIEEQVNKT   350
MHEKYEAVQD RYTKGQEAIT YFITSGGLLL AWLPLTPRSL ATVKNLTELT   400
TPTSSPPSSP SPPAPPAARG STSAAVLRRR RRDAGNATTP VPPAAPGKSL   450
GTLNNPATVQ IQFAYDSLRR QINRMLGDLA RAWCLEQKRQ NMVLRELTKI   500
NPTTVMSSIY GKAVAAKRLG DVISVSQCVP VNQATVTLRK SMRVPGSETM   550
CYSRPLVSFS FINDTKTYEG QLGTDNEIFL TKKMTEVCQA TSQYYFQSGN   600
EIHVYNDYHH FKTIELDGIA TLQTFISLNT SLIENIDFAS LELYSRDEQR   650
ASNVFDLEGI FREYNFQAQN IAGLRKDLDN AVSNGRNQFV DGLGELMDSL   700
GSVGQSITNL VSTVGGLFSS LVSGFISFFK NPFGGMLILV LVAGVVILVI   750
```

-continued

```
SLTRRTRQMS QQPVQMLYPG IDELAQQHAS GEGPGINPIS KTELQAIMLA   800

LHEQNQEQKR AAQRAAGPSV ASRALQAARD RFPGLRRRRY HDPETAAALL   850

GEAETEF                                                  857
```

The amino acid sequence of EBV gp42 is (SEQ ID NO: 7):

```
MVSFKQVRVP LFTAIALVIV LLLAYFLPPR VRGGGRVSAA AITWVPKPNV    50

EVWPVDPPPP VNFNKTAEQE YGDKEIKLPH WTPTLHTFQV PKNYTKANCT   100

YCNTREYTFS YKERCFYFTK KKHTWNGCFQ ACAELYPCTY FYGPTPDILP   150

VVTRNLNAIE SLWVGVYRVG EGNWTSLDGG TFKVYQIFGS HCTYVSKFST   200

VPVSHHECSF LKPCLCVSQR SNS                                223
```

The amino acid sequence of EBV BMRF-2 is (SEQ ID NO: 8):

```
MFSCKQHLSL GACVFCLGLL ASTPFIWCFV FANLLSLEIF SPWQTHVYRL    50

GFPTACLMAV LWTLVPAKHA VRAVTPAIML NIASALIFFS LRVYSTSTWV   100

SAPCLFLANL PLLCLWPRLA IEIVYICPAI HQRFFELGLL LACTIFALSV   150

VSRALEVSAV FMSPFFIFLA LGSGSLAGAR RNQIYTSGLE RRRSIFCARG   200

DHSVASLKET LHKCPWDLLA ISALTVLVVC VMIVLHVHAE VFFGLSRYLP   250

LFLCGAMASG GLYLGHSSII ACVMATLCTL TSVVVYFLHE TLGPLGKTVL   300

FISIFVYYFS GVAALSAAMR YKLKKFVNGP LVHLRVVYMC CFVFTFCEYL   350

LVTFIKS
```

The amino acid sequence of EBV BDLF2 is (SEQ ID NO: 9):

```
MVDEQVAVEH GTVSHTISRE EDGVVHERRV LASGERVEVF YKAPAPRPRE    50

GRASTFHDFT VPAAAAVPGP EPEPEPHPPM PIHANGGGET KTNTQDQNQN   100

QTTRTRTNAK AEERTAEMDD TMASSGGQRG APISADLLSL SSLTGRMAAM   150

APSWMKSEVC GERMRFKEDV YDGEAETLAE PPRCFMLSFV FIYYCCYLAF   200

LALLAFGFNP LFLPSFMPVG AKVLRGKGRD FGVPLSYGCP TNPFCKVYTL   250

IPAVVINNVT YYPNNTDSHG GHGGFEAAAL HVAALFESGC PNLQAVTNRN   300

RTFNVTRASG RVERRLVQDM QRVLASAVVV MHHHCHYETY YVFDGVGPEF   350

GTIPTPCFKD VLAFRPSLVT NCTAPLKTSV KGPNWSGAAG GMKRKQCRVD   400

RLTDRSFPAY LEEVMYVMVQ
```

The antigenic compositions and methods of this application typically involve two or more HHV proteins involved in mediating HHV binding, fusion, and entry into host cells. In certain embodiments, two or more EBV proteins disclosed herein are combined in an antigenic composition. The two or more EBV proteins can be administered simultaneously or separately to induce an immune response or to treat or prevent an EBV infection in a subject. In certain embodiments, the antigenic composition (or method of administration) comprises two or more of the following EBV polypeptides (or nucleic acids encoding the same): gB, gH, gL, and gp350. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer. In some embodiments, the gp350 polypeptides are monomeric, dimeric, trimeric, or tetrameric.

In certain embodiments, the two or more EBV proteins (or nucleic acids encoding the same) comprise a monomeric or multimeric gp350 and monomeric or multimeric gB. In certain embodiments, the gp350 is monomeric or tetrameric and the gB is monomeric or trimeric. In certain embodiments, the gp350 is monomeric and the gB is trimeric. In certain embodiments, the gp350 is tetrameric and the gB is trimeric.

In certain embodiments, the two or more EBV proteins (or nucleic acids encoding the same) comprise a monomeric or multimeric gp350 and a monomeric or multimeric gH/gL heterodimer. In certain embodiments, the gp350 is monomeric or tetrameric and the gH/gL heterodimer is monomeric or trimeric. In certain embodiments, the gp350 is monomeric and the gH/gL heterodimer is monomeric. In certain embodiments, the gp350 is tetrameric and the gH/gL heterodimer is trimeric.

In certain embodiments, the two or more EBV proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is monomeric and the gH/gL heterodimer is monomeric or trimeric. In certain embodiments, the gB is trimeric and the gH/gL heterodimer is monomeric. In certain embodiments, the gB is trimeric and the gH/gL heterodimer is trimeric. In certain embodiments, the EBV gB, gH, and gL polypeptides form a protein complex when mixed together. In certain embodiments, the EBV gB, gH, and gL polypeptides are not administered as a protein complex comprising the gB, gH, and gL polypeptides. For example, the gB can be administered separately from the gH and/or gL or administered with the gH and gL but not as a protein complex.

In certain embodiments, the two or more EBV proteins (or nucleic acids encoding the same) comprise a monomeric or multimeric gp350, a monomeric or multimeric gB and a monomeric or multimeric gH/gL heterodimer. In certain embodiments, the gp350 is monomeric or tetrameric, the gB is monomeric or trimeric and the gH/gL heterodimer is monomeric or trimeric. In certain embodiments, the gp350 is monomeric, the gB is trimeric and the gH/gL heterodimer is monomeric. In certain embodiments, the gp350 is tetrameric, the gB is trimeric and the gH/gL heterodimer is trimeric.

In some embodiments, the two or more EBV proteins further comprises one or more of a BMRF-2 polypeptide, a BDLF2 polypeptide, and/or a gp42 polypeptide, which can be monomeric or multimeric (e.g., dimeric, trimeric, or tetrameric).

Kaposi's Sarcoma Virus-Associated Herpes (KSHV, HHV-8). The two human gamma herpesviruses, Epstein-Barr virus (EBV), a gamma 1 lymphocryptovirus, and Kaposi's sarcoma associated virus (KSHV), a gamma 2 rhadinovirus, have many features in common. They share an architecture that is typical of all members of the herpesvirus family, they share an ability to establish latency in lymphocytes, and they are both initiators or potentiators of human tumors. (Chandran et al., Human Herpesviruses: Biology, Therapy, and Imunoprophylaxis, Eds. Arvin, A., Campadelli-Fiume, G., and Mocarski E., et al., Cambridge University Press, 2007, Ch. 23). KSHV broadly infects many types of host cells, including B-cells from the peripheral blood, B-cells in primary effusion lymphomas (PEL) or body-cavity based B-cell lymphomas (BCBL) and multicentric Cattleman's disease (MCD), flat endothelial cells lining the vascular spaces of Kaposi's sarcoma (KS) lesions, typical KS spindle cells, CD 45+/CD68+ monocytes in KS lesions, keratinocytes, and epithelial cells. (Id.). Further, KSHV infection has been associated with multiple myeloma. (Rettig et al., *Science,* 276:1851-4, 1997). Like EBV, KSHV also expresses gB, gH, and gL that mediate cell fusion and entry. KSHV also expresses the conserved glycoproteins, gM and gN, which mediate similar, if not identical, roles as compared to their EBV counterparts. (Id.).

However, the gp350 glycoprotein of EBV is replaced in KSHV with a polypeptide termed K8.1. The K8.1 gene encodes a 197-amino acid with a predicted molecular weight of about 22 kDa and possessing no sequence corresponding to a TM domain. Similar to the EBV gp350/220, the KSHV K8.1 gene encodes two ORF s, designated gpK8.1A and gpK8.1B, from spliced messages. The larger cDNA is 752 bp long (76,214-76,941 bp) and utilizes the polyadenylation signal sequence (AATAAA) at position 77 013 bp. The 228-aa long encoded protein is designated gpK8.1A, which contains a signal sequence, transmembrane domain, and four N-glycosylation sites. Otherwise, the KSHV gpK18.1 polypeptide performs similar functions as reported for EBV gp350, forming a complex with gB and binding to a cell surface heparin sulfate molecule on the host cell.

KSHV ORF68 is a late lytic, delayed early structural and assembly gene encoding a transmembrane glycoprotein that is a component of the KSHV envelope. (Nakamura et al., *J. Virol.,* 77(7):4205-20, 2003; and Jha et al., *mBio,* 5(6): e02261-14, 2014; and Stirzl et al., *Thromb. Haemost.,* 102: 1117-34, 2009). ORF68 is known to interact with and inhibit the host cell's ubiquitin proteasome pathway, thereby inhibiting protein degradation. (Gardner, M., $8^{th}$ Annual CEND Symposium, 22 Mar. 2016). ORF68 is essential for viral genome replication in KSHV. It is postulated that KSHV ORF68 encodes a protein that suppresses the proteasome-mediated degradation of a protein in the cytoplasm of the host cell that is essential for KSHV DNA replication. (Id.).

The antigenic compositions and methods of this application typically involve two or more HHV proteins involved in mediating HHV binding, fusion, and entry into host cells. In certain embodiments, two or more KSHV proteins disclosed herein are combined in an antigenic composition. The two or more KSHV proteins can be administered simultaneously or separately to induce an immune response or to treat or prevent a KSHV infection in a subject. In certain embodiments, the antigenic composition (or method of administration) comprises two or more of the following KSHV polypeptides (or nucleic acids encoding the same): gB, gH, and gL. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer.

In certain embodiments, the two or more KSHV proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is monomeric and the gH/gL heterodimer is monomeric or trimeric. In certain embodiments, the gB is trimeric and the gH/gL heterodimer is monomeric. In certain embodiments, the gB is trimeric and the gH/gL heterodimer is trimeric. In certain embodiments, the KSHV gB, gH, and gL polypeptides form a protein complex when mixed together. In certain embodiments, the KSHV gB, gH, and gL polypeptides are not administered as a protein complex comprising the gB, gH, and gL polypeptides. For example, the gB can be administered separately from the gH and/or gL or administered with the gH and gL but not as a protein complex.

In certain embodiments, the two or more KSHV proteins further comprises one or more of the gN polypeptide, the gM polypeptide, the ORF68 polypeptide and/or the gpK8.1 polypeptide, which can be monomeric or multimeric (e.g., dimeric, trimeric, or tetrameric).

The amino acid and nucleic acid sequence of KSHV gpK8.1A, set forth in GenBank under Accession Number AAC63270.1, GI 3414867, is hereby incorporated by reference. The amino acid sequence of gpK8.1 is (SEQ ID NO: 10):

```
  1 MSSTQIRTEI PVALLILCLC LVACHANCPT YRSHLGFWQE GWSGQVYQDW LGRMNCSYEN

 61 MTALEAVSLN GTRLAAGSPS SEYPNVSVSV EDTSASGSGE DAIDESGSGE EERPVTSHVT

121 FMTQSVQATT ELTDALISAF SGSYSSGEPS RTTRIRVSPV AENGRNSGAS NRVPFSATTT

181 TTRGRDAHYN AEIRTHLYIL WAVGLLLGLV LILYLCVPRC RRKKPYIV
```

The amino acid and nucleic acid sequence of KSHV gpK8.1B, set forth in GenBank under Accession Number AJE29698.1, GI 748016404, and hereby incorporated by reference. The amino acid sequence of gpK8.1B is (SEQ ID NO: 11):

```
  1 MSSTQIRTEI PVALLILCLC LVACHANCPT YRSHLGFWQE GWSGQVYQDW LGRMNCSYEN

 61 MTALEAVSLN GTRLAAGSPS RSYSSGEPSR TTRIRVSPVA ENGRNSGASN RVPFSATTTT

121 TRGRDAHYNA EIRTHLYILW AVGLLLGLVL ILYLCVPRCR RKKPYIV
```

The amino acid sequence of KSHV gH is (SEQ ID NO: 12):

```
MQGLAFLAAL ACWRCISLTC GATGALPTTA TTITRSATQL INGRTNLSIE    50

LEFNGTSFFL NWQNLLNVIT EPALTELWTS AEVAEDLRVT LKKRQSLFFP   100

NKTVVISGDG HRYTCEVPTS SQTYNITKGF NYSALPGHLG GFGINARLVL   150

GDIFASKWSL FARDTPEYRV FYPMNVMAVK FSISIGNNES GVALYGVVSE   200

DFVVVTLHNR SKEANETASH LLFGLPDSLP SLKGHATYDE LTFARNAKYA   250

LVAILPKDSY QTLLTENYTR IFLNMTESTP LEFTRTIQTR IVSIEARRAC   300

AAQEAAPDIF LVLFQMLVAH FLVARGIAEH RFVEVDCVCR QYAELYFLRR   350

ISRLCMPTFT TVGYNHTTLG AVAATQIARV SATKLASLPR SSQETVLAMV   400

QLGARDGAVP SSILEGIAMV VEHMYTAYTY VYTLGDTERK LMLDIHTVLT   450

DSCPPKDSGV SEKLLRTYLM FTSMCTNIEL GEMIARFSKP DSLNIYRAFS   500

PCFLGLRYDL HPAKLRAEAP QSSALTRTAV ARGTSGFAEL LHALHLDSLN   550

LIPAINCSKI TADKIIATVP LPHVTYIISS EALSNAVVYE VSEIFLKSAM   600

FISAIKPDCS GFNFSQIDRH IPIVYNISTP RRGCPLCDSV IMSYDESDGL   650

QSLMYVTNER VQTNLFLDKS PFFDNNNLHI HYLWLRDNGT VVEIRGMYRR   700

RAASALFLIL SFIGFSGVIY FLYRLFSILY
```

The amino acid sequence of KSHV gL is (SEQ ID NO: 13):

```
MGIFALFAVL WTTLLVTSHA YVALPCCAIO ASAASTLPLF FAVHSIHFAD    50

PNHCNGVCIA KLRSKTGDIT VETCVNGFNL RSFLVAVVRR LGSWASQENL   100

RLLWYLQRSL TAYTVGFNAT TADSSIHNVN IIIISVGKAM NRTGSVSGSQ   150

TRAKSSSRRA HAGOKGK
```

The amino acid sequence of KSHV gB is (SEQ ID NO: 12):

```
MQGLAFLAAL ACWRCISLTC GATGALPTTA TTITRSATQL INGRTNLSIE    50

LEFNGTSFFL NWQNLLNVIT EPALTELWTS AEVAEDLRVT LKKRQSLFFP   100
```

-continued

```
NKTVVISGDG HRYTCEVPTS SQTYNITKGF NYSALPGHLG GEGINARLVL   150
GDIFASKWSL FARDTPEYRV FYPMNVMAVK FSISIGNNES GVALYGVVSE   200
DFVVVTLHNR SKEANETASH LLFGLPDSLP SLKGHATYDE LTFARNAKYA   250
LVAILPKDSY QTLLTENYTR IFLNMTESTP LEFTRTIQTR IVSIEARRAC   300
AAQEAAPDIF LVLFQMLVAH FLVARGIAEH RFVEVDCVCR QYAELYFLRR   350
ISRLCMPTFT TVGYNHTTLG AVAATQIARV SATKLASLPR SSQETVLAMV   400
QLGARDGAVP SSILEGIAMV VEHMYTAYTY VYTLGDTERK LMLDIHTVLT   450
DSCPPKDSGV SEKLLRTYLM FTSMCTNIEL GEMIARFSKP DSLNIYRAFS   500
PCFLGLRYDL HPAKLRAEAP QSSALTRTAV ARGTSGFAEL LHALHLDSLN   550
LIPAINCSKI TADKIIATVP LPHVTYIISS EALSNAVVYE VSEIFLKSAM   600
FISAIKPDCS GFNFSQIDRH IPIVYNISTP RRGCPLCDSV IMSYDESDGL   650
QSLMYVTNER VQTNLFLDKS PFFDNNNLHI HYLWLRDNGT VVEIRGMYRR   700
PAASALFLIL SFIGFSGVIY FLYRLFSILY
```

The amino acid sequence of KSHV gN is (SEQ ID NO: 14):

```
MTASTVALAL FVASILGHCW VTANSTGVAS STERSSPSTA GLSARPSPGP    50
TSVTTPGFYD VACSADSFSP SLSSFSSVWA LINALLVVVA TFFYLVYLCF   100
FKFVDEVVHA
```

The amino acid sequence of KSHV gM is (SEQ ID NO: 15):

```
MRASKSDRFL MSSWVKLLFV AVIMYICSAV VPMAATYEGL GFPCYFNNLV    50
NYSALNLTVR NSAKHLTPTL FLEKPEMLVY IFWTFIVDGI AIVYYCLAAV   100
AVYRAKHVHA TTMMSMQSWI ALLGSHSVLY VAILRMWSMQ LFIHVLSYKH   150
VLMAAFVYCI HFCISFAHIQ SLITCNSAQW EIPLLEQHVP DNTMMESLLT   200
RWKPVCVNLY LSTTALEMLL FSLSTMMAVG NSFYVLVSDA IFGAVNMFLA   250
LTVVWYINTE FFLVKFMRRQ VGFYVGVFVG YLILLLPVIR YENAFVQANL   300
HYIVAININISC IPILCILAIV IRVIRSDWGL CTPSAAYMPL ATSAPTVDRT   350
PTVHQKPPPL PAKTRARAKV KDISTPAPRT QYQSDHESDS EIDETQMIFI   400
```

The amino acid sequence of KSHV ORF68 is (SEQ ID NO: 16):

```
MFVPWQLGTI TRHRDELQKL LAASLLPEHP EESLGNPIMT QIHQSLQPSS    50
PCRVCQLLFS LVRDSSTPMG FFEDYACLCF FCLYAPHCWT STMAAAADLC   100
EIMHLHFPEE EATYGLFGPG RLMGIDLQLH FFVQKCFKTT AAEKILGISN   150
LQFLKSEFIR GMLTGTITCN FCFKTSWPRT DKEEATGPTP CCQITDTTTA   200
PASGIPELAR ATFCGASRPT KPSLLPALID IWSTSSELLD EPRPRLIASD   250
MSELKSVVAS HDPFFSPPLQ ADTSQGPCLM HPTLGLRYKN GTASVCLLCE   300
CLAAHPEAPK ALQTLQCEVM GHIENNVKLV DRIAFVLDNP FAMPYVSDPL   350
LRELIRGCTP QEIHKHLFCD PLCALNAKVV SEDVLFRLPR EQEYKKLRAS   400
```

-continued

```
AAAGQLLDAN TLFDCEVVQT LVFLFKGLQN ARVGKTTSLD IIRELTAQLK   450

RHRLDLAHPS QTSHLYA
```

Betaherpesviruses: Human Cytomegalovirus (HCMV, HHV-5); Human Herpes Virus 6 (HHV-6); & Human Herpes Virus 7 (HHV-7)

Human Cytomegalovirus (HCMV, HHV-5). Human cytomegalovirus (HCMV) is an enveloped, double-stranded DNA Q-herpesvirus of the Herpesviridae family. HCMV further belongs to the betaherpesvirus subfamily, of which HHV-6 and HHV-7 are also members. Cells infected with this family of viruses often become enlarged (cytomegaly). HCMV is the leading non-genetic cause of hearing loss in childhood and a significant cause of neurodevelopmental delay, including mental retardation. (Demmler-Harrison G J, *J. Clin. Virol.,* 46 Suppl 4, 2009: S1-5; Jeon et al., *Infect. Dis. Obstet. Gynecol.,* 2006:80383, 2006; and Morton et al., *N. Engl. J. Med.,* 354:2151-64, 2006). In the U.S., between 20,000 and 40,000 infants per year are born with HCMV infection, accounting for an annual 8,000 permanent disabilities and a healthcare cost of $1.86 billion. HCMV also causes significant clinical diseases in immunosuppressed individuals, including transplant recipients and patients with AIDS. (Bonaros et al., *Clin. Transplant.,* 22:89-97, 2008; and Steininger et al., *J. Clin. Virol.,* 37:1-9, 2006). Although HCMV infection in immunocompetent individuals is generally asymptomatic, it may produce a mononucleosis syndrome in 10% of primary infections of older children and adults. (Horwitz et al., Medicine (Baltimore), 65:124-34, 1986). In 2001, the Institute of Medicine of the U.S. National Academy of Sciences stated that a vaccine to prevent congenital HCMV infection is among the highest U. S. priorities. (Stratton et al., "Vaccines for the 21st Century: A tool for decision making," Washington, DC, National Academy Press, 2001).

HCMV is spread mainly through saliva and urine, and via transplacental transmission to the fetus (Krause et al., *Vaccine,* 32:4-10, 2014). HCMV can also be transmitted to infants through breast milk (Maschmann et al., *Clin. Infect. Dis.,* 33:1998-2003, 2001), through sexual activity, through solid organ or hematopoietic stem cell transplantation, and rarely by transfusion of blood products. HCMV primarily infects fibroblasts, epithelial cells, endothelial cells, monocyte-macrophages, hepatocytes, and neurons. The mechanism of HCMV fusion and entry into mammalian cells is analogous to that employed by other members of the herpesvirus family (Heldwein et al., *Cell. Mol. Life Sci.,* 65:1653-68, 2008; and White et al., *Crit. Rev. Biochem. Mol. Biol.,* 43:189-219, 2008). HCMV enters cells by fusing its envelope with either the plasma membrane (fibroblasts) (Compton et al., *Virology,* 191:387-95, 1992) or endosomal membrane (epithelial and endothelial cells) (Ryckman et al., *J. Virol.,* 80:710-22, 2006).

HCMV gB, gH, gL, gO (UL74), gM, gN (gpUL73), and UL12811301131A. The nine glycoproteins gB, gH, gL, gO (UL74), gM, gN (gpUL73), and UL128/130/131A, have collectively been identified as the envelope glycoproteins that play important roles in HCMV fusion and entry into host cells (Hahn et al., *J. Virol.,* 78:10023-33, 2004; Ryckman et al., *J. Virol.,* 82:60-70, 2008; Wang et al., *Proc. Natl. Acad. Sci. USA,* 102:18153-8, 2005; and Wille et al., *J. Virol.,* 84:2585-96, 2010). Similar to gammaherpesvirus family members, HCMV gH/gL and gB proteins play an important role in HCMV fusion and entry into host cells. The gB protein is the direct mediator of HCMV fusion with all host cell membranes. Activation of HCMV gB and its fusogenic activity requires association with gH/gL and gO, which together form a gH/gL/gO heterotrimer protein complex. However, the gH/gL/UL128/130/131A (pentameric complex) protein is also important for efficient targeting of HCMV to epithelial and endothelial cells, since UL128/130/131A mutants failed to infect these cells (Ryckman et al., *J. Virol.,* 80:710-22, 2006; Hahn et al., *J. Virol.,* 78:10023-33, 2004; Adler et al., *J. Gen. Virol.,* 87: 2451-60, 2006; and Wang et al., *J. Virol.,* 79:10330-8, 2005). In contrast, gO seems to be involved in HCMV fusion with all HCMV host cells, since gO null HCMV failed to infect all cell types tested including fibroblasts, epithelial and endothelial cells, and infection of both fibroblasts and epithelial cells was generally correlated with the abundance of gH/gL/gO complex, but not with pentameric complex gH/gL/UL128/UL130/UL131A (Wille et al., *J. Virol.,* 84:2585-96, 2010; Jiang et al., *J. Virol.,* 82:2802-12, 2008; and Zhou et al., *J. Virol.,* 89(17):8999-9009, 2015). All three of the UL128-131 genes share a common architecture including an amino-terminal signal peptide, a central chemokine-like domain, and a carboxy-terminal domain with no homology to any known class of proteins. (Patrone et al., *J. Virol.,* 79(13): 8361-8373, 2005). HCMV gB or gH/gL proteins have been shown to elicit serum HCMV neutralizing antibodies for both fibroblasts and epithelial cells. However, the pentameric complex induces the highest serum neutralizing titers for epithelial and endothelial cells, though with no further improvement for fibroblasts (Wen et al., *Vaccine,* 32:3796-804, 2014; Freed et al., *Proc. Natl. Acad. Sci. USA,* 110: E4997-5005, 2013; and Schuessler et al., *J. Virol.,* 86:504-12, 2012). Although an HCMV gH/gL/gO complex was produced in mammalian cells (HEK-239) (Kinzler et al., *J. Clin. Virol.,* 25 Suppl 2:S87-95, 2002), there have been no reports on its ability to induce HCMV neutralizing antibodies.

The glycoprotein M and N polypeptides are glycoprotein complex II (GCII) antigens. Glycoprotein N is an envelope component of the mature viral particle with a portion exposed at the virus surface and a portion extending to the internal side of the envelope. It is present in the matrix of defense bodies and "block holes." (Pignatelli, et al., *Arch. Virol.,* 147:1247, 2002). HCMV gM polypeptide is 372 amino acids in length and has an approximate molecular weight of 42 kDa, possessing seven TM domains. HCMV gN is 129 amino acids in length and has a predicted molecular weight of about 15 kDa, but due to heavy glycosylation tends to appear as a 40 to 50 kDa protein. The glycoprotein M (gM, UL100) and glycoprotein N (gN, UL73) form a gM/gN protein complex which is the most abundant protein component of the HCMV envelope. Recent studies have indicated that deletion of the viral gene encoding either gM or gN is lethal for HCMV, but not for other HHV. (Baines et al., *J. Virol.,* 67:1441-1452, 1993; Fuchs et al., *Virus Res.,* 112:108-114, 2005; Hobom et al., *J. Virol.,* 74:7720-7729, 2000; Mach et al., *J. Virol.,* 81:5212-5224, 2007; and MacLean et al., *J. Gen. Virol.,* 74(pt. 6):975-983, 1993).

The antigenic compositions and methods of this application typically involve two or more HHV proteins involved in mediating HHV binding, fusion, and entry into host cells. In certain embodiments, two or more HCMV proteins disclosed herein are combined in an antigenic composition. The two or more HCMV proteins can be administered simultaneously or separately to induce an immune response or to treat or prevent an HCMV infection in a subject. In certain embodiments, the antigenic composition (or method of administration) comprises two or more of the following HCMV polypeptides (or nucleic acids encoding the same): gB, gH, and gL. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer.

In certain embodiments, the two or more HCMV proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is monomeric and the gH/gL heterodimer is monomeric or trimeric. In certain embodiments, the gB is trimeric and the gH/gL heterodimer is monomeric. In certain embodiments, the gB is trimeric and the gH/gL heterodimer is trimeric. In certain embodiments, the HCMV gB, gH, and gL polypeptides form a protein complex when mixed together. In certain embodiments, the HCMV gB, gH, and gL polypeptides are not administered as a protein complex comprising the gB, gH, and gL polypeptides. For example, the gB can be administered separately from the gH and/or gL or administered with the gH and gL but not as a protein complex.

In some embodiments, the two or more HCMV proteins (or nucleic acids encoding the same) further comprises the gO polypeptide, which is optionally multimeric (e.g., dimeric, trimeric, or tetrameric). In other embodiments, the two or more HCMV proteins (or nucleic acids encoding the same) further comprises a gN and/or a gM polypeptide, which can be monomeric or multimeric (e.g., dimeric, trimeric, or tetrameric). In still other embodiments, the two or more HCMV proteins (or nucleic acids encoding the same) comprise the gB polypeptide, the gH polypeptide, the gL polypeptide, and the UL128, UL130, and UL131A polypeptides. In certain embodiments, the two or more HCMV proteins (or nucleic acids encoding the same) comprise trimeric gB, monomeric gH/gL and UL128, UL130, and UL131A, wherein UL128, UL130, and UL131A are preferably combined as a fusion protein. In certain embodiments, these five HCMV polypeptides are present in the composition as a pentameric protein complex. In certain embodiments, they are present in the composition as a fusion protein.

Figure 13:
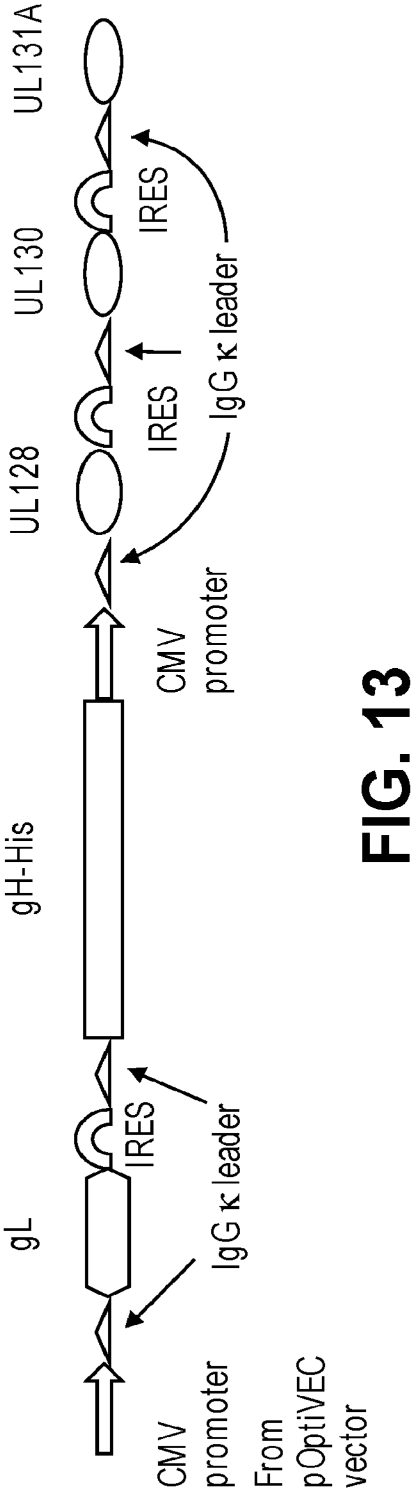
FIG. 13 shows a schematic diagram of a non-limiting DNA construct for expression of the pentameric complex gH/gL/UL128/UL130/UL131A.

Also disclosed is a recombinant nucleic acid encoding a protein complex or a fusion protein comprising HHV polypeptides gH, gL, UL128, UL130, and UL131A. The sequences of these HHV polypeptides making up the pentameric complex can be from any betaherpesvirus subfamily member, including, for example, HCMV. An embodiment of a nucleic acid construct encoding all five HCMV polypeptides of the pentameric complex is depicted in FIG. 13, including exemplary operably linked promoter sequences and the like. Additional nucleic acid sequences can be included in such a nucleic acid sequence to aide in purification, such as his-tag sequences or immunoglobulin kappa sequences, etc. known in the art as protein purification tags, etc. In another embodiment, the nucleic acid construct can comprise sequences encoding the HHV polypeptides gH, gL, and gB. These highly conserved polypeptides are found in all HHV genomes and therefore can correspond to any known HHV gB, gH, and/or gL sequence.

The amino acid sequence of HCMV gH is (SEQ ID NO: 17):

```
MRPGLPPYLT VFTVYLLSHL PSQRYGADAA SEALDPHAFH LLLNTYGRPI  50
RFLRENTTQC TYNSSLRNST VVRENAISFN FFQSYNQYYV FHMPRCLFAG 100
PLAEQFLNQV DLTETLERYQ QRLNTYALVS KDLASYRSFS QQLKAQDSLG 150
QQPTTVPPPI DLSIPHVWMP PQTTPHDWKG SHTTSGLHRP HFNQTCILFD 200
GHDLLFSTVT PCLHQGFYLM DELRYVKITL TEDFFVVTVS IDDDTPMLLI 250
FGHLPRVLFK APYQRDNFIL RQTEKHELLV LVKKAQLNRH SYLKDSDFLD 300
AALDFNYLDL SALLRNSFHR YAVDVLKSGR CQMLDRRTVE MAFAYALALF 350
AAARQEEAGT EISIPRALDR QAALLQIQEF MITCLSQTPP RTTLLLYPTA 400
VDLAKRALWT PDQITDITSL VRLVYILSKQ NQQHLIPQWA LRQIADFALQ 450
LHKTHLASFL SAFARQELYL MGSLVHSMLV HTTERREIFI VETGLCSLAE 500
LSHFTQLLAH PHHEYLSDLY TPCSSSGRRD HSLERLTRLF PDATVPATVP 550
AALSILSTMQ PSTLETFPDL FCLPLGESFS ALTVSEHVSY VVTNQYLIKG 600
ISYPVSTTVV GQSLIITQTD SQTKCELTRN MHTTHSITAA LNISLENCAF 650
CQSALLEYDD TQGVINIMYM HDSDDVLFAL DPYNEVVVSS PRTHYLMLLK 700
NGTVLEVTDV VVDATDSRLL MMSVYALSAI IGIYLLYRML KTC
```

The amino acid sequence of HCMV gL is (SEQ ID NO: 18):

```
MCRRPDCGFS FSPGPVILLW CCLLLPIVSS AAVSVAPTAA EKVPAECPEL    50
TRRCLLGEVF EGDKYESWLR PLVNVTGRDG PLSQLIRYRP VTPEAANSVL   100
LDEAFLDTLA LLYNNPDQLR ALLTLLSSDT APRWMTVMRG YSECGDGSPA   150
VYTCVDDLCR GYDLTRLSYG RSIFTEHVLG FELVPPSLFN VVVAIRNEAT   200
RTNRAVRLPV STAAAPEGIT LFYGLYNAVK EFCLRHQLDP PLLRHLDKYY   250
AGLPPELKQT RVNLPAHSRY GPQAVDAR
```

The amino acid sequence of HCMV gB is (SEQ ID NO: 19):

```
MESRIWCLVV CVNLCIVCLG AAVSSSSTSH ATSSTHNGSH TSRTTSAQTR  50
SVYSQHVTSS EAVSHRANET IYNTTLKYGD VVGVNTTKYP YRVCSMAQGT 100
DLIRFERNII CTSMKPINED LDEGIMVVYK RNIVAHTFKV RVYQKVLTFR 150
RSYAYIYTTY LLGSNTEYVA PPMWEIHHIN KFAQCYSSYS RVIGGTVFVA 200
YHRDSYENKT MQLIPDDYSN THSTRYVTVK DQWHSRGSTW LYRETCNLNC 250
MLTITTARSK YPYHFFATST GDVVYISPFY NGTNRNASYF GENADKFFIF 300
PNYTIVSDFG RPNAAPETHR LVAFLERADS VISWDIQDEK NVTCQLTFWE 350
ASERTIRSEA EDSYHFSSAK MTATELSKKQ EVNMSDSALD CVRDEAINKL 400
QQIFNTSYNQ TYEKYGNVSV FETSGGLVVF WQGIKQKSLV ELERLANRSS 450
LNITHRTRRS TSDNNTTHLS SMESVHNLVY AQLQFTYDTL RGYINRALAQ 500
IAEAWCVDQR RTLEVFKELS KINPSAILSA IYNKPIAARF MGDVLGIASC 550
VTINQTSVKV LRDMNVKESP GRCYSRPVVI FNFANSSYVQ YGQLGEDNEI 600
LLGNHRTEEC QLPSLKIFIA GNSAYEYVDY LFKRMIDLSS ISTVDSMIAL 650
DIDPLENTDF RVLELYSQKE LRSSNVFDLE EIMREFNSYK QRVKYVEDKV 700
VDPLPPYLKG LDDLMSGLGA AGKAVGVAIG AVGGAVASVV EGVATFLKNP 750
FGAFTIILVA IAVVIITYLI YTRQRRLCTQ PLQNLFPYLV SADGTTVTSG 800
STKDTSLQAP PSYEESVYNS GRKGPGPPSS DASTAAPPYT NEQAYQMLLA 850
LARLDAEQRA QQNGTDSLDG QTGTQDKGQK PNLLDRLRHR KNGYRHLKDS 900
DEEENV
```

The amino acid sequence of HCMV gN is (SEQ ID NO: 20):

```
MEWNTLVLGL LVLSVVAESS GNNSSTSTSA TTSKSSASVS TTKLTTVATT  50
SATTTTTTTL STTSTKLSST THDPNVMRRH ANDDFYKAHC TSHMYELSLS 100
SFAAWWTMLN ALILMGAFCI VLRHCCFQNF TATTTKGY
```

The amino acid sequence of HCMV gM is (SEQ ID NO: 21):

```
MAPSHVDKVN TRTWSASIVF MVLTFVNVSV HLVLSNFPHL GYPCVYYHVV  50
DFERLNMSAY NVMHLHTPML FLDSVQLVCY AVFMQLVFLA VTIYYLVCWI 100
KISMRKDKGM SLNQSTRDIS YMGDSLTAFL FILSMDTFQL FTLTMSFRLP 150
```

-continued

```
SMIAFMAAVH FFCLTIFNVS MVTQYRSYKR SLFFFSRLHP KLKGTVQFRT 200
LIVNLVEVAL GFNTTVVAMA LCYGFGNNFF VRTGHMVLAV FVVYAIISII 250
YFLLIEAVFF QYVKVQFGYH LGAFFGLCGL IYPIVQYDTF LSNEYRTGIS 300
WSFGMLFFIW AMFTTCRAVR YFRGRGSGSV KYQALATASG EEVAVLSHHD 350
SLESRRLREE EDDDDDEDFE DA
```

The amino acid sequence of HCMV gO is (SEQ ID NO: 22):

```
MGRKEMMVRD VPKMVFLISI SFLLVSFINC KVMSKALYNR PWRGLVLSKI  50
GKYKLDQLKL EILRQLETTI STKYNVSKQP VKNLTMNMTE FPQYYILAGP 100
IQNYSITYLW FDFYSTQLRK PAKYVYSQYN HTAKTITFRP PPCGTVPSMT 150
CLSEMLNVSK RNDTGEQGCG NFTTFNPMFF NVPRWNTKLY VGPTKVNVDS 200
QTIYFLGLTA LLLRYAQRNC THSFYLVNAM SRNLFRVPKY INGTKLKNTM 250
RKLKRKQAPV KEQFEKKAKK TQSTTTPYFS YTTSAALNVT TNVTYSITTA 300
ARRVSTSTIA YRPDSSFMKS IMATQLRDLA TWVYTTLRYR QNPFCEPSRN 350
RTAVSEFMKN THVLIRNETP YTIYGTLDMS SLYYNETMFV ENKTASDSNK 400
TTPTSPSMGF QRTFIDPLWD YLDSLLFLDE IRNFSLRSPT YVNLTPPEHR 450
RAVNLSTLNS LWWWLQ
```

The amino acid sequence of HCMV UL128 is (SEQ ID NO: 23):

```
MSPKNLTPFL TALWLLLGHS RVPRVRAEEC CEFINVNHPP ERCYDFKMCN  50
RFTVALRCPD GEVCYSPEKT AEIRGIVTTM THSLTRQVVH NKLTSCNYNP 100
LYLEADGRIR CGKVNDKAQY LLGAAGSVPY RWINLEYDKI TRIVGLDQYL 150
ESVKKHKRLD VCRAKMGYML Q
```

The amino acid sequence of HCMV UL130 is (SEQ ID NO: 24):

```
MLRLLLRHYF HCLLLCAVWA TPCLASSWST LTANQNPSPP WSKLTYSKPH  50
DAATFYCPFL YPSPPRSPSQ FSGFQRVSTG PECRNETLYL LYNREGQTLV 100
ERSSTWVKKV IWYLSGRNQT ILQRMPRTAS KPSDGNVQIS VEDAKIFGAH 150
MVPKQTKLLR FVVNDGTRYQ MCVMKLESWA HVFRDYSVSF QVRLTFTEAN 200
NQTYTFCTHP NLIV
```

The amino acid sequence of HCMV UL131A is (SEQ ID NO: 25):

```
MRLCRVWLSV CLCAVVLGQC QRETAEKNDY YRVPHYWDAC SRALPDQTRY  50
KYVEQLVDLT LNYHYDASHG LDNFDVLKRI NVTEVSLLIS DFRRQNRRGG 100
TNKRTTFNAA GSLAPHARSL EFSVRLFAN
```

Human Herpes Virus 6 (HHV-6) and Human Herpes Virus 7 (HHV-7). Although HHV-6 and HHV-7 are distinct from HCMV in terms of genomic sequence, they retained a core of 80 herpesvirus-common ORFs that are also conserved in rodent CMVs. (Mocarski E., *Cell. Microb.,* 6(8):707-717, 2004). HHV-6 was first isolated in 1986 from peripheral blood leukocytes in patients presenting with lymphoproliferative disorders and AIDS. (Flamand et al., *J. Virol.,* 67(11):6768-6777, 1993). It is estimated that about 90% of individuals are infected by HHV-6 by the age of two, and approaches 100% in non-industrialized countries. (Salahuddin et al., *Science,* 234:596, 1986; Willis et al., *Br. Med. Bull.,* 62(1):125-138, 2002). HHV-6 infections cause *roseola infantum* (sixth disease), exanthem *subitum* rash (*roseola*) and is associated with heterophile-negative infectious mononucleosis, as well as meningoencephalitis, hepatitis, fatal hemophagocytic syndrome, and interstitial pneumonitis. (Id.). Further, there is some evidence suggesting a role in HHV-6 in certain cancers due to the detection of its genomic sequences in some B-cell lymphomas and the potential of HHV-6 to transform rodent cells. (Ablashi et al., *J. Virol. Methods,* 21:29-48, 1988; Josephs et al., *Science,* 234:601-603, 1986; Razzaque, A., *Oncogene,* 5:1356-1370, 1990; and Torelli et al., *Blood,* 77:2251-2258, 1991). There are two variants of HHV-6 confirmed by genetic sequencing: HHV-6A and HHV-6B. (Ablashi et al., *Arch. Virol.,* 159(5): 863-870, 2014). The genomes of the two variants are colinear and share an overall sequence identity of 90%. (Id.). Even the highly conserved glycoproteins gH, gB, gN, and gO are distinguishably different in sequence, and consistently different (conserved across isolates). The two variants also appear to exhibit slightly different epidemiology and disease associations. (Id.). Nonetheless, the same glycoproteins present in other HHV family members are encoded by the HHV-6 and HHV-7 genomes.

HHV-6 encodes many of the same surface glycoproteins as previously mentioned for other HHV family members, including gB, gH, gL, and gM, for which relatively conserved homologs have been identified in all known mammalian herpesviruses. (Santoro et al., *J. Biol. Chem.,* 278: 25964-25969, 2003; and Dockrell, D. H., *J. Med. Microbiol.,* 52:5-18, 2003). As with other family members, glycoproteins gH and gL play prominent roles in HHV-6 membrane fusion based on inhibitory activities of specific antibodies. (Foã-Tomasi et al., *J. Virol.,* 65:4124-4129, 1991; Gompels et al., *J. Virol.,* 65:2393-2401, 1991; Liu et al., *Virology,* 197:12-22, 1993; and Qian et al., *Virology,* 194:380-386, 1993). As in other herpesviruses, these glycoproteins form a heterodimeric complex, with gL being required for correct folding, intracellular maturation, and surface expression of gH. (Anderson et al., *J. Gen. Virol.,* 80:1485-1494, 1999; Hutchinson et al., *J. Virol.,* 66:2240-2250, 1992; Liu et al., *J. Gen. Virol.,* 74:1847-1857, 1993; and Roop et al., *J. Virol.,* 67:2285-2297, 1993). HHV-6 glycoprotein gB, known to be the most highly conserved glycoprotein among herpesviruses, and glycoprotein gp82-gp105 (only found in HHV-6 and the related Q-herpesvirus, HHV-7) are important for the fusion/entry process. (Takeda et al., *Virology,* 222:176-183, 1996; Pfeiffer et al., *J. Virol.,* 69:3490-3500, 1995; and Pfeiffer et al., *J. Virol.,* 67:4611-4620, 1993).

The antigenic compositions and methods of this application typically involve two or more HHV proteins involved in mediating HHV binding, fusion, and entry into host cells. In certain embodiments, two or more HHV-6 and HHV-7 proteins disclosed herein are combined in an antigenic composition. The two or more HHV-6 and HHV-7 proteins can be administered simultaneously or separately to induce an immune response or to treat or prevent an HHV-6 or HHV-7 infection in a subject. In certain embodiments, the antigenic composition (or method of administration) comprises two or more of the following HHV-6 and HHV-7 polypeptides (or nucleic acids encoding the same): gB, gH, and gL. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer.

In certain embodiments, the two or more HHV-6 or HHV-7 proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is trimeric and the gH/gL heterodimer is monomeric. In certain embodiments, the gB is trimeric and the gH/gL heterodimer is trimeric. In certain embodiments, the gB is monomeric and the gH/gL heterodimer is monomeric or trimeric. In certain embodiments, the HHV-6 or HHV-7 gB, gH, and gL polypeptides form a protein complex when mixed together. In certain embodiments, the HHV-6 or HHV-7 gB, gH, and gL polypeptides are not administered as a protein complex comprising the gB, gH, and gL polypeptides. For example, the gB can be administered separately from the gH and/or gL or administered with the gH and gL but not as a protein complex.

The amino acid sequence of HHV-6A gH is (SEQ ID NO: 26):

```
MLLRLWVFVL LTPCYGWRPL NISNSSHCRN GNFENPIVRP GFITFNFYTK  50
NDTRIYQVPK CLLGSDITYH LFDAINTTES LTNYEKRVIR FYEPPMNDIL 100
RLSPVPSVKQ FNLDRSIQPQ VVYSLNMYPS QGIYYVRVVE VRQMQYDNVS 150
CKLPNSLKEL IFPVQVRCAK ITRYVGEDIY THFFTPDFMI LYIQNPAGDL 200
TMMYGNTTSI NFKAPYKKSS FIFKQTLTDD LLLIVEKDVI DVQYRFISDA 250
TFVDETLNDV DEVEALLLKF NNLGIQTLLR GDCKKPNYAG IPQMMFLYGI 300
VHFSYSTKNT GPMPVLRVLK THENLLSIDS FVNRCVNVSE GTLQYPKMKE 350
FLKYEPSDYS YITKNKSISV STLLTYLATA YESNVTISKY KWTDIANTLQ 400
NIYEKHMFFT NLTFSDRETL FMLAEIANII PTDERMQRHM QLLIGNLCNP 450
VEIVSWARML TADRAPNLEN IYSPCASPVR RDVINSFLKT VLTYASLDRY 500
RSDMMEMLSV YRPPNMERVA AIQCLSPSEP AASLTLPNVT FVISPSYVIK 550
GVSLTITTTI VATSIIITAI PLNSTCVSTN YKYAGQDLLV LRNISSQTCE 600
FCQSVVMEYD DIDGPLQYIY IKNIDELKTL TDPNNNLLVP NTRTHYLLLA 650
KNGSVFEMSE VGIDIDQVSI ILVIIYILIA IIALFGLYRL IRLC
```

The amino acid sequence of HHV-6B gH is (SEQ ID NO: 27):

```
MLFRLWVFVL LTPCYSWRPW TISDESHCKN GNSENPIVRP GFITFNFYTK  50
NDTRIYQVPK CLLGSDITYH LFDAINTTES LTNYEKRVTR FYEPPMNDIL 100
RLSTVPAVKQ FNLDHSIQPQ IVYSLNLYPS HGIYYIRVVE VRQMQYDNVS 150
CKLPNSLNEL IFPVQVRCAK ITRYAGENIY THFFTPDFMI LYIQNPAGDL 200
IMMYGNTTDI NFKAPYRKSS FIFKQTLTDD LLLIVEKDVV DEEYRFISDA 250
TFVDETLDDV DEVEALLLKF NNLGIQTLLR GDCKKPDYAG IPQMMFLYGI 300
VHFSYSTKNT GPMPVLRVLK THENLLSIDS FVNRCVNVSE GTIQYPKMKE 350
FLKYEPSDYS YITKNKSIPV STLLTYLATA YETNVTISRY KWSDIANTLQ 400
KIYEKHMFFT NLTFSDRETL FMLAEIANFI PADERMQRHM QLLIGNLCNP 450
VEIVSWAHML TADKAPNLEN IYSPCASPVR RDVINSFVKT VLTYASLDRY 500
RSDMMEMLSV YRPPDMARVA AIQCLSPSEP AASLPLPNVT FVISPSYVIK 550
GVSLTITTTI VATSIIITAI PLNSTCVSTN YKYAGQDLLV LRNISSQTCE 600
FCQSVVMEYD DIDGPLQYIY IKNIDELKTL TDPNNNLLVP NTRTHYLLLA 650
KNGSVFEMSE VGIDIDQVSI ILVIIYVLIA IIALFGLYRL IRLC
```

The amino acid sequence of HHV-6A gL is (SEQ ID NO: 28):

```
MELLLFVMSL ILLTFSKAIP LFNHNSFYFF YLDDCIAAVI NCTKSEVPLL  50
LEPIYQPPAY NEDVMSILLQ PPTKKKPFSR IMVTDEFLSD FLLLQDNPEQ 100
LRTLFALIRD PESRDNWLNF FNGFQTCSPS VGITTCIRDN CRKYSPEKIT 150
YVNNFFVDNI AGLEFNISEN TDSFYSNIGF LLYLENPAKG VTKIIRFPFN 200
SLTLFDTILN CLKYFHLKTG VELDLLKHME TYNSKLPFRS SRPTILIRNT 250
```

The amino acid sequence of HHV-6B gL is (SEQ ID NO: 29):

```
MELLLFVMSL ILLTFSKAMP LFDHNSFYFE KLDDCIAAVI NCTRSEVPLL  50
LEPIYQPPVY NEDVMSILLK PPTKKKPFSR IMVTNEFLSD FLLLQDNPEQ 100
LRTLFALIGD PESRDNWLNF FNGFQTCSPS VGITTCISDN CRKYLPERIT 150
YVNNFFVDNI AGLEFNISEN TDSFYSNIGF LLYLENPATG ITKIIRFPFN 200
SLTLFDTILN CLKYFHLKTG VEFDLLKQME AYNSKLPFRS SRPTILIRNT 250
```

The amino acid sequence of HHV-6A gB is (SEQ ID NO: 30):

```
MSKMAVLFLA VFLMNSVLMI YCDPDHYIRA GYNHKYPFRI CSIAKGTDLM  50
RFDRDISCSP YKSNAKMSEG FFIIYKTNIE TYTFPVRTYK KELTFQSSYR 100
DVGVVYFLDR TVMGLAMPVY EANLVNSHAQ CYSAVAMKRP DGTVFSAFHE 150
DNNKNNTLNL FPLNFKSITN KRFITTKEPY FARGPLWLYS TSTSLNCIVT 200
EATAKAKYPF SYFALTTGEI VEGSPFFNGS NGKHFAEPLE KLTILENYTM 250
IEDLMNGMNG ATTLVRKIAF LEKADTLFSW EIKEENESVC MLKHWTTVTH 300
GLRAETNETY HFISKELTAA FVAPKESLNL TDPKQTCIKN EFEKIINEVY 350
```

-continued

```
MSDYNDTYSM NGSYQIFKTT GDLILIWQPL VQKSLMFLEQ GSEKIRRRRD 400
VGDVKSRHDI LYVQLQYLYD TLKDYINDAL GNLAESWCLD QKRTITMLHE 450
LSKISPSSIV SEVYGRPISA QLHGDVLAIS KCIEVNQSSV QLHKSMRVVD 500
AKGVRSETMC YNRPLVTFSF VNSTPEVVPG QLGLDNEILL GDHRTEECEI 550
PSTKIFLSGN HAHVYTDYTH TNSTPIEDIE VLDAFIRLKI DPLENADFKV 600
LDLYSPDELS RANVFDLENI LREYNSYKSA LYTIEAKIAT NTPSYVNGIN 650
SFLQGLGAIG TGLGSVISVT AGALGDIVGG VVSFLKNPFG GGLMLILAIV 700
VVVIIIVVFV RQRHVLSKPI DMMFPYATNP VTTVSSVTGT TVVKTPSVKD 750
VDGGTSVAVS EKEEGMADVS GQVSDDEYSQ EDALKMLKAI KSLDESYRRK 800
PSSSESHASK PSLIDRIRYR GYKSVNVEEA
```

The amino acid sequence of HHV-6B gB is (SEQ ID NO: 31):

```
MSKMRVLFLA VFLMNSVLMI YCDSDDYIRA GYNHKYPFRI CSIAKGTDLM  50
RFDRDISCSP YKSNAKMSEG FFIIYKTNIE TYTFPVRTYK NELTFPTSYR 100
DVGVVYFLDR TVMGLAMPVY EANLVNSRAQ CYSAVAIKRP DGTVFSAYHE 150
DNNKNETLEL FPLNFKSVTN KRFITTKEPY FARGPLWLYS TSTSLNCIVT 200
EATAKAKYPF SYFALTTGEI VEGSPFFDGS NGKHFAEPLE KLTILENYTM 250
IEDLMNGMNG ATTLVRKIAF LEKGDTLFSW EIKEENESVC MLKHWTTVTH 300
GLRAETDETY HFISKELTAA FVASKESLNL TDPKQTCIKN EFEKIITDVY 350
MSDYNDAYSM NGSYQIFKTT GDLILIWQPL VQKSLMVLEQ GSVNLRRRRD 400
LVDVKSRHDI LYVQLQYLYD TLKDYINDAL GNLAESWCLD QKRTITMLHE 450
LSKISPSSIV SEVYGRPISA QLHGDVLAIS KCIEVNQSSV QLYKSMRVVD 500
AKGVRSETMC YNRPLVTFSF VNSTPEVVLG QLGLDNEILL GDHRTEECEI 550
PSTKIFLSGN HAHVYTDYTH TNSTPIEDIE VLDAFIRLKI DPLENADFKL 600
LDLYSPDELS RANVFDLENI LREYNSYKSA LYTIEAKIAT NTPSYVNGIN 650
SFLQGLGAIG TGLGSVISVT AGALGDIVGG VVSFLKNPFG GGLMLILAIV 700
VVVIIIVVFV RQKHVLSKPI DMMFPYATNP VTTVSSVTGT TVVKTPSVKD 750
ADGGTSVAVS EKEEGMADVS GQISGDEYSQ EDALKMLKAI KSLDESYRRK 800
PSSSESHASK PSLIDRIRYR GYKSVNVEEA
```

The amino acid sequence of HHV-7 gH is (SEQ ID NO: 32):

```
MYFYINSLLL IVSINGWKHW NILNSSICVN EKTNQIIIQP GLITFNFHDY  50
NETRVYQIPK CLFGYTFVSN LFDSVNFDES FDQYKHRITR FFNPSTEKAV 100
KIYAQKFQTN IKPVSHTKTI TVSFLPLFYE KDVYFANVSE IRKLYYNQYI 150
CTLSNGLTDY LFPITERCVM RHYNYLNTVF MLALTPSFFI ISVETGMDDV 200
VFIFGNVSRI FFKAPFRKSS FIYRQTVSDD LLLITKKITI ERFYPFLKID 250
FLDDIWKQNY DISFLIAKFN KLATVYIMEG FCGKPVNKDT FHLMFLFGLT 300
HFLYSTRGDG LLPLLEILNT HQSIITMGRF LEKCFKMTKS HLLYPEMEKL 350
```

-continued

```
QNFQLVDYSY ITSDLTIPIS AKLAFLSLAD GRIVTVPQNK WKEIENNIET 400

LYEKHKLFTN LTQPERANLF LLSEIGNSLV FQEKIKRKIH VLLASLCNPL 450

EMYFWTHMLD NVMDIETMFS PCATATRKDL TQRVVNNILS YKNLDAYTNK 500

VMNTLSVYRK KRLDMFKSIS CVSNEQAAFL TLPNITYTIS SKYILAGTSF 550

SVTSTVISTT IIITVVPLNS TCTPTNYKYS VKNIKPIYNI SSHDCVFCES 600

LVVEYDDIDG IIQFVYIMDD KQLLKLIDPD INFIDVNPRT HYLLFLRNGS 650

VFEITALDLK SSQVSIMLVL LYLIIIIIVL FGIYHVFRLF
```

The amino acid sequence of HHV-7 gL is (SEQ ID NO: 33):

```
MKTNIFFIFL ISILNQIYAL FNNSYYSNLE QECIKNILNC TQSKTLSLLE  50

PIDQAPIPKS DIISRLLYHT PYISRRDQVL IDEDFLETFY LLYNNPNQLH 100

TLLSLIKDSE SGHNWLGFLN NFERCLSDNT LLTCRDNVCK SYSYEKLKFT 150

GNIFVENIIG FEFNIPSNMI NFNMSILIYL ENEETRTQRI VRIDHHGINV 200

FDALLNCLRY FSRYYNFSFP LIQEMEKYNE VLPFRSEFSN LLIRTY
```

The amino acid sequence of HHV-7 gB is (SEQ ID NO: 34):

```
MKILFLSVFI TFSLQLSLQT EADFVMTGHN QHLPFRICSI ATGTDLVRFD  50

REVSCASYGS NIKTTEGILI IYKTKIEAHT FSVRTFKKEL TFQTTYRDVG 100

TVYFLDRTVT TLPMPIEEVH MVNTEARCLS SISVKRSEEE EYVAYHKDEY 150

VNKTLDLIPL NFKSDTVRRY ITTKEPFLRN GPLWFYSTST SINCIVTDCI 200

AKTKYPFDFF ALSTGETVEG SPFYNGINSK TFNEPTEKIL FRNNYTMLKT 250

FDDGSKGNFV TLTKMAFLEK GNTIFSWEVQ NEESSICLLK HWMTIPHALR 300

AENANSFHFI AQELTASFVT GKSNYTLSDS KYNCINSNYT SILDEIYQTQ 350

YNNSHDKNGS YEIFKTEGDL ILIWQPLIQR KLTVLENFSN ASRKRRKREL 400

ETNKDIVYVQ LQYLYDTLKD YINTALGKLA EAWCLNQKRT ITVLHELSKI 450

SPSGIISAVY GKPMSAKLIG DVLAVSKCIE VNQTSVQLHK SMRLTKDSSY 500

DALRCYSRPL LTYSFANSSK ETYLGQLGLD NEILLGNHRT EECEQSNTKI 550

FLSGKFAHIF KDYTYVNSSL ITEIEALDAF VDLNIDPLEN ADFTLLELYT 600

KDELSKANVF DLETILREYN SYKSALHHIE TKIATVTPTY IGGIDTFFKG 650

LGALGLGLGA VLGVTAGALG DVVNGVFSFL KNPFGGALTI LLTLGVIGLV 700

IFLFLRHKRL AQTPIDILFP YTSKSTNSVL QATQSVQAQV KEPLDSSPPY 750

LKTNKDTEPQ GDDITHTNEY SQVEALKMLK AIKLLDESYK KAEIAEAKKS 800

QRPSLLERIQ YRGYQKLSTE EL
```

Alphaherpesviruses: Type 1 Human Herpes Virus (HHV-1), Type 2 Human Herpes Virus (HHV-2), & Varicella-Zoster Virus (VZV, HHV-3)

HHV-1, or herpes simplex virus-1 (HSV-1), causes oral herpes, HHV-2, or herpes simplex virus-1 (HSV-2) causes genital herpes, and HHV-3, or VZV, causes chickenpox and shingles. Each of these viruses belong to the alphaherpesvirus sub-family of the herpesvirus family and are neurotropic viruses. VZV infects nearly all humans and primary infection causes chickenpox (varicella). Latent VZV resides most commonly in the cranial nerve ganglia, dorsal root ganglia, and autonomic ganglia along the neuroaxis. The viruses of this sub-family and reactivate spontaneously, resulting in shingles (zoster). Zoster skin lesions usually last more than a week, but in some individuals infection can lead to chronic pain or postherpetic neuralgia (PHN, pain that lasts more than three months) as well as vasculopathy can occur in about 40% of patients older than 60 years of age. Zoster paresis (zoster with lower motor neuron type weakness) may also occur in the arms, legs, diaphragm, and/or abdominal muscles. Pathological features of zoster include inflammation and haemorrhagic necrosis with associated neuritis, localized leptomeningitis, unilateral segmental poliomyelitis, and degeneration of related motor and sensory roots. Demyelination is seen in areas with mononuclear cell (MNC) infiltration and microglial proliferation. Intranuclear inclusions, viral antigen, and herpesvirus particles have been found in acutely infected ganglia. Vasculopathy (or stroke) can be caused by productive virus infection of cerebral arteries and is referred to as granulomatous angiitis, VZV vasculitis/encephalitis, post-varicella arteriopathy, and herpes zoster ophthalmicus with delayed contralateral hemiparesis. Symptoms can include fever, altered mental status, headaches, and focal neurological deficits. (Gilden et al., *Neuropathol. Appl. Neurobiol.,* 37(5):441-463, 2012). Other serious complications of VZV infection include Mollaret's meningitis, zoster multiplex, muelitis, herpes ophthalmicus (zoster sine herpete), and Ramsay Hunt Syndrome. Studies have indicated an increased risk of stroke after zoster. (Kang et al., *Stroke,* 40(11):3443-3448, 2009; and Lin et al., *Neurology,* 74(10):792-797, 2010). Acute infections of VZV can lead to mengitis, meningoencephalitis, meningoradiculitis, and cerebellitis. (Habib et al., *J. Neurovirol.,* 15(2): 206-208, 2009; Klein et al., Scan. *J. Infect. Dis.,* 42(8):631-633, 2010; Gunson et al., *J. Clin. Virol.,* 50(3):191-193, 2011; and Moses et al., *Lancet Neurol.,* 5(11):984-988, 2006).

The VZV genome was the first herpesvirus genome to be completely sequenced, in 1986. The VZV genome is exceedingly stable, yielding only three point mutations in over 1200 passages. (Liu et al., *Arch. Virol.,* 153(10):1943-7, 2008). Infection proceeds from Langerhans cells to resident T cells near draining lymph nodes. T cells are induced to express skin-homing factors that transport the virus-loaded T cell to the dermis where fibroblasts and keratinocytes are exposed to infection and produce proinflammatory cytokines yielding varicella. (Taylor et al., *J. Virol.,* 79(17):11501-6, 2005; and Huch et al., *J. Virol.,* 84(8):4060-72, 2010). VZV triggers apoptosis in several cell types, including kidney cells, melanoma cells, fibroblasts, and others. (Pugazhenthi et al., *J. Virol.,* 83(18):9273-82, 2009).

Various pharmaceutical treatments are available for VZV infections, including acyclovir for the chicken pox, famciclovir, valaciclovir for the shingles, zoster-immune globulin (ZIG), and vidarabine. VZV immune globulin is also a treatment. (Centers for Disease Control and Prevention (CDC), March 2012, "FDA approval of an extended period for administering VariZIG for post exposure prophylaxis of varicella," *Morb. Mortal. Wkly. Rep.,* 61(12):212, PMID 2245612).

VZV and HSV-1/HSV-2 produce the known envelope glycoproteins gB, gH and gL, gM, gN, corresponding to the same or similar glycoproteins and associated protein functions found in other HHV species. Although there is no equivalent of the HHV-1/HHV-2 glycoprotein gD in VZV, glycoprotein gE of VZV performs a similar function. (Cohen, J. I., *Curr. Top. Microbiol. Immunol.,* 342:1-14, 2010). Expression of gB, gH, and gL is necessary and sufficient to induce membrane fusion, prior to virion entry into a host cell, allowing the nucleocapsid to gain access to the cytoplasm. Other accessory glycoproteins similar to gp42, gD, gO, or UL128-130, are not needed for fusion. (Eisenberg et al., *Viruses,* 4:800-832, 2012; Vleck et al., *Proc. Nat. Acad. Sci. USA,* 108:18412-7, 2011; and Oliver et al., *Proc. Nat. Acad. Sci. USA,* 110:1911-6, 2013).

At least two cell proteins, insulin-degrading enzyme (IDE), and myelin-associated glycoprotein (MAG), are thought to function as receptors for VZV entry into host cells; however, other studies implicate the αV subunit of integrins as playing a role in membrane fusion for VZV. (Yang et al., *J. Virol.,* 90(16):7567-78, 2016).

The antigenic compositions and methods of this application typically involve two or more HHV proteins involved in mediating HHV binding, fusion, and entry into host cells. In certain embodiments, two or more VZV proteins disclosed herein are combined in an antigenic composition. The two or more VZV proteins can be administered simultaneously or separately to induce an immune response or to treat or prevent a VZV infection in a subject. In certain embodiments, the antigenic composition (or method of administration) comprises two or more of the following VZV polypeptides (or nucleic acids encoding the same): gB, gH, and gL. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer.

In certain embodiments, the two or more VZV proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is monomeric and the gH/gL heterodimer is monomeric. In certain embodiments, the gB is trimeric and the gH/gL heterodimer is trimeric. In certain embodiments, the gB is trimeric and the gH/gL heterodimer is monomeric or trimeric. In certain embodiments, the VZV gB, gH, and gL polypeptides form a protein complex when mixed together. In certain embodiments, the VZV gB, gH, and gL polypeptides are not administered as a protein complex comprising the gB, gH, and gL polypeptides. For example, the gB can be administered separately from the gH and/or gL or administered with the gH and gL but not as a protein complex. In certain embodiments, the two or more VZV proteins further comprise one or more of the following glycoproteins: gI, gC, and/or gE, which can be monomeric or multimeric (e.g., dimeric, trimeric, or tetrameric).

The amino acid sequence of VZV gH is (SEQ ID NO: 35):

```
MFALVLAVVI LPLWTTANKS YVTPTPATRS IGHMSALLRE YSDRNMSLKL  50

EAFYPTGFDE ELIKSLHWGN DRKHVFLVIV KVNPTTHEGD VGLVIFPKYL 100

LSPYHFKAEH RAPFPAGRFG FLSHPVTPDV SFFDSSFAPY LTTQHLVAFT 150

TFPPNPLVWH LERAETAATA ERPFGVSLLP ARPTVPKNTI LEHKAHFATW 200

DALARHTFFS AEAIITNSTL RIHVPLFGSV WPIRYWATGS VLLTSDSGRV 250

EVNIGVGFMS SLISLSSGPP IELIVVPHTV KLNAVTSDTT WFQLNPPGPD 300

PGPSYRVYLL GRGLDMNFSK HATVDICAYP EESLDYRYHL SMAHTEALRM 350

TTKADQHDIN EESYYHIAAR IATSIFALSE MGRTTEYFLL DEIVDVQYQL 400
```

-continued

```
KFLNYILMRI GAGAHPNTIS GTSDLIFADP SQLHDELSLL FGQVKPANVD 450

YFISYDEARD QLKTAYALSR GQDHVNALSL ARRVIMSIYK GLLVKQNLNA 500

TERQALFFAS MILLNFREGL ENSSRVLDGR TTLLLMTSMC TAAHATQAAL 550

NIQEGLAYLN PSKHMFTIPN VYSPCMGSLR TDLTEEIHVM NLLSAIPTRP 600

GLNEVLHTQL DESEIFDAAF KTMMIFTTWT AKDLHILHTH VPEVFTCQDA 650

AARNGEYVLI LPAVQGHSYV ITRNKPQRGL VYSLADVDVY NPISVVYLSR 700

DTCVSEHGVI ETVALPHPDN LKECLYCGSV FLRYLTTGAI MDIIIIDSKD 750

TERQLAAMGN STIPPFNPDM HGDDSKAVLL FPNGTVVTLL GFERRQAIRM 800

SGQYLGASLG GAFLAVVGFG IIGWMLCGNS RLREYNKIPL T
```

The amino acid sequence of VZV gL is (SEQ ID NO: 36):

```
MASHKWLLQI VFLKTITIAY CLHLQDDTPL FFGAKPLSDV SLIITEPCVS  50

SVYEAWDYAA PPVSNLSEAL SGIVVKTKCP VPEVILWFKD KQMAYWTNPY 100

VTLKGLAQSV GEEHKSGDIR DALLDALSGV WVDSTPSSTN IPENGCVWGA 150

DRLFQRVCQ
```

The amino acid sequence of VZV gB is (SEQ ID NO: 37):

```
MSPCGYYSKW RNRDRPEYRR NLRFRRFFSS IHPNAAAGSG FNGPGVFITS  50

VTGVWLCFLC IFSMFVTAVV SVSPSSFYES LQVEPTQSED ITRSAHLGDG 100

DEIREAIHKS QDAETKPTFY VCPPPTGSTI VRLEPTRTCP DYHLGKNFTE 150

GIAVVYKENI AAYKFKATVY YKDVIVSTAW AGSSYTQITN RYADRVPIPV 200

SEITDTIDKF GKCSSKATYV RNNHKVEAFN EDKNPQDMPL IASKYNSVGS 250

KAWHTTNDTY MVAGTPGTYR TGTSVNCIIE EVEARSIFPY DSFGLSTGDI 300

IYMSPFFGLR DGAYREHSNY AMDRFHQFEG YRQRDLDTRA LLEPAARNFL 350

VTPHLTVGWN WKPKRTEVCS LVKWREVEDV VRDEYAHNFR FTMKTLSTTF 400

ISETNEFNLN QIHLSQCVKE EARAIINRIY TTRYNSSHVR TGDIQTYLAR 450

GGFVVVFQPL LSNSLARLYL QELVRENTNH SPQKHPTRNT RSRRSVPVEL 500

RANRTITTTS SVEFAMLQFT YDHIQEHVNE MLARISSSWC QLQNRERALW 550

SGLFPINPSA LASTILDQRV KARILGDVIS VSNCPELGSD TRIILQNSMR 600

VSGSTTRCYS RPLISIVSLN GSGTVEGQLG TDNELIMSRD LLEPCVANHK 650

RYFLFGHHYV YYEDYRYVRE IAVHDVGMIS TYVDLNLTLL KDREFMPLQV 700

YTRDELRDTG LLDYSEIQRR NQMHSLRFYD IDKVVQYDSG TAIMQGMAQF 750

FQGLGTAGQA VGHVVLGATG ALLSTVHGFT TFLSNPFGAL AVGLLVLAGL 800

VAAFFAYRYV LKLKTSPMKA LYPLTTKGLK QLPEGMDPFA EKPNATDTPI 850

EEIGDSQNTE PSVNSGFDPD KFREAQEMIK YMTLVSAAER QESKARKKNK 900

TSALLTSRLT GLALRNRRGY SRVRTENVTG V
```

The amino acid sequence of VZV gI is (SEQ ID NO: 38):

```
MFLIQCLISA VIFYIQVTNA LIFKGDHVSL QVNSSLTSIL IPMQNDNYTE  50

IKGQLVFIGE QLPTGTNYSG TLELLYADTV AFCFRSVQVI RYDGCPRIRT 100
```

-continued

```
SAFISCRYKH SWHYGNSTDR ISTEPDAGVM LKITKPGIND AGVYVLLVRL 150

DHSRSTDGFI LGVNVYTAGS HHNIHGVIYT SPSLQNGYST RALFQQARLC 200

DLPATPKGSG TSLFQHMLDL RAGKSLEDNP WLHEDVVTTE TKSVVKEGIE 250

NHVYPTDMST LPEKSLNDPP ENLLIIIPIV ASVMILTAMV IVIVISVKRR 300

RIKKHPIYRP NTKTRRGIQN ATPESDVMLE AAIAQLATIR EESPPHSVVN 350

PFVK
```

The amino acid sequence of VZV gC is (SEQ ID NO: 39):

```
MKRIQINLIL TIACIQLSTE SQPTPVSITE LYTSAATRKP DPAVAPTSAA  50

SRKPDPAVAP TSAASRKPDP AVAPTSAASR KPDPAVAPTS AATRKPDPAV 100

APTSAASRKP DPAVAPTSAA TRKPDPAVAP TSAASRKPDP AANTQHSQPP 150

FLYENIQCVH GGIQSIPYFH TFIMPCYMRL TTGQQAAFKQ QQKTYEQYSL 200

DPEGSNITRW KSLIRPDLHI EVWFTRHLID PHRQLGNALI RMPDLPVMLY 250

SNSADLNLIN NPEIFTHAKE NYVIPDVKTT SDFSVTILSM DATTEGTYIW 300

RVVNTKTKNV ISEHSITVTT YYRPNITVVG DPVLTGQTYA AYCNVSKYYP 350

PHSVRVRWTS RFGNIGKNFI TDAIQEYANG LFSYVSAVRI PQQKQMDYPP 400

PAIQCNVLWI RDGVSNMKYS AVVTPDVYPF PNVSIGIIDG HIVCTAKCVP 450

RGVVHFVWWV NDSPINHENS EITGVCDQNK RFVNMQSSCP TSELDGPITY 500

SCHLDGYPKK FPPFSAVYTY DASTYATTFS VVAVIIGVIS ILGTLGLIAV 550

IATLCIRCCS
```

The amino acid sequence of VZV gE is (SEQ ID NO: 40):

```
MGTVNKPVVG VLMGFGIITG TLRITNPVRA SVLRYDDFHT DEDKLDTNSV  50

YEPYYHSDHA ESSWVNRGES SRKAYDHNSP YIWPRNDYDG FLENAHEHHG 100

VYNQGRGIDS GERLMQPTQM SAQEDLGDDT GIHVIPTLNG DDRHKIVNVD 150

QRQYGDVFKG DLNPKPQGQR LIEVSVEENH PFTLRAPIQR IYGVRYTETW 200

SFLPSLTCTG DAAPAIQHIC LKHTTCFQDV VVDVDCAENT KEDQLAEISY 250

RFQGKKEADQ PWIVVNTSTL FDELELDPPE IEPGVLKVLR TEKQYLGVYI 300

WNMRGSDGTS TYATFLVTWK GDEKTRNPTP AVTPQPRGAE FHMWNYHSHV 350

FSVGDTFSLA MHLQYKIHEA PFDLLLEWLY VPIDPTCQPM RLYSTCLYHP 400

NAPQCLSHMN SGCTFTSPHL AQRVASTVYQ NCEHADNYTA YCLGISHMEP 450

SFGLILHDGG TTLKFVDTPE SLSGLYVFVV YFNGHVEAVA YTVVSTVDHF 500

VNAIEERGFP PTAGQPPATT KPKEITPVNP GTSPLLRYAA WTGGLAAVVL 550

LCLVIFLICT AKRMRVKAYR VDKSPYNQSM YYAGLPVDDF EDSESTDTEE 600

EFGNAIGGSH GGSSYTVYID KTR
```

The antigenic compositions and methods of this application typically involve two or more HHV proteins involved in mediating HHV binding, fusion, and entry into host cells. In certain embodiments, two or more HSV-1 or HSV-2 proteins disclosed herein are combined in an antigenic composition. The two or more HSV-1 or HSV-2 proteins can be administered simultaneously or separately to induce an immune response or to treat or prevent an HSV-1 or HSV-2 infection in a subject. In certain embodiments, the antigenic composition (or method of administration) comprises two or more of the following HSV-1 or HSV-2 polypeptides (or nucleic acids encoding the same): gB, gH, and gL. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer.

In certain embodiments, the two or more HSV-1 or HSV-2 proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is monomeric and the gH/gL heterodimer is monomeric or trimeric. In certain embodiments, the gB is trimeric and the gH/gL heterodimer is monomeric. In certain embodiments, the gB is trimeric and the gH/gL heterodimer is trimeric. In certain embodiments, the HSV-1 or HSV-2 gB, gH, and gL polypeptides form a protein complex when mixed together. In certain embodiments, the HSV-1 or HSV-2 gB, gH, and gL polypeptides are not administered as a protein complex comprising the gB, gH, and gL polypeptides. For example, the gB can be administered separately from the gH and/or gL or administered with the gH and gL but not as a protein complex.

In certain embodiments, the two or more HSV-1 or HSV-2 proteins further comprises a gD polypeptide, which can be monomeric or multimeric (e.g., dimeric, trimeric, or tetrameric).

The amino acid sequence of HSV-1 gH is (SEQ ID NO: 41):

```
MGNGLWFVGV IILGAAWGQV HDWTEQTDPW FLDGLGMDRM YWRDTNTGRL  50
WLPNTPDPQK PPRGFLAPPD ELNLTTASLP LLRWYEERFC FVLVTTAEFP 100
RDPGQLLYIP KTYLLGRPPN ASLPAPTTVE PTAQPPPAVA PLKGLLHNPT 150
ASVLLRSRAW VTFSAVPDPE ALTFPRGDNV ATASHPSGPR DTPPPRPPVG 200
ARRHPTTELD ITHLHNASTT WLATRGLLRS PGRYVYFSPS ASTWPVGIWT 250
TGELVLGCDA ALVRARYGRE FMGLVISMHD SPPAEVMVVP AGQTLDRVGD 300
PADENPPGAL PGPPGGPRYR VFVLGSLTRA DNGSALDALR RVGGYPEEGT 350
NYAQFLSRAY AEFFSGDAGA EQGPRPPLFW RLTGLLATSG FAFVNAAHAN 400
GAVCLSDLLG FLAHSRALAG LAARGAAGCA ADSVFFNVSV LDPTARLQLE 450
ARLQHLVAEI LEREQSLALH ALGYQLAFVL DSPSAYDAVA PSAAHLIDAL 500
YAEFLGGRVV TTPVVHRALF YASAVLRQPF LAGVPSAVQR ERARRSLLIA 550
SALCTSDVAA ATNADLRTAL ARADHQKTLF WLPDHFSPCA ASLRFDLDES 600
VFILDALAQA TRSETPVEVL AQQTHGLAST LTRWAHYNAL IRAFVPEASH 650
RCGGQSANVE PRILVPITHN ASYVVTHSPL PRGIGYKLTG VDVRRPLFLT 700
YLTATCEGST RDIESKRLVR TQNQRDLGLV GAVFMRYTPA GEVMSVLLVD 750
TDNTQQQIAA GPTEGAPSVF SSDVPSTALL LFPNGTVIHL LAFDTQPVAA 800
IAPGFLAASA LGVVMITAAL AGILKVLRTS VPFFWRRE
```

The amino acid sequence of HSV-1 gL is (SEQ ID NO: 42):

```
MGILGWVGLI AVGVLCVRGG LPSTEYVIRS RVAREVGDIL KVPCVPLPSD  50
DLDWRYETPS AINYALIDGI FLRYHCPGLD TVLWDRHAQK AYWVNPFLFV 100
AGFLEDLSYP AFPANTQETE TRLALYKEIR QALDSRKQAA SHTPVKAGCV 150
NFDYSRTRRC VGRQDLGPTN GTSGRTPVLP PDDEAGLQPK PLTTPPPIIA 200
TSDPTPRRDA ATKSRRRRPH SRRL
```

The amino acid sequence of HSV-1 gB is (SEQ ID NO: 43):

```
MHQGAPSWGR RWFVVWALLG LTLGVLVASA APTSPGTPGV AAATQAANGG  50
PATPAPPPLG AAPTGDPKPK KNKKPKNPTP PRPAGDNATV AAGHATLREH 100
LRDIKAENTD ANFYVCPPPT GATVVQFEQP RRCPTRPEGQ NYTEGIAVVF 150
KENIAPYKFK ATMYYKDVTV SQVWFGHRYS QFMGIFEDRA PVPFEEVIDK 200
INAKGVCRST AKYVRNNLET TAFHRDDHET DMELKPANAA TRTSRGWHTT 250
DLKYNPSRVE AFHRYGTTVN CIVEEVDARS VYPYDEFVLA TGDFVYMSPF 300
```

-continued

```
YGYREGSHTE HTTYAADRFK QVDGFYARDL TTKARATAPT TRNLLTTPKF 350

TVAWDWVPKR PSVCTMTKWQ EVDEMLRSEY GGSFRFSSDA ISTTFTTNLT 400

EYPLSRVDLG DCIGKDARDA MDRIFARRYN ATHIKVGQPQ YYQANGGFLI 450

AYQPLLSNTL AELYVREHLR EQSRKPPNPT PPPPGASANA SVERIKTTSS 500

IEFARLQFTY NHIQRHVNDM LGRVAIAWCE LQNHELTLWN EARKLNPNAI 550

ASVTVGRRVS ARMLGDVMAV STCVPVAADN VIVQNSMRIS SRPGACYSRP 600

LVSFRYEDQG PLVEGQLGEN NELRLTRDAI EPCTVGHRRY FTFGGGYVYF 650

EEYAYSHQLS RADITTVSTF IDLNITMLED HEFVPLEVYT RHEIKDSGLL 700

DYTEVQRRNQ LHDLRFADID TVIHADANAA MFAGLGAFFE GMGDLGRAVG 750

KVVMGIVGGV VSAVSGVSSF MSNPFGALAV GLLVLAGLAA AFFAFRYVMR 800

LQSNPMKALY PLTTKELKNP TNPDASGEGE EGGDFDEAKL AEAREMIRYM 850

ALVSAMERTE HKAKKKGTSA LLSAKVTDMV MRKRRNTNYT QVPNKDGDAD 900

EDDL
```

The amino acid sequence of HSV-1 gD is (SEQ ID NO: 44):

```
MGGAAARLGA VILFVVIVGL HGVRGKYALA DASLKMADPN RFRGKDLPVP  50

DRLTDPPGVR RVYHIQAGLP DPFQPPSLPI TVYYAVLERA CRSVLLNAPS 100

EAPQIVRGGS EDVRKQPYNL TIAWFRMGGN CAIPITVMEY TECSYNKSLG 150

ACPIRTQPRW NYYDSFSAVS EDNLGFLMHA PAFETAGTYL RLVKINDWTE 200

ITQFILEHRA KGSCKYALPL RIPPSACLSP QAYQQGVTVD SIGMLPRFIP 250

ENQRIVAVYS LKIAGWHGPK APYTSTLLPP ELSETPNATQ PELAPEDPED 300

SALLEDPVGT VAPQIPPNWH IPSIQDAATP YHPPATPNNM GLIAGAVGGS 350

LLAALVICGI VYWMRRRTQK GPKRIRLPHI REDDQPSSHQ PLFY
```

The amino acid sequence of HSV-2 gH is (SEQ ID NO: 45):

```
MGPGLWVVMG VLVGVAGGHD TYWTEQIDPW FLHGLGLART YWRDTNTGRL  50

WLPNTPDASD PQRGRLAPPG ELNLTTASVP MLRWYAERFC FVLVTTAEFP 100

RDPGQLLYIP KTYLLGRPRN ASLPELPEAG PTSRPPAEVT QLKGLSHNPG 150

ASALLRSRAW VTFAAAPDRE GLTFPRGDDG ATERHPDGRR NAPPPGPPAG 200

APRHPTTNLS IAHLHNASVT WLAARGLLRT PGRYVYLSPS ASTWPVGVWT 250

TGGLAFGCDA ALVRARYGKG FMGLVISMRD SPPAEIIVVP ADKTLARVGN 300

PTDENAPAVL PGPPAGPRYR VFVLGAPTPA DNGSALDALR RVAGYPEEST 350

NYAQYMSRAY AEFLGEDPGS GTDARPSLFW RLAGLLASSG FAFINAAHAH 400

DAIRLSDLLG FLAHSRVLAG LAARGAAGCA ADSVFLNVSV LDPAARLRLE 450

ARLGHLVAAI LEREQSLAAH ALGYQLAFVL DSPAAYGAVA PSAARLIDAL 500

YAEFLGGRAL TAPMVRRALF YATAVLRAPF LAGAPSAEQR ERARRGLLIT 550

TALCTSDVAA ATHADLRAAL ARTDHQKNLF WLPDHFSPCA ASLRFDLAEG 600

GFILDALAMA TRSDIPADVM AQQTRGVASA LTRWAHYNAL IRAFVPEATH 650

QCSGPSHNAE PRILVPITHN ASYVVTHTPL PRGIGYKLTG VDVRRPLFIT 700
```

-continued

```
YLTATCEGHA REIEPKRLVR TENRRDLGLV GAVFLRYTPA GEVMSVLLVD 750

TDATQQQLAQ GPVAGTPNVF SSDVPSVALL LFPNGTVIHL LAFDTLPIAT 800

IAPGFLAASA LGVVMITAAL AGILRVVRTC VPFLWRRE
```

The amino acid sequence of HSV-2 gL is (SEQ ID NO: 46):

```
MGFVCLFGLV VMGAWGAWGG SQATEYVLRS VIAKEVGDIL RVPCMRTPAD  50

DVSWRYEAPS VIDYARIDGI FLRYHCPGLD TFLWDRHAQR AYLVNPFLFA 100

AGFLEDLSHS VFPADTQETT TRRALYKEIR DALGSRKQAV SHAPVRAGCV 150

NFDYSRTRRC VGRRDLRPAN TTSTWEPPVS SDDEASSQSK PLATQPPVLA 200

LSNAPHGGSP RREVGAGILA SDATSHVCIA SHPGSGAGQP TRLAAGSAVQ 250

RRRPRGCPPG VMFSASTTPE QPLGLSGDAT PPLPTSVPLD WAAFRRAFLI 300

DDAWRPLLEP ELANPLTARL LAEYDRRCQT EEVLPPREDV FSWTRYCTPD 350

DVRVVIIGQD PYHHPGQAHG LAFSVRADVP VPPSLRNVLA AVKNCYPDAR 400

MSGRGCLEKW ARDGVLLLNT TLTVKRGAAA SHSKLGWDRF VGGVVRRLAA 450

RRPGLVFMLW GAHAQNAIRP DPRQHYVLKF SHPSPLSKVP FGTCQHFLAA 500

NRYLETRDIM PIDWSV
```

The amino acid sequence of HSV-2 gB is (SEQ ID NO: 47):

```
MRGGGLICAL VVGALVAAVA SAAPAAPAAP RASGGVAATV AANGGPASRP  50

PPVPSPATTK ARKRKTKKPP KRPEATPPPD ANATVAAGHA TLRAHLREIK 100

VENADAQFYV CPPPTGATVV QFEQPRRCPT RPEGQNYTEG IAVVFKENIA 150

PYKFKATMYY KDVTVSQVWF GHRYSQFMGI FEDRAPVPFE EVIDKINTKG 200

VCRSTAKYVR NNMETTAFHR DDHETDMELK PAKVATRTSR GWHTTDLKYN 250

PSRVEAFHRY GTTVNCIVEE VDARSVYPYD EFVLATGDFV YMSPFYGYRE 300

GSHTEHTSYA ADRFKQVDGF YARDLTTKAR ATSPTTRNLL TTPKFTVAWD 350

WVPKRPAVCT MTKWQEVDEM LRAEYGGSFR FSSDAISTTF TTNLTEYSLS 400

RVDLGDCIGR DAREAIDRMF ARKYNATHIK VGQPQYYLAT GGFLIAYQPL 450

LSNTLAELYV REYMREQDRK PRNATPAPLR EAPSANASVE RIKTTSSIEF 500

ARLQFTYNHI QRHVNDMLGR IAVAWCELQN HELTLWNEAR KLNPNAIASA 550

TVGRRVSARM LGDVMAVSTC VPVAPDNVIV QNSMRVSSRP GTCYSRPLVS 600

FRYEDQGPLI EGQLGENNEL RLTRDALEPC TVGHRRYFIF GGGYVYFEEY 650

AYSHQLSRAD VTTVSTFIDL NITMLEDHEF VPLEVYTRHE IKDSGLLDYT 700

EVQRRNQLHD LRFADIDTVI RADANAAMFA GLCAFFEGMG DLGRAVGKVV 750

MGVVGGVVSA VSGVSSFMSN PFGALAVGLL VLAGLVAAFF AFRYVLQLQR 800

NPMKALYPLT TKELKTSDPG GVGGEGEEGA EGGGFDEAKL AEAREMIRYM 850

ALVSAMERTE HKARKKGTSA LLSSKVTNMV LRKRNKARYS PLHNEDEAGD 900

EDEL
```

The amino acid sequence of HSV-2 gD is (SEQ ID NO: 48):

```
MGRLTSGVGT AALLVVAVGL RVVCAKYALA DPSLKMADPN RFRGKNLPVL  50

DRLTDPPGVK RVYHIQPSLE DPFQPPSIPI TVYYAVLERA CRSVLLHAPS 100

EAPQIVRGAS DEARKHTYNL TIAWYRMGDN CAIPITVMEY TECPYNKSLG 150

VCPIRTQPRW SYYDSFSAVS EDNLGFLMHA PAFETAGTYL RLVKINDWTE 200

ITQFILEHRA RASCKYALPL RIPPAACLTS KAYQQGVTVD SIGMLPRFIP 250

ENQRTVALYS LKIAGWHGPK PPYTSTLLPP ELSDTTNATQ PELVPEDPED 300

SALLEDPAGT VSSQIPPNWH IPSIQDVAPH HAPAAPSNPG LIIGALAGST 350

LAVLVIGGIA FWVRRRAQMA PKRLRLPHIR DDDAPPSHQP LFY
```

HHV Proteins. This application demonstrates that various combinations of HHV proteins involved in mediating viral binding, fusion, and host cell entry unexpectedly induce synergistic or additive neutralizing antibody responses, notwithstanding concerns in the art about vaccine or immune interference. The HHV proteins that are combined in the antigenic compositions disclosed herein (e.g., gB, gH, gL, gp350) or administered (simultaneously or separately) to prevent or treat a HHV infection or induce immunity in a subject can be made using any conventional technique.

For example, in certain embodiments, one or more of the HHV proteins are naturally occurring. In other embodiments, one or more of the HHV proteins are recombinant (i.e., prepared using recombinant DNA techniques). In certain embodiments, the recombinant HHV proteins have one or more differences in the glycosylation pattern of the naturally occurring HHV proteins. In certain embodiments one or more of the HHV proteins have been modified and are not naturally occurring proteins. In certain embodiments all of the HHV proteins have been modified and are not naturally occurring proteins. For example, the HHV proteins may be a mutated version of the wild type protein, a truncated version of the wild type protein, a multimerized protein, or a fusion protein.

In certain embodiments, the modified HHV protein is a protein that binds to a specific target molecule and the modified HHV protein retains its ability to bind to the target molecule. In certain embodiments, the truncated HHV protein consists of the extracellular domain of the HHV protein or a portion thereof that retains the ability to bind to its target molecule, including, for example, the extracellular domain of one or more of gB, gp350, gL, or gH. By way of example, gp350 binds to CD21 (aka CR2) on the surface of B cells; gp42 binds to HLA class II molecules; gD binds to nectin-1 (HveC, CD111) and Herpesvirus Entry Mediator (HVEM); and gpK8.1A and gpK8.1B bind to a cell surface heparin sulfate molecule.

In certain embodiments, the HHV polypeptide is a variant HHV polypeptide comprising one or more deletions, insertions, or substitutions. For example, gp350 and gp220 polypeptides that bind to CR2 include naturally-occurring or synthetically programmed variant polypeptides substantially identical to either the gp350 or gp220 polypeptides, but which have an amino acid sequence different from that of gp350 or gp220 because of one or more deletions, insertions or substitutions. Some gp350/220 variant sequences have already been identified by sequencing the DNA of different strains of EBV, and are readily available to one of ordinary skill in the art (Beisel et al., *J. Viriol.,* 1985, 54(3):665-74).

Similarly, variant gH, gL, gB, gp42, gM, gN, gI, gC, gE, gD, ORF68, BMRF-2, UL128, UL130, UL131A, and gpK8.1 polypeptides can include naturally-occurring or synthetically programmed variant polypeptides substantially identical to either the gH, gL, gB, gp42, gM, gN, gI, gC, gE, gD, ORF68, BMRF-2, UL128, UL130, UL131A, and gpK8.1 polypeptides, but which have an amino acid sequence different from that of gH, gL, gB, gp42, gM, gN, gI, gC, gE, gD, ORF68, BMRF-2, UL128, UL130, UL131A, and gpK8.1 because of one or more deletions, insertions or substitutions.

The variant amino acid sequence preferably is at least 60%, 65%, 70%, or 80%, identical to a gp350, a gp220 polypeptide or a gH, gL, gB, gp42, gM, gN, gI, gC, gE, gD, ORF68, BMRF-2, UL128, UL130, UL131A, and gpK8.1, more preferably at least 85% identical, still more preferably at least 90% identical, and most preferably at least 95% identical. The percent identity can be determined, for example, by comparing sequence information using the GAP computer program, version 6.0 described by Devereux et al. (*Nucl. Acids Res.,* 12:387, 1984) and available from the University of Wisconsin Genetics Computer Group (UWGCG). The GAP program utilizes the alignment method of Needleman and Wunsch (*J. Mol. Biol.,* 48:443, 1970), as revised by Smith and Waterman (*Adv. Appl. Math,* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.,* 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps.

Variant polypeptides can be obtained by mutation of nucleotide sequences encoding the gp350, gp220, gH, gL, gB, gp42, gM, gN, gI, gC, gE, gD, ORF68, BMRF-2, UL128, UL130, UL131A, and/or gpK8.1 polypeptides. Alterations of the amino acid sequence can occur naturally, or be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene,* 42:133, 1986); Bauer et al. (*Gene* 37:73, 1985); Craik, (BioTechniques, Jan. 12-19, 1985); Smith et al. (Genetic Engineering: Principles and Methods, Plenum Press, 1981); Kunkel (*Proc. Natl. Acad. Sci. USA,* 82:488, 1985); Kunkel et al. (*Methods in Enzymol.,* 154:367, 1987); and U.S. Pat. Nos. 4,518,584 and 4,737,462, all of which are incorporated by reference.

Even though multimerizing HHV proteins has been shown to enhance their immunogenicity (see US2015-0174237 A1 and US2016-0303225 A1, which are incorporated by reference in their entirety), unexpected additive and synergistic antibody responses were observed when both multimeric and/or monomeric HHV proteins were combined. Thus, in certain embodiments, one or more of the HHV proteins is a monomeric form of the protein. In certain embodiments, one or more of the HHV proteins is a multimeric form of the protein. In certain embodiments, one or more of the HHV proteins is monomeric and one or more of the HHV proteins is multimeric. In certain embodiments, the antigenic composition comprises a HHV gB polypeptide that is monomeric or multimeric. In certain embodiments, the multimeric gB polypeptide is dimeric or trimeric and preferably trimeric. In certain embodiments, the gp350 polypeptide is monomeric or multimeric. In certain embodiments, the multimeric gp350 is dimeric, trimeric, or tetrameric and preferably tetrameric. Methods for multimerizing HHV proteins are known in the art and are discussed elsewhere in this application.

The HHV gH and gL polypeptides can be combined as individual polypeptides in the antigenic compositions and methods described herein. In other embodiments, gH and gL form a gH/gL heterodimer. In certain embodiments, the gH/gL heterodimer is a non-covalently associated protein complex, such as the gH/gL protein complex that occurs naturally and can form spontaneously under certain in vitro conditions. In other embodiments, the gH/gL heterodimer is a fusion protein. If the HHV antigenic composition comprises the gH polypeptide and gL polypeptide in the form of a gH/gL heterodimer, the antigenic composition further comprises the gB polypeptide or, for EBV, the antigenic composition further comprises gB and/or the gp350 polypeptide. In certain embodiments, the gH or gL polypeptides are monomeric or multimeric. In certain embodiments, the gH or gL polypeptide is dimeric, trimeric, or tetrameric and preferably trimeric. In certain embodiments, the gH/gL heterodimer is monomeric or multimeric. In certain embodiments, the multimeric gI/gL heterodimer is dimeric, trimeric, or tetrameric and preferably trimeric.

Multimerizing HHV Proteins. As discussed above, the two or more HHV polypeptides in the disclosed antigenic compositions may be multimerized or they may be monomeric. For instance, it is known that at least the gH and gL polypeptides under some conditions form heterodimers. Further, it is known that under some conditions the gB polypeptide exists as a multimer, for instance at least as a homotrimer. (Ma, A., *Virology,* 178(2):588-592, 1990). Further, it is known that polypeptide gB associates with the heterodimer gH/gL to form a heterotrimer complex of gB/gH/gL under certain circumstances. Thus, upon introducing such HHV polypeptides into a composition, multimerization can spontaneously occur under some circumstances.

While multimerization of the HHV polypeptides can occur spontaneously for some polypeptides under appropriate conditions, others do not form multimers under natural conditions. In some embodiments it is advantageous to modify the two or more HHV polypeptides to form multimers to enhance their immunogenicity. In certain embodiments, a trimeric HHV gB polypeptide is formed by expressing a modified HHV gB polypeptide in a host cell. In the modified gB polypeptide, the furin cleavage site in the extracellular domain of the gB polypeptide is replaced by a linker sequence, as described in WO2015/089340 (also published as US2016-0303225 A1, which is incorporated by reference in its entirety). FIG. 1, right panel, and FIG. 7 depict an exemplary modified EBV and HCMV gB constructs, which form a homotrimeric gB complex when expressed in a host cell. In these embodiments, a linker sequence (e.g., $(Gly_4Ser)_3$ (SEQ ID NO: 3)) replaces the furin cleavage site in the extracellular domain of the EBV or HCMV gB polypeptide. An optional leader sequence can be added to the construct to direct secretion of the recombinant polypeptide. Although these embodiments are shown with the EBV and HCMV gB polypeptides, any HHV gB sequence can be substituted in the construct to produce the desired, modified gB polypeptide.

In certain embodiments, multimeric HHV proteins can be synthesized using recombinant cloning techniques to combine oligomerization domains with a HHV polypeptide, which is optionally expressed as a fusion protein, as described, for example, in WO2014/018858 (also published as US2015-0174237 A1, which is incorporated by reference in its entirety).

Fusion Proteins. The fusion proteins used to make multimeric HHV proteins can be synthesized using standard, recombinant cloning techniques. For instance, one strategy for making a fusion protein involves creating nucleic acid constructs comprising oligomerization motif sequences and a linker sequence separating two or more antigens such that the encoded fusion protein can form a dimeric, trimeric, tetrameric, hexameric, heptameric, or octameric complex from a single nucleic acid construct. (See, WO 2014/018858, incorporated herein by reference for all purposes). This platform can be used to create multimeric fusion proteins comprising multiple copies of a single antigen of interest, including, for example, a gp350, gp220 polypeptide, or gB. For example, a homodimer, homotrimer, or homotetramer can be created using two, three, or four copies of the same polypeptide with a dimerization, trimerization, or tetramerization domain, respectively. When the oligomerization domains associate together, the construct will form a tetramer (if a dimerization domain is used) comprising four copies of the same polypeptide, a hexamer (if a trimerization domain is used) comprising six copies of the same polypeptide, or an octamer comprising eight copies of the same polypeptide (if a tetramerization domain is used).

Alternatively, this platform can be used to create multimeric fusion proteins comprising two or more different antigens of interest. For example, a heterodimer can be created with a first HHV polypeptide linked to a second different, HHV polypeptide (or a heterotrimer comprising two or three different antigens), such as a heterodimer formed between HHV gH and gL. When the oligomerization domains associate together, the construct will form a tetramer (if a dimerization domain is used) that is dimeric for both the first and second HHV polypeptide, a hexamer (if a trimerization domain is used in the construct) that is dimeric for at least the first and second HHV polypeptide, or trimeric for the first, second, and third HHV polypeptide, or an octamer (if a tetramerization domain is used).

In one embodiment, a trimeric protein can be formed if the original polypeptide is presented in monomeric form in association with the trimerization domain. The fusion protein may optionally further comprise a third polypeptide and a second linker sequence, where the second linker sequence joins the second polypeptide to the third polypeptide, the first polypeptide, or the oligomerization domain. In other embodiments, the fusion protein comprises four or more polypeptides and additional linkers. In one embodiment, the fusion protein forms a multimeric polypeptide when expressed in a host cell. In another embodiment, the first and second polypeptides do not occur naturally as a multimeric protein.

In some embodiments, only a portion of the extracellular domain of each the HHV polypeptide is engineered into the nucleic acid construct encoding the fusion protein. Shorter polypeptides are easier to express in larger quantities and in some embodiments only a portion of the HHV polypeptide is needed or desired to achieve the desired immunological effect, i.e., those portions of the HHV polypeptides that elicit an immune response.

The nucleic acid constructs optionally include a signal peptide-encoding nucleic acid so that the expressed fusion protein is excreted from the mammalian host cell, e.g. a tissue culture comprising one or more host cells, such as, for instance, a HeLa cells, yeast cells, insect cells, Chinese Hamster Ovary (CHO) cells, Human Embryonic Kidney (HEK) cells, COS cells, Vero cells, NS0 mouse myeloma cells, and others disclosed in the art, such as Khan, K., Adv. *Pharm. Bull.,* 3(2):257-263, 2013. Secretion of the fusion protein provides an easy means for protein harvesting and purification by known methodologies.

In one embodiment, the fusion protein is formed from expression of a nucleic acid construct comprising nucleic acid sequences encoding one or more gp350 polypeptides, for example two such sequences, such that when expressed with a dimerization domain, such as a leucine zipper oligomerization domain, a gp350 tetramer, is formed. (See, FIG. 1, left panel). The gp350 nucleic acid sequence can be from any HHV genome comprising such a sequence. Alternatively, the gp350 sequences can be substituted with one or more other HHV polypeptide disclosed herein.

As depicted in the middle panel of FIG. 1, in another embodiment the fusion protein can be encoded by a first nucleic acid construct encoding gH and a second nucleic acid encoding gL, and a trimerization domain, such as the T4 foldon oligomerization domain, thereby yielding upon expression, for example, a trimeric gH/gL heterodimer. The gH and gL polypeptides can be any gH/gL polypeptide sequence found in any of the known HHV genomes. Alternatively, in another embodiment, the gH and/or gL polypeptides can be substituted with one or more other HHV polypeptides to form the desired HHV protein complex as described herein.

In such embodiments, it is not necessary that the nucleic acid constructs comprise full length HHV polypeptide sequences. The sequences can be modified. For instance, the modified sequence can be a partial, truncated, or otherwise altered or mutated sequence. Such modified sequences can improve protein expression, for instance by removing the transmembrane and intracellular domain sequences, or can elicit a more robust immune response, for instance by strategically arranging highly immunogenic epitopes of the HHV polypeptides discussed herein.

Linker Sequences. Linker sequences are used in the modified gB polypeptide to replace the furin cleavage site in the extracellular domain of the gB polypeptide. Linker sequences are also used in the fusion proteins to separate different components of the fusion protein. Thus, in certain embodiments, the amino terminal end of the linker sequence is joined by a peptide bond to a first polypeptide and the carboxy terminal end of the linker sequence is joined by a peptide bind to a second polypeptide. The first and second polypeptides are each one of the HHV fusion and host cell entry proteins or one of the HHV accessory proteins. In certain embodiments, the first and second polypeptides are the same (e.g., gp350). In other embodiments, the first and second polypeptides are different (e.g., gH and gL). Such a linker sequence joins the first polypeptide and the second polypeptide, in contrast to a first polypeptide and a second polypeptide that are joined together without an intervening polypeptide sequence. It is understood that the linker sequence is not a sequence that naturally separates a first and second polypeptide, if the first and second polypeptide happen to naturally exist in combination together.

In one embodiment, the linker sequence is a polypeptide having 5-25 amino acids, particularly a length of 6, 7, 8, 9, 10, 11, 12, 13, 14, 15, 16, 17, 18, 19 or 20 amino acids. In another embodiment, the linker sequence is a polypeptide having 10-25 amino acids. The linker sequence preferably comprises glycine and serine amino acids. In one embodiment, the linker sequence is 15 amino acids in length and has the amino acid sequence $(Gly_4Ser)_3$ (SEQ ID NO: 3).

Other suitable peptide linkers are those described in U.S. Pat. Nos. 4,751,180, 4,935,233, and 5,073,627, each of which is hereby incorporated by reference in its entirety. A DNA sequence encoding a desired linker sequence may be inserted between, and in the same reading frame as, for example, DNA sequences encoding the first and second polypeptide using conventional techniques known in the art. For example, a chemically synthesized oligonucleotide encoding the linker may be ligated between sequences encoding the first and second polypeptide.

Oligomerization Domains. Oligomerization domains are used in certain embodiments to make multimeric HHV polypeptides. Oligomerization domains are stretches of amino acid residues that cause polypeptides comprising them to oligomerize, i.e., to form covalent and/or non-covalent associations with another polypeptide comprising a corresponding or cognate oligomerization domain. Thus, two or more polypeptides are "oligomerized" if they are bound to each other via their oligomerization domains. Any oligomerization domain known in the art can be used. Examples include leucine zipper domains, complement C1q domains, α-helical coiled coil domains, thrombospondin domains, and fibritin domains. (See, Engel et al., *Matrix Biol.,* 19(4):283-288, 2000). The polypeptides in an oligomer can have identical polypeptide sequences, similar polypeptide sequences, or different polypeptide sequences.

Homodimerization and homo-oligomerization refer to the association of the same polypeptide components to form dimers or oligomers. Heterodimerization and hetero-oligomerization refer to the association of different polypeptides to form dimers or oligomers. Homo-oligomers thus comprise an association of multiple copies of a particular polypeptide, while hetero-oligomers comprise an association of copies of different polypeptides. "Oligomerization," "oligomerize," and "oligomer," with or without prefixes, are intended to encompass "dimerization," "dimerize," and "dimer." Thus, in one embodiment, the oligomerization domain is a dimerization domain that mediates the self-association of two HHV polypeptides and/or two HHV fusion proteins. In another embodiment, the oligomerization domain is a trimerization domain that mediates the self-association of three HHV polypeptides and/or three HHV fusion proteins. In another embodiment, the oligomerization domain is a tetramerization domain that mediates the self-association of four HHV polypeptides and/or four HHV fusion proteins. In one embodiment, the trimerization domain is fibritin motif or a eukaryotic GCN4 transcription factor motif or derivative thereof.

In one embodiment, the oligomerization domain comprises a leucine zipper domain. Leucine zipper domains are peptides that promote oligomerization of the proteins in which they are found. Leucine zippers were originally identified in several DNA-binding proteins (Landschulz et al., *Science,* 240:1759, 1988), and have since been found in a variety of different proteins. Among the known leucine zippers are naturally occurring peptides and derivatives thereof that dimerize or trimerize. For example, the yeast GCN4 leucine zipper can be used to dimerize polypeptides of interest. (Czerwinski et al., *Transfusion,* 35(2):137-44, 1995; and O'Shea et al., *Science,* 243(4890):538-42, 1989). Other examples of leucine zipper domains suitable for producing soluble multimeric proteins are described in PCT application WO 94/10308, and the leucine zipper derived from lung surfactant protein D (SPD) described in Hoppe et al. *FEBS Lett.* 344:191, 1994. The use of a modified leucine zipper that allows for stable trimerization of a heterologous protein fused thereto is described in Fanslow et al., *Semin. Immunol.,* 6:267, 1994.

In yet another embodiment, the oligomerization domain is a fibritin trimerization motif, particularly a bacteriophage fibritin trimerization motif, more particularly a fibritin trimerization domain from bacteriophage T4 (also called T4 foldon or foldon domain) or phage RB69 or phage AR1 or a derivative thereof. The T4 fibritin trimerization domain and variants thereof are described in U.S. Pat. Nos. 6,911,205; 8,147,843, and WO 01/19958, which are hereby incorporated by reference in their entirety.

Protein Complexes. In certain embodiments, the HHV polypeptides disclosed herein are present in the antigenic composition as a protein complex. For example, in certain embodiments, the HHV gB, gL, and gH are present in the antigenic composition as a protein complex. In other embodiments, the HHV gH, gL, UL128, UL130, and UL131A polypeptides are present in the antigenic composition as a protein complex. In yet another embodiment, the HHV gH, gL, and gO polypeptides are present in the antigenic composition as a protein complex.

Proteins in the protein complex are typically linked by non-covalent protein-protein interactions, including but not limited to hydrogen bonding and salt bridges. The protein complex has a quaternary structure, corresponding to the arrangement or shape resulting from the assembly and interaction of the individual proteins, and, therefore, is useful for inducing neutralizing antibodies against conformation epitopes on the HHV protein complex. In some embodiments, the protein complex, as used herein, does not refer to the native protein complex as it exists on the surface of a herpesvirus. Rather, the protein complex is formed by incubating the individual proteins in vitro, to create a reconstructed protein complex.

Nucleic Acids, Cloning, and Expression Systems. The present disclosure further provides isolated nucleic acids encoding the disclosed monomeric or multimeric HHV polypeptides. The nucleic acids may comprise DNA or RNA and may be wholly or partially synthetic or recombinant. Reference to a nucleotide sequence as set out herein encompasses a DNA molecule with the specified sequence and encompasses an RNA molecule with the specified sequence in which U is substituted for T, unless context requires otherwise.

The present disclosure also provides constructs in the form of plasmids, vectors, phagemids, transcription or expression cassettes which comprise at least one nucleic acid encoding a monomeric or multimeric HHV fusion or host cell entry protein or a portion thereof. The disclosure further provides a host cell which comprises one or more constructs as above.

Also provided are methods of making the monomeric or multimeric HHV polypeptides encoded by these nucleic acids. The monomeric or multimeric HHV polypeptides may be produced using recombinant techniques. The production and expression of recombinant proteins is well known in the art and can be carried out using conventional procedures, such as those disclosed in Sambrook et al., Molecular Cloning: A Laboratory Manual (4th Ed. 2012), Cold Spring Harbor Press. For example, expression of the fusion protein may be achieved by culturing under appropriate conditions recombinant host cells containing the nucleic acid encoding the monomeric or multimeric HHV polypeptides. Following production by expression a monomeric or multimeric HHV polypeptides may be isolated and/or purified using any suitable technique, then used as appropriate. As discussed herein, under certain conditions, two or more the HHV fusion and host cell entry proteins and optionally one or more HHV accessory proteins form a protein complex when incubated in vitro.

Systems for cloning and expression of a polypeptide in a variety of different host cells are well known in the art. Any protein expression system compatible with the constructs disclosed in this application may be used to produce the disclosed monomeric or multimeric HHV polypeptides.

Suitable vectors can be chosen or constructed, so that they contain appropriate regulatory sequences, including promoter sequences, terminator sequences, polyadenylation sequences, enhancer sequences, marker genes and other sequences as appropriate.

Figure 14:
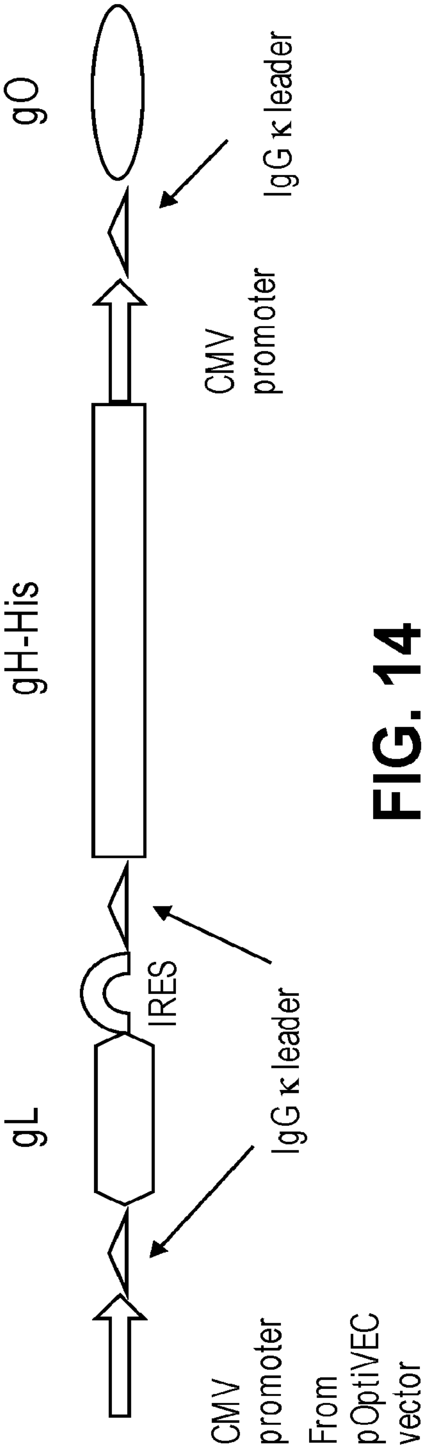
FIG. 14 shows a schematic diagram of a non-limiting DNA construct for expression of a gH/gL/gO complex.

A further aspect of the disclosure provides a host cell comprising a nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. These techniques are well known in the art. (See, e.g., "Current Protocols in Molecular Biology," Ausubel et al. eds., John Wiley & Sons, 2010). DNA introduction may be followed by a selection method (e.g., antibiotic resistance) to select cells that contain the vector.

gH/gL/UL128/UL130/UL131A. Recombinant nucleic acid constructs were designed to produce a HHV protein complex comprising gH, gL, UL128, UL130, and UL131A. In one embodiment, the recombinant nucleic acid construct comprises a first nucleic acid encoding a HHV gH polypeptide, a second nucleic acid encoding a HHV gL polypeptide, a third nucleic acid encoding a HHV UL128 polypeptide, a fourth nucleic acid encoding a HHV UL130 polypeptide, and a fifth nucleic acid encoding a HHV UL131A polypeptide. In certain embodiments, a pentameric complex is formed when the recombinant nucleic acid is expressed in a host cell. In certain embodiments, none of the encoded polypeptides comprise a transmembrane domain or an intracellular domain. In certain embodiments, the recombinant nucleic acid comprises one or more internal ribosome entry cites (IRES) to facilitate expression of multiple proteins from a single transcript. In certain embodiments, the recombinant nucleic acid comprises a first IRES between the first and second nucleic acids, a second IRES between the second and third nucleic acids, and/or a third IRES between the fourth and fifth nucleic acids. In certain embodiments, the recombinant nucleic acid comprises one or more promoter sequences to facilitate expression of the HHV polypeptides. In certain embodiments the recombinant nucleic acid comprises a first promoter operatively linked to the first nucleic acid and a second promoter operatively linked to the third nucleic acid. In one embodiment, the promoter is a CMV promoter. In certain embodiments, the HHV is a betaherpesvirus subfamily member, including, for example, HCMV. A non-limiting, exemplary embodiment of such a recombinant nucleic acid is depicted in FIG. 13. Additional nucleic acid sequences can be included in such a nucleic acid sequence to aid in purification, such as a protein purification tag (e.g., his-tag sequences) or a leader sequence to promote secretion from the host cell (e.g., immunoglobulin kappa light chain leader sequences). In certain embodiments, the leader sequence is inserted in frame with each of the first, second, third, fourth, and fifth nucleic acid.

gH/gL/gO. Recombinant nucleic acid constructs were designed to produce a HHV complex comprising gH, gL, and gO. In one embodiment, the recombinant nucleic acid construct comprises a first nucleic acid encoding a HHV gH polypeptide, a second nucleic acid encoding a HHV gL polypeptide, a third nucleic acid encoding a HHV gO polypeptide. In certain embodiments, a trimeric complex is formed when the recombinant nucleic acid is expressed in a host cell. In certain embodiments, none of the encoded polypeptides comprise a transmembrane domain or an intracellular domain. In certain embodiments, the recombinant nucleic acid comprises one or more internal ribosome entry cites (IRES) to facilitate expression of multiple proteins from a single transcript. In certain embodiments, the recombinant nucleic acid comprises an IRES between the first and second nucleic acids. In certain embodiments, the recombinant nucleic acid comprises one or more promoter sequences to facilitate expression of the HHV polypeptides. In certain embodiments the recombinant nucleic acid comprises a first promoter operatively linked to the first nucleic acid and a second promoter operatively linked to the third nucleic acid. In one embodiment, the promoter is a CMV promoter. In certain embodiments, the HHV is a betaherpesvirus subfamily member, including, for example, HCMV. An exemplary embodiment of such a recombinant nucleic acid is depicted in FIG. 14. Additional nucleic acid sequences can be included in such a nucleic acid sequence to aid in purification, such as a protein purification tag (e.g., his-tag sequences) or a leader sequence (e.g., immunoglobulin kappa light chain leader sequences). In certain embodiments, the leader sequence is inserted in frame with each of the first, second and third nucleic acid.

Vaccine Compositions. The combinations of monomeric and/or multimeric HHV polypeptides and nucleic acids encoding the same that are described in this application provide an improved platform for developing a HHV vaccine.

Thus, one aspect is directed to an antigenic composition as described herein comprising two or more HHV fusion and host cell entry proteins (or nucleic acids encoding the same). In certain embodiments, the vaccine comprises virus like particles. In certain embodiments, the antigenic composition further comprises at least one pharmaceutically acceptable excipient, and optionally an adjuvant (hereinafter referred to as "vaccine composition"). In certain embodiments, the vaccine composition does not include an adjuvant.

In certain embodiments, the vaccine is a nucleic acid vaccine, comprising a nucleic acid encoding the two or more HHV fusion and host cell entry proteins. In certain embodiments, the nucleic acid vaccine is a DNA vaccine. In other embodiments, the nucleic acid vaccine is an RNA vaccine. In certain embodiments, the nucleic acid vaccine is a viral vector vaccine.

The pharmaceutically acceptable excipient can be chosen from, for example, diluents such as starch, microcrystalline cellulose, dicalcium phosphate, lactose, sorbitol, mannitol, sucrose, methyl dextrins; binders such as povidone, hydroxypropyl methylcellulose, dihydroxy propylcellulose, and sodium carboxylmethylcellulose; and disintegrants such as crospovidone, sodium starch glycolate, croscarmellose sodium, and mixtures of any of the foregoing. The pharmaceutically acceptable excipient can further be chosen from lubricants such as magnesium stearate, calcium stearate, stearic acid, glyceryl behenate, hydrogenated vegetable oil, glycerine fumerate and glidants such as colloidal silicon dioxide, and mixtures thereof. In some embodiments, the pharmaceutically acceptable excipient is chosen from microcrystalline cellulose, starch, talc, povidone, crospovidone, magnesium stearate, colloidal silicon dioxide, sodium dodecyl sulfate, and mixtures of any of the foregoing. The excipients can be intragranular, intergranular, or mixtures thereof.

The vaccine composition can be formulated as freeze-dried or liquid preparations according to any means suitable in the art. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form. After formulation, the vaccine composition can be incorporated into a sterile container which is then sealed and stored at a low temperature (e.g., 4° C.), or it can be freeze dried.

The vaccine composition can be formulated in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccine composition can optionally comprise agents that enhance the protective efficacy of the vaccine, such as adjuvants. Adjuvants include any compound or compounds that act to increase an immune response to the two or more HHV fusion and host cell entry proteins, thereby reducing the quantity of proteins (or nucleic acid encoding the same) necessary in the vaccine, and/or the frequency of administration necessary to generate a protective immune response. Adjuvants can include for example, emulsifiers, muramyl dipeptides, avridine, aqueous adjuvants such as aluminum hydroxide, chitosan-based adjuvants, and any of the various saponins, oils, and other substances known in the art, such as Amphigen, LPS, bacterial cell wall extracts, bacterial DNA, CpG sequences, synthetic oligonucleotides and combinations thereof (Schijns et al. (2000) *Curr. Opin. Immunol.,* 12:456), Mycobacterial *phlei* (*M. phlei*) cell wall extract (MCWE) (U.S. Pat. No. 4,744,984), *M. phlei* DNA (M-DNA), and *M. phlei* cell wall complex (MCC). Compounds which can serve as emulsifiers include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrimethylammonium bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (FCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed *Mycobacterium* sp.

Immunomodulatory cytokines can also be used in the vaccine compositions to enhance vaccine efficacy, for example, as an adjuvant. Non-limiting examples of such cytokines include interferon alpha (IFN-α), interleukin-2 (IL-2), and granulocyte macrophage-colony stimulating factor (GM-CSF), or combinations thereof.

The vaccine composition can be prepared using techniques well known to those skilled in the art including, but not limited to, mixing, sonication and microfluidation. The adjuvant can comprise from about 10% to about 80% (v/v) of the vaccine composition, more preferably about 20% to about 50% (v/v), and more preferably about 20% to about 30% (v/v), or any integer within these ranges.

The vaccine composition can be administered to any animal, and preferably is a mammal such as a human, mouse, rat, hamster, guinea pig, rabbit, cat, dog, monkey, cow, horse, pig, and the like. Humans are most preferred.

Administration of the vaccine composition can be by infusion or injection (e.g., intravenously, intramuscularly, intracutaneously, subcutaneously, intrathecal, intraduodenally, intraperitoneally, and the like). The vaccine composition can also be administered intranasally, vaginally, rectally, orally, intratonsilar, or transdermally. Additionally, the vaccine composition can be administered by "needle-free" delivery systems.

The effective amount of the vaccine composition may be dependent on any number of variables, including without limitation, the species, breed, size, height, weight, age, overall health of the patient, the type of formulation, or the mode or manner or administration. The appropriate effective amount can be routinely determined by those of skill in the art using routine optimization techniques and the skilled and informed judgment of the practitioner and other factors evident to those skilled in the art. Preferably, a therapeutically effective dose of the vaccine composition described herein will provide the therapeutic preventive benefit without causing substantial toxicity to the subject.

The vaccine composition can be administered to a patient on any schedule appropriate to induce and/or sustain an immune response against the two or more HHV fusion and host cell entry proteins. For example, patients can be administered a vaccine composition as a primary immunization as described and exemplified herein, followed by administration of a secondary immunization, or booster, to bolster and/or maintain protective immunity.

The vaccine administration schedule, including primary immunization and booster administration, can continue as long as needed for the patient, for example, over the course of several years, to over the lifetime of the patient. The frequency of primary vaccine and booster administration and dose administered can be tailored and/or adjusted to meet the particular needs of individual patients, as determined by the administering physician according to any means suitable in the art.

The vaccine composition may be administered prophylactically (before exposure to the antigen or pathogen of interest) or therapeutically (after exposure to the antigen or pathogen of interest).

Methods of Inducing an Immune Response. In another aspect, two or more HHV fusion and host cell entry proteins (or nucleic acid encoding the same) can be used in a method of inducing an immune response or otherwise treating or preventing a HHV infection in a subject. The immune response can be induced in a naïve subject who has not previously been exposed to HHV. Alternatively, the immune response can be induced in a subject who has been previously exposed to HHV and used to enhance an existing immune response.

In one embodiment, the method of inducing an immune response comprises administering to a subject two or more HHV fusion and host cell entry proteins, as described herein, in an amount sufficient to induce an immune response against the two or more HHV fusion and host cell entry proteins in the subject. In another embodiment, the method of inducing an immune response comprises administering to a subject one or more nucleic acid constructs encoding the two or more HHV fusion and host cell entry proteins, as described herein, in an amount sufficient to induce an immune response against the two or more HHV polypeptides in the subject. In certain embodiments, the method induces an additive antibody response to the two or more HHV fusion and host cell entry proteins. In certain embodiments, the method induces a synergistic antibody response to the two or more HHV fusion and host cell entry proteins.

In these methods of inducing an immune response, the immune response can be measured using routine methods in the art, such as those disclosed in this application. These routine methods include, but are not limited to, measuring an antibody response, such as an antibody response directed against an HHV protein, and measuring cellular proliferation, including, for example, by measuring tritiated thymidine incorporation or cytokine (e.g., IFN-γ) production.

In certain embodiments, the method of treating or preventing an HHV infection comprises administering to a subject a therapeutically effective amount of two or more HHV polypeptides, as described herein, or one or more nucleic acid constructs encoding the same.

In these methods that comprise a step of administering two or more HHV fusion and host cell entry proteins, the proteins can be administered simultaneously or sequentially. In certain embodiments, the HHV proteins that make up the antigenic compositions disclosed herein are administered simultaneously (concomitantly), for example, as part of the same composition or as part of different compositions administered at the same time. In other embodiments, the HHV proteins that make up the antigenic compositions disclosed herein are administered separately (sequentially), for example, administered as individual compositions at different times. That is, the at least two HHV polypeptides in the compositions can be simultaneously or separately administered to achieve the effects disclosed herein. Further, compositions can be administered in one or more doses to achieve the desired result.

Typically, the subject is a human. In certain embodiments, the subject is at risk of developing PTLD following a transplant, such as a hematopoietic stem cell or solid organ transplant. In certain embodiments, the subject suffers from a primary immunodeficiency syndrome, including, for example, AIDS. In certain embodiments, the subject is at risk of developing nasopharynegeal carcinoma. In certain embodiments, the subject has nasopharyngeal carcinoma.

Subjects in some embodiments concurrently receive one or more of an anti-CD20 antibody, anti-viral therapy, interferon alpha, radiotherapy, and/or chemotherapy. CD-20 antibody therapy and related biologics are known in the art, as are radiotherapy and chemotherapy. Any of the known therapy regimens of these categories can be concurrently administered to the subject in need thereof.

Passive Immunotherapy and Adoptive Transfer of Cell-Mediated Immunity. Passive immunotherapy methods for various indications are known in the art and have been employed in various forms for over 120 years. (See, Waldman, T. A., *Nature Medicine,* 9(3):269-277, 2003; and Chippeaux et al., *J. Venom. Anim. Toxins Incl. Trop. Dis.,* 21:3, 2013; see also Casadevall et al., *Clin. Infect. Dis.,* 21(1):150-61, 1995). The benefits of passively transferring antibodies for inflammation, immune deficiency, acute and chronic autoimmune diseases, and cancer is well established. (Kivity et al., *Clin. Rev. Allergy Immunol.,* 38:201-69, 2010; and Toubi et al., *Clin. Rev. Allergy Immunol.,* 29:167-72, 2005). Studies have documented multifunctional mechanisms of passively transferred antibodies, including mediation of humoral and cellular immune responses through both its Fab and Fc portions with neutralization and enhanced clearance of pathogens. Passive immunotherapy is also sometimes referred to optionally as cell transfer therapy, immunoglobulin therapy, antiserum therapy, passive transfer, or passive immunity. When immune cells are the immune components or neutralizing agent administered to the subject in need thereof, the method is often referred to as adoptive transfer, adoptive cellular therapy (ACT), or adoptive immunotherapy.

In passive immunotherapy, antibodies (or immunoglobulins) or other immune system components, i.e., agents that possess antigen neutralizing activity, such as immune cells, are made outside of the subject being administered these components, typically made in a laboratory and/or produced ex vivo by a second subject (or several other subjects). In some embodiments, the immune system component administered to the subject is a monoclonal antibody. In other embodiments, the immune component is a polyclonal antibody. In still other embodiments, the immune component is one or more immune cells. In all instances, the immune component includes antibodies or cells that specifically recognize a target antigen, such as a target antigen present on an HHV fusion and host cell entry protein.

Having shown that various combinations of HHV fusion and host cell entry proteins induce high-titer neutralizing antibodies, it was contemplated that such high-titer neutralizing antibodies could be used to passively transfer immunity against HHV. Thus, antibodies generated by a subject who was immunized with two or more HHV fusion and host cell entry proteins, as described herein, can be harvested from the subject and isolated. The donor subject can be immunized with any combination of HHV (e.g., EBV, HCMV, HSV-1 or HSV-2, VZV, HHV-6, HHV-7, or KSVH) fusion and host cell entry proteins as described herein to induce the high-titer anti-HHV antibodies.

In an EBV passive immunization or adoptive transfer embodiment, a donor subject is immunized with, for example, a tetrameric EBV gp350 protein and the induced high-titer neutralizing antibodies obtained therefrom are employed in a passive transfer of immunity to an acceptor subject who benefits therefrom. In a further EBV embodiment, a donor subject is immunized with, for example, a trimeric EBV gH/gL protein and the induced high-titer neutralizing antibodies obtained therefrom are employed in a passive transfer of immunity to an acceptor subject who benefits therefrom. In another exemplary EBV embodiment, a donor subject is immunized with, for example, a trimeric gB protein and the induced high-titer neutralizing antibodies obtained therefrom are employed in a passive transfer of immunity to an acceptor subject who benefits therefrom.

In an HCMV passive immunization or adoptive transfer embodiment, a donor subject is immunized with, for example, a trimeric HCMV gB protein and the induced high-titer neutralizing antibodies obtained therefrom are employed in a passive transfer of immunity to an acceptor subject who benefits therefrom. In a further HCMV embodiment, a donor subject is immunized with, for example, a trimeric HCMV gH/gL protein and the induced high-titer neutralizing antibodies obtained therefrom are employed in a passive transfer of immunity to an acceptor subject who benefits therefrom.

In an HSV passive immunization or adoptive transfer embodiment, a donor subject is immunized with, for example, a trimeric HSV gB protein and the induced high-titer neutralizing antibodies obtained therefrom are employed in a passive transfer of immunity to an acceptor subject who benefits therefrom. In a further HSV embodiment, a donor subject is immunized with, for example, a trimeric HSV gH/gL protein and the induced high-titer neutralizing antibodies obtained therefrom are employed in a passive transfer of immunity to an acceptor subject who benefits therefrom.

In a VZV passive immunization or adoptive transfer embodiment, a donor subject is immunized with, for example, a trimeric HSV gB protein and the induced high-titer neutralizing antibodies obtained therefrom are employed in a passive transfer of immunity to an acceptor subject who benefits therefrom. In a further VZV embodiment, a donor subject is immunized with, for example, a trimeric VZV gH/gL protein and the induced high-titer neutralizing antibodies obtained therefrom are employed in a passive transfer of immunity to an acceptor subject who benefits therefrom.

In a KSHV passive immunization or adoptive transfer embodiment, a donor subject is immunized with, for example, a trimeric KSHV gB protein and the induced high-titer neutralizing antibodies obtained therefrom are employed in a passive transfer of immunity to an acceptor subject who benefits therefrom. In a further KSHV embodiment, a donor subject is immnunized with, for example, a trimeric KSHV gH/gL protein and the induced high-titer neutralizing antibodies obtained therefrom are employed in a passive transfer of immunity to an acceptor subject who benefits therefrom.

Immunization with the two or more HHV fusion and host cell entry proteins can be simultaneous, in multiple doses, or in staggered doses, as long as the desired neutralizing activity is obtained in the donor subject. These antibodies induced in the donor subject can then be administered to another subject in need thereof. Alternatively, the high-titer neutralizing antibodies against the HHV fusion and host cell entry proteins can be obtained from one or more blood, serum, or plasma samples that have been selected for the high-titer antibodies. In certain embodiments, the one or more blood, serum, or plasma samples are obtained from a human donor.

The immune components can also be obtained synthetically, as in monoclonal antibodies, produced in tissue culture or by animals, or can be obtained from another, donor, subject who is either seropositive for immune components specifically recognizing the desired antigen, or who has been exposed to the antigen and thereby has developed seropositivity. In certain embodiments, the donor subject possesses a high degree of responsiveness to the antigen, i.e., possess a high concentration, or high titer, of the antigen-neutralizing immune components (e.g., antibodies or immune cells). These immune components are then extracted from the donor subject, or obtained from tissue culture or animals, purified or otherwise manipulated in the laboratory as needed to avoid possible graft vs. host reactions or other adverse reactions, and then administered to the subject in need thereof.

Steps for implementing a passive immunotherapy or adoptive transfer protocol or methodology involve, in some embodiments, first identifying a donor subject possessing a high neutralizing activity against HHV. In certain embodiments, high titer anti-HHV antibodies or immune cells are obtained from blood, serum, and/or plasma samples collected from the donor subject. These immune components are then transferred to a second subject in need thereof, in order to induce an immunoprotective effect in the second subject, thereby preventing or treating an HHV infection. The second subject can be infected with an HHV, or susceptible to infection with HHV. The antibodies can be optionally extracted and/or purified prior to administration to the subject in need thereof. Further, in other embodiments, optionally the donor subject is histocompatible with the subject in need thereof, such that blood, serum, and/or plasma may be administered to the subject in need thereof. In some embodiments, the blood, serum, and/or plasma is obtained from a human donor.

The term "high-titer" as used herein, refers to an antibody having a titer specific for the desired HHV polypeptide in an amount that is 2-fold, 3-fold, 4-fold, 5-fold, 6-fold, 7-fold, 8-fold, 9-fold, 10-fold, 12-fold, 14-fold, 16-fold, 18-fold, 20-fold, 25-fold, or in some embodiments, as much as 30-fold higher than an average titer from unselected plasma, serum, or blood samples from a general population of donor subjects and that comprises antibodies possessing the same specificity. In certain embodiments, the donor subject has been exposed to the HHV polypeptide antigen and is not seronegative or naïve. In certain embodiments, the donor subject, or donor subjects, has/have been administered two or more of the HHV fusion and host cell entry proteins, in order to generate a high-titer antibody response in the donor subject(s). High-titer antibodies can be identified or selected using the methods described in this application (e.g., Raji B cell neutralization assay or a HeLa cell neutralization assay) or any known method in the art. Antibody titers can be determined by various art-recognized screening methods or by the methods disclosed in this application. In one embodiment, high-titer antibodies are identified or selected using a Raji B cell neutralization assay or a HeLa cell neutralization assay, as described, for example, in the examples of this application. In certain embodiments, the HeLa cell neutralization assay comprises, infecting HeLa cells with labeled EBV (e.g., EBV with a fluorescent label, such as green fluorescent protein) to yield EBV-infected HeLa cells, incubating the blood, plasma or serum sample with the EBV-infected HeLa cells, analyzing the neutralization activity of the blood, plasma, or serum sample (e.g., using flow cytometry or an ELISpot assay) and optionally calculating the $IC_{50}$ of the blood, plasma, or serum sample.

The subject in need thereof is a subject who is naïve (seronegative for HHV), immunocompromised, or otherwise susceptible to infection, or already infected with one or more HHV. In certain embodiments, the subject is administered high titer anti-EBV antibodies and is at risk of developing post-transplantation lymphoproliferative disorder (PTLD) following hematopoietic stem cell or solid organ transplantation, or has or is at risk of developing nasopharyngeal carcinoma (NPC), Burkitt lymphoma, Hodgkin's lymphoma, non-Hodgkin's lymphoma, gastric carcinoma, severe infectious mononucleosis, chronic active EBV infection, multiple sclerosis, systemic lupus erythematosus, or rheumatoid arthritis. In certain embodiments, the subject is at risk of developing PTLD, for example, following hematopietic stem cell or solid organ transplant. In certain embodiments, the subject is at risk of developing nasopharyngeal carcinoma.

In another embodiment, the subject is administered high titer anti-HCMV antibodies and is a pregnant woman, a transplantation patient, a patient who is immunosuppressed during chemotherapy or radiotherapy, or a patient infected with human immunodeficiency virus (HIV). In another embodiment, the subject is administered high titer anti-HSV-1 or HSV-2 antibodies and is at risk of developing encephalitis caused by HSV-1 or HSV-2 infection, or is a pregnant woman with active HSV-2 or HSV-1 infection and/or HSV encephalitis. In another embodiment, the subject is administered high titer anti-ZVZ antibodies and is at risk of developing Zoster (shingles) or Varicella (chickenpox). In a further embodiment, the subject is administered high titer anti-KSHV antibodies and is at risk of developing KSHV-associated Kaposi's sarcoma, primary effusion lymphoma, multicentric Cattleman's disease, KSHV-associated inflammatory cytokine syndrome, or KSHV immune reconstitution inflammatory syndrome.

In another embodiment, the subject in need thereof is concurrently receiving anti-viral therapy, anti-CD20 antibody compositions, interferon-alpha, radiotherapy, and/or chemotherapy.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Examples

1. Epstein Bar Virus (EBV)

Example 1.1—Production of EBV gH and EBV gL Polypeptides

To recombinantly produce EBV gH and gL polypeptides, coding sequences for EBV gH and gL were downloaded from the NCBI website, reference sequence NC_009334.1, including EBV gH nucleotides 129454 through 131574, and EBV gL nucleotides 98500 through 98913. The gL sequence encoding amino acids 23-137 was used, and the signal peptide at amino acids 1-22 was replaced with an IgG κ leader sequence. The gH sequence coding corresponding to amino acids 19-678 was linked to the 3' end of the gL sequence and separated by a 15-amino acid linker $(Gly_4Ser)_3$ (SEQ ID NO: 3) sequence. (See representative schematic in FIG. 1). A foldon trimerization domain coding sequence derived from T4 phage fibritin (see e.g., U.S. Pat. Nos. 6,911,205; 8,147,843, and WO 01/19958) was linked to the 3' end of gH, followed by a His6 (SEQ ID NO: 49) coding sequence. DNA coding for the trimeric gH/gL was synthesized and cloned into the vector pOptiVEV (Invitrogen, Carlsbad, CA, USA), and the sequence verified by sequencing. The monomeric EBV gH/gL construct was made by PCR amplification of EBV gH/gL without the foldon trimerization coding sequence, and cloned into pOptiVEV. The sequence was verified by sequencing.

Chinese Hamster Ovary (CHO) cells (strain DG44, Invitrogen, Carlsbad, CA, USA) were transfected with the resultant pOptiVEV-gH/gL constructs and positive cells were selected with gradually increased concentrations of methotrexate (MTX), up to 4 μM. Selected CHO cells were loaded into "Fibercell" cartridges (FiberCell Systems, Frederick, MD, USA) for protein production. Supernatants were concentrated and purified using cobalt affinity purification (Thermo Fisher Scientific, Waltham, MA, USA). Recombinant proteins were further purified by size exclusion chromatography using Sephadex® G200 column or Superose® 6 Increase 10/300 GL column (GE Healthcare, Little Chalfont, UK).

Figure 2A:
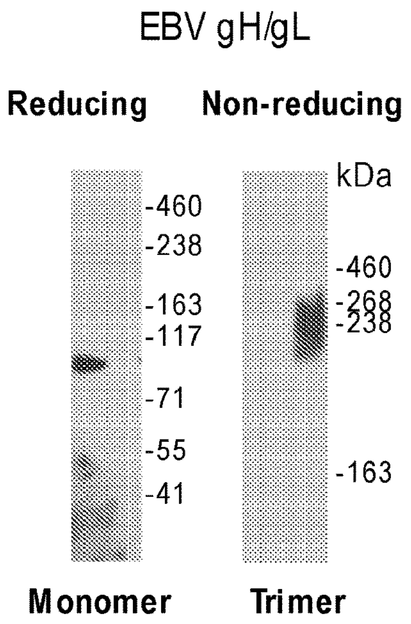
FIGS. 2A-C show images of a Western blot of monomeric and multimeric EBV gH/gL (FIG. 2A), EBV gB (FIG. 2B), and EBV gp350 (FIG. 2C) polypeptides.

Western blot analysis of trimeric gH/gL polypeptides using an anti-His6 (SEQ ID NO: 49) mAb or an anti-EBV gH/gL mAb (clone E1D1, gift from Dr. L. M. Hutt-Fletcher, Louisiana State University Health Sciences Center, Shreveport, LA, USA), under reducing conditions that disrupt the native oligomers, revealed a molecular weight (MW) band of about 90 kiloDaltons (kDa), consistent with the predicted size of monomeric gH/gL (FIG. 2A). Under non-reducing conditions, a MW band of about 270 kDa was observed, consistent with predicted size of trimeric gH/gL (FIG. 2A).

Example 1.2—Production of EBV gB Polypeptides

To recombinantly produce EBV gB polypeptides, the coding sequence for EBV gB was downloaded from the NCBI website, corresponding to reference sequence NC_009334.1, nucleotides 157775 through 160348. The sequence encoding the extracellular domain of EBV gB (amino acids 23-732 of wild type EBV) was used to design the construct for trimeric gB expression. The signal peptide, corresponding to amino acids 1-22, was replaced with an IgG κ leader sequence, and the coding sequence of the furin cleavage site (RRRRD) (SEQ ID NO: 50) between amino acids 427 (L) and 434 (A) was replaced with a 15-amino acid $(Gly_4Ser)_3$ (SEQ ID NO: 3) linker sequence (FIG. 1). A $His_6$ (SEQ ID NO: 49) sequence was linked to the 3' end for protein purification. All the following steps were as described above for EBV gH/gL.

Figure 2B:
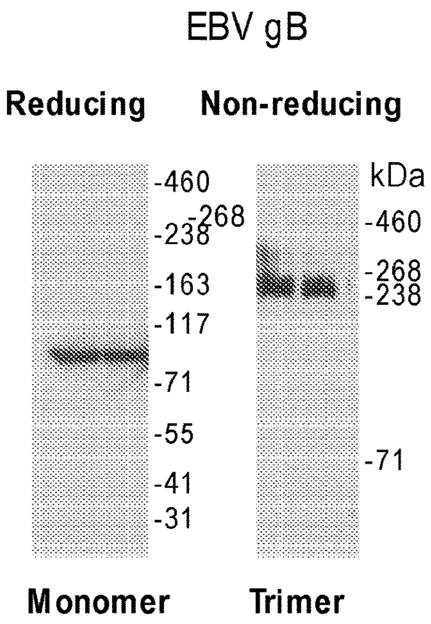

Western blot analysis under fully reducing conditions using an anti-$His_6$ (SEQ ID NO: 49) mAb or an anti-gB mAb (Virusys Corp., Taneytown, MD, USA) demonstrated that the EBV gB protein was the predicted size of the monomeric form (about 80 kDa) (FIG. 2B). Under modified non-reducing conditions that allows for detection of the native form of EBV gB protein, a uniform band with the predicted size of a trimeric EBV gB (about 240 kDa) was observed (FIG. 2B).

Example 1.3—Production of EBV Gp350 Polypeptides

EBV gp350 polypeptides were expressed as previously described (see, Cui et al., Vaccine, 31:3039-45, 2013; see also WO 2014/018858, which is hereby incorporated by reference in its entirety). Briefly, an EBV monomeric gp350 construct was made by PCR amplification of the gp350 cDNA, strain B95-8. A sequence encoding amino acids 1-470 was cloned with an IgG κ leader sequence added to the 5' end and $His_6$ (SEQ ID NO: 49) coding sequence added to the 3' end. The tetrameric gp350 construct was made by ligation of a second gp350 fragment (1-470) to the 3' end of the monomeric gp350 construct (without $His_6$ (SEQ ID NO: 49)). The second gp350 fragment has a $(Gly_4Ser)_3$ (SEQ ID NO: 3) linker at the 5' end and a leucine zipper sequence at the 3' end for homodimerization, followed by $His_6$ (SEQ ID NO: 49) sequence for protein purification (FIG. 1). Monomeric and tetrameric gp350 DNA were cloned into pOptiVEV, and their sequences verified by sequencing. All of the following steps were as described above for EBV gH/gL.

Figure 2C:
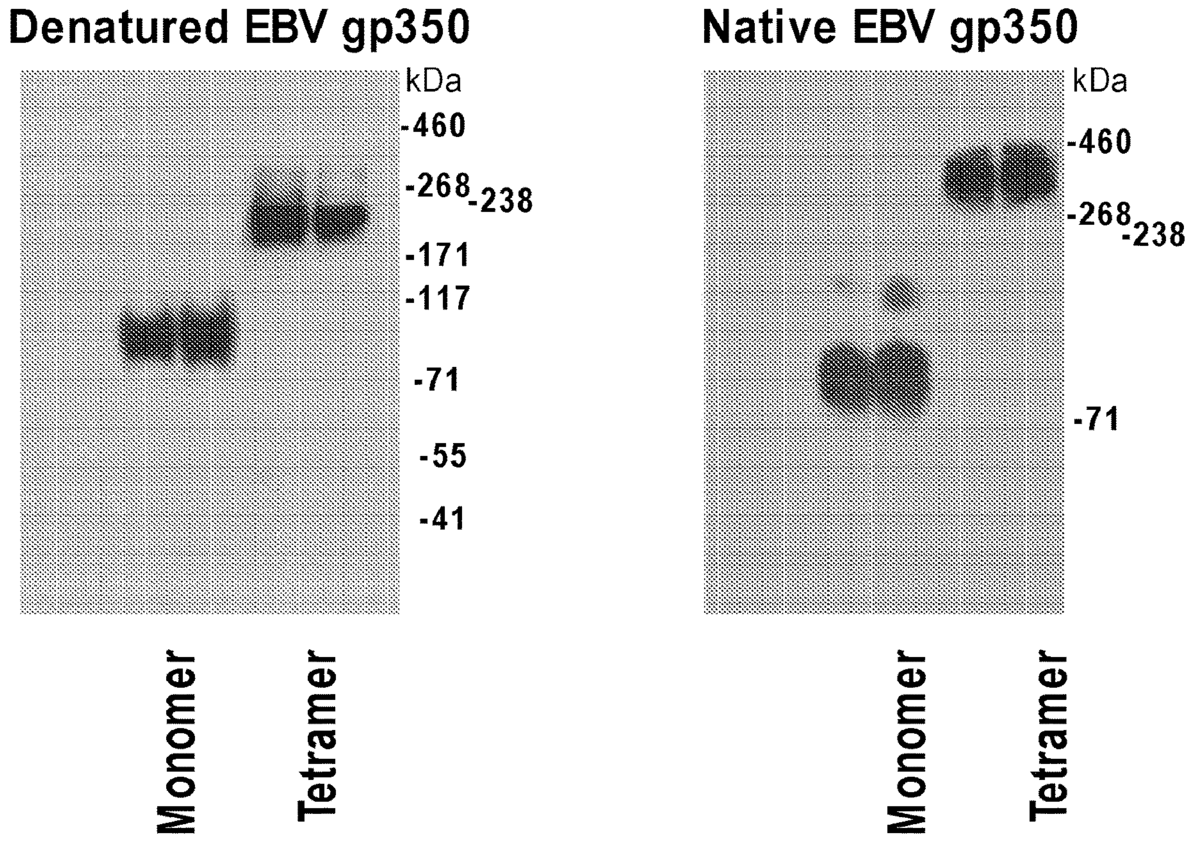

Western blot analysis using anti-gp350 mAbs, clone 2L10 (Merck Millipore, Billerica, MA, USA), 72A1 (ATCC, Manassas, VA, USA), or an anti-His6 (SEQ ID NO: 49) mAb, under denatured (reducing) condition, revealed a single ~100 kDa band corresponding to monomeric gp350, and a single band at about 200 kDa consistent with a gp350 dimer, resulting from the dissociation of the two gp350 dimers that form the tetrameric gp350 (FIG. 2C). Under native (non-reducing) condition, a single band at about 100 kDa was revealed, consistent with monomeric gp350, and a single band at about 400 kDa was observed, consistent with the tetrameric gp350 (FIG. 2C).

Example 1.4—Induction of EBV Immune Response in Rabbits

The obtained EBV polypeptides were examined in vaccine preparations for their ability to induce an immune response in rabbits. In this study and the example following this example, the level of immune response was determined by the level of EBV polypeptide-specific antibodies found in serum. In this study, groups of five male New Zealand white rabbits, 12 to 15 weeks old, were immunized subcutaneously with 25 μg of each of the EBV antigens, including tetrameric EBV gp350, trimeric EBV gH/gL, or trimeric EBV gB, versus monomeric EBV gp350, or monomeric EBV gH/gL. The antigens were adsorbed to aluminum hydroxide (alum;

0.25 μg alum/mg of protein) and mixed with 50 ag of a 12-mer phosphorothioate-modified CpG oligodeoxynucleotide (ODN) with optimization for use in rabbits (hereinafter, ODN 2007, TCGTCGTTGTCGTTTTGTCGTT (SEQ ID NO: 51)) prior to injection (see, Ioannou et al., Vaccine, 21:4368-72, 2003). The activity of ODN 2007 was confirmed by its ability to stimulate IgM secretion when added to rabbit splenocytes (Id.). Rabbits immunized with alum and CpG-ODN alone served as the negative control. Rabbits were immunized on day 0, day 21, and day 42. Serum samples were taken before initial immunization, and 10 days following each immunization.

Figure 3:
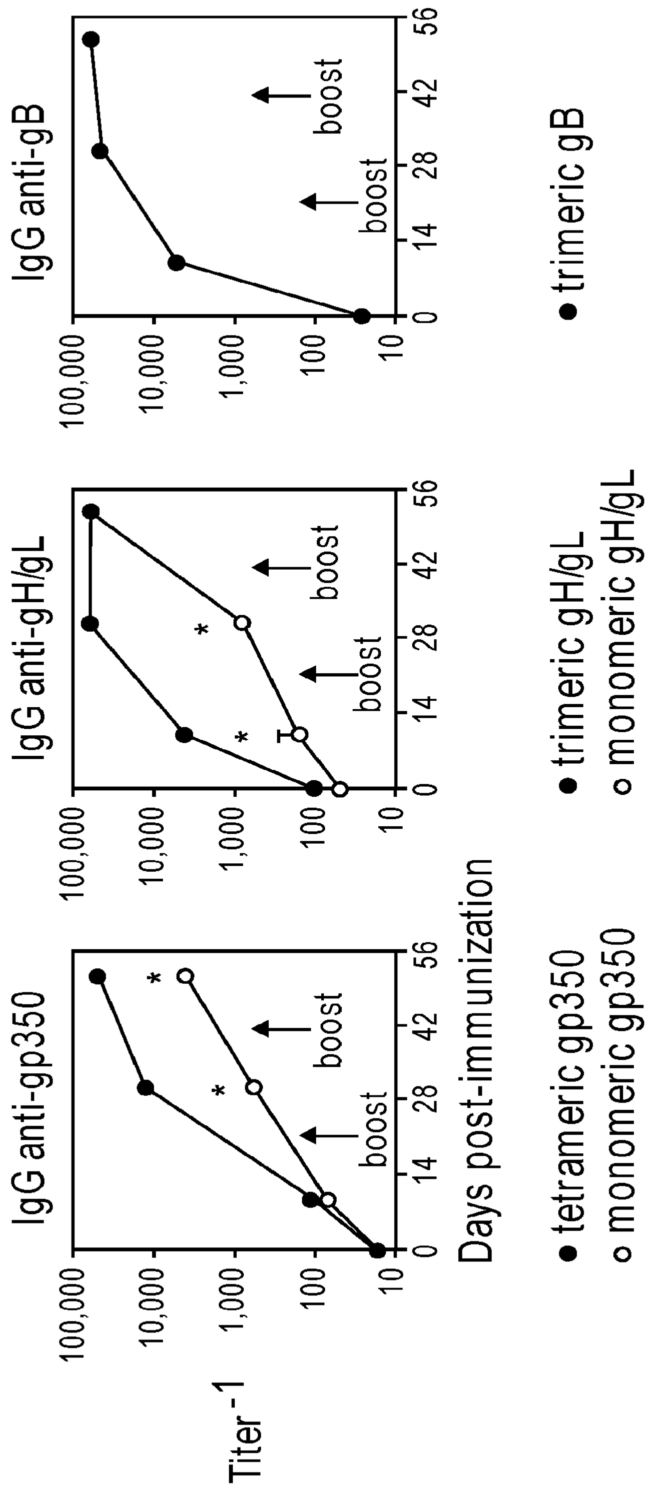
FIG. 3 shows EBV in vitro neutralization analysis of the sera from rabbits immunized with gp350 monomer (left panel, open circles), gp350 tetramer (left panel, closed circles), gB trimer (right panel), gH/gL monomer (middle panel, open circles), and gH/gL trimer (middle panel, closed circles).

Sera were obtained 10 days after the last immunization for measurement of $IC_{50}$ neutralization titers in cultures of Raji B lymphoma cells and green fluorescent protein (GFP)-labeled EBV. $IC_{50}$ values shown in FIG. 3 represent the reciprocal serum titer that generates 50% EBV neutralization. EBV infection was measured by flow cytometry. As illustrated in FIG. 3, tetrameric gp350 and trimeric gH/gL elicited significantly (*$p<0.05$) higher $IC_{50}$ titers than their monomeric counterparts. Of note, significant differences ($p<0.05$) in $IC_{50}$ titers were also observed among the multimeric proteins with gH/gL ($IC_{50}$=506)>gB ($IC_{50}$=89)>gp350 ($IC_{50}$=22).

Thus, as illustrated in FIG. 3, each of the five EBV polypeptides induced augmented IgG responses following the first booster immunization, including monomeric gp350 (FIG. 3, left panel, open circles) and monomeric gH/gL (FIG. 3, middle panel, open circles). Further significant augmentation in serum IgG titers followed the second booster immunization. Tetrameric EBV gp350 (FIG. 3, left panel, closed circles) induced >20-fold serum gp350-specific IgG titers relative to monomeric EBV gp350 (FIG. 3, left panel, open circles) following the first and second booster immunizations. Trimeric EBV gH/gL (FIG. 3, middle panel, closed circles) induced greater than 30-fold and greater than 90-fold increases in serum gH/gL-specific IgG titers following the primary immunization and the first booster immunization, respectively, with the titers equalizing by the second booster immunization. These data are consistent with a previous study performed in mice using tetrameric and monomeric gp350 (Cui et al., Vaccine, 31:3039-45, 2013), that showed that multimerization of tetrameric fusion EBV gp350 polypeptides induce marked increases in immunogenicity.

Example 1.5—EBV Antibody Titers Induced by Monomeric gH/gL, Trimeric gH/gL, and Trimeric gB, as Compared to Titers Induced by Monomeric and Tetrameric Gp350

Determination of serum in vitro EBV-neutralizing titers, using Raji cells (EBV-positive human Burkitt lymphoma cell line), were performed as described (Sashihara et al., *Virology,* 391:249-56, 2009). Briefly, GFP-EBV (B95-8/F) was prepared by transfection of 293/2089 cells with plasmids p509 and p2670 expressing EBV BZLF1 and EBV BALF4, respectively (gift from Dr. Jeffrey I. Cohen, N.I.H., Bethesda, MD, USA) (Neuhierl et al., *Proc. Natl. Acad. Sci. U.S.A.,* 99:15036-41, 2002; and Delecluse et al., *Proc. Natl. Acad. Sci. U.S.A,* 95:8245-50, 1998). Serial serum dilutions were mixed for 2 h with GFP-EBV in 96-well plates, followed by addition of Raji cells for 1 additional hour. Cells were then washed and re-cultured in medium alone for 3 days, fixed in paraformaldehyde and analyzed by flow cytometry for GFP+Raji cells. The serum dilution that inhibited infectivity by 50% ($IC_{50}$), based on reduction of the number of GFP+ cells, was calculated by non-linear regression analysis using Prism 6 software (GraphPad Software, Inc., La Jolla, CA, USA). An EBV-neutralizing anti-gp350 mAb (72A1) was used as a positive control. Pre-immune sera and sera from rabbits immunized with alum+CpG-ODN alone served as negative controls. For determination of serum neutralizing titers using peripheral blood naïve human B cells, naïve human B cells isolated from peripheral blood of healthy donors were incubated with GFP-EBV and cultured in RPM1 1640 medium containing 100 ng/ml LL-4 (BioLegend, San Diego, CA, USA) and 1 μg/ml CD40 antibody (R&D Systems, Minneapolis, MN, USA).

Figure 4A:
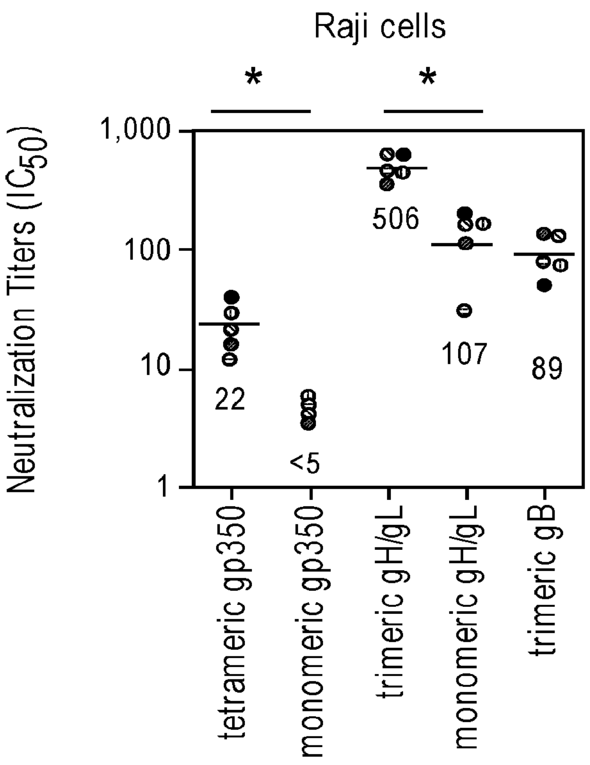
FIGS. 4A-B show neutralization titers of serum from rabbits immunized with monomeric or tetrameric EBV gp350, monomeric or trimeric EBV gH/gL, or trimeric EBV gB in alum+CpG-ODN adjuvant in either Raji cells (FIG. 4A) or naïve peripheral blood human B cells (FIG. 4B).
Figure 4B:
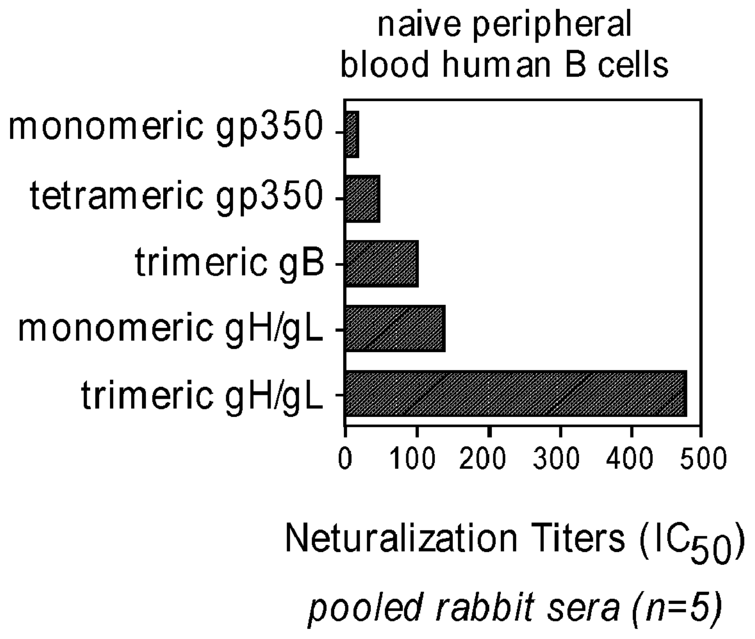

As illustrated in FIG. 4A, tetrameric EBV gp350 induced significantly higher $IC_{50}$ titers (the effective dilution of antibody that inhibited infectivity by 50%) than monomeric EBV gp350 ($IC_{50}$22 versus less than 5, respectively). Of note, trimeric gH/gL induced significantly higher $IC_{50}$ titers than monomeric gH/gL ($IC_{50}$ 506 versus 107, respectively), titer levels that are markedly and significantly higher than that induced by tetrameric gp350. Similarly, trimeric EBV gB induced significantly higher $IC_{50}$ titers ($IC_{50}$ 89) than tetrameric gp350 ($IC_{50}$ 22) and was comparable to that elicited by monomeric gH/gL ($IC_{50}$ 107). Compared to monomeric gp350, which has been previously tested in a phase II clinical trial, trimeric gH/gL, monomeric gH/gL, trimeric gB, and tetrameric gp350 elicited greater than 100-, 20-18-, and 4-fold higher $IC_{50}$ titers respectively. Similar data was obtained from sera that were pooled from each of the groups shown in FIG. 4A, utilizing GFP-EBV and naïve peripheral blood human B cells from healthy donors for determination of EBV neutralization titers (FIG. 4B), except that monomeric and tetrameric gp350 showed slightly higher $IC_{50}$ titers compared to those calculated using Raji cells (FIG. 4A). Thus, EBV gH/gL and EBV gB proteins, like EBV gp350, elicit antibodies in rabbits that block EBV entry into Raji Burkitt lymphoma and naïve peripheral human B cells. However, EBV gH/gL and EBV gB proteins appear to be significantly more potent on a per weight basis than EBV gp350.

Figure 5:
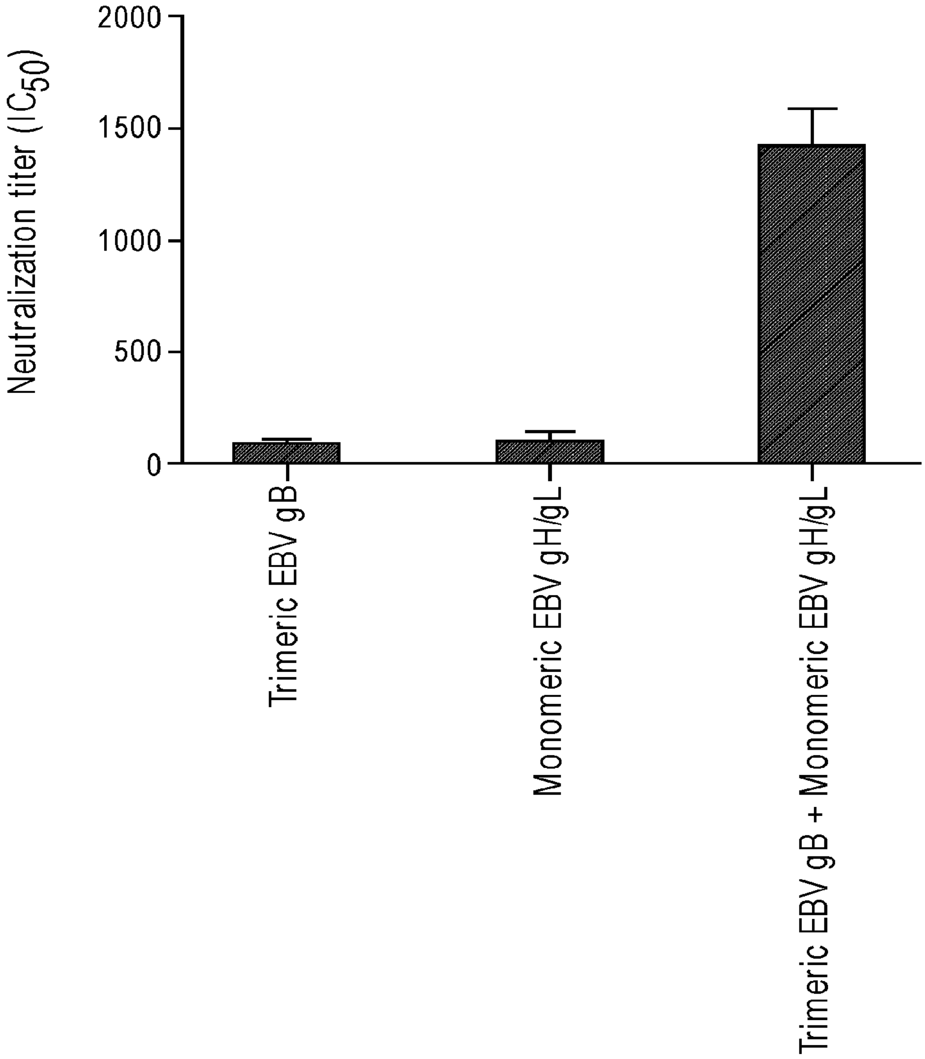
FIG. 5 shows EBV neutralization activity of immune sera from rabbits immunized with trimeric EBV gB or monomeric EBV gH/gL or the synergistic combination of trimeric EBV gB and monomeric EBV gH/gL.

Example 1.6—Immunization of Rabbits with EBV Trimeric gB and Monomeric gH/gL New Zealand white rabbits, 12-15 weeks old, were immunized subcutaneously with a combination of EBV trimeric gB and monomeric gH/gL, each 25 μg adsorbed to aluminum hydroxide (alum; 0.25 μg alum/mg protein) and mixed with 100 μg of a 12-mer phosphorothioate-modified CpG-ODN (TCATAACGTTCC (SEQ ID NO: 52)) optimized for rabbits (loannou et al., Vaccine, 21:4368-72, 2003). Rabbits were immunized on day 0, day 21, and day 42, and serum samples were taken before initial immunization, and 10 days following each immunization. EBV neutralization assay based on flow cytometric analysis of GFP-labeled EBV entry into Raji Burkitt lymphoma B cells was used to measure serum EBV neutralizing titers that inhibit infectivity of 50% of Raji B cells ($IC_{50}$). Administering both EBV trimeric gB and monomeric gH/gL yielded synergistic results as compared to administering the individual EBV proteins. More specifically, at day 52, rabbits immunized with the EBV trimeric gB and monomeric gH/gL demonstrated 16-fold and 14-fold higher EBV neutralization activity compared to the rabbits immunized with EBV trimeric gB or monomeric gH/gL alone, respectively (FIG. 5).

Example 1.7—EBV Neutralization In Vitro with Anti-Sera Combinations

Figure 6A:
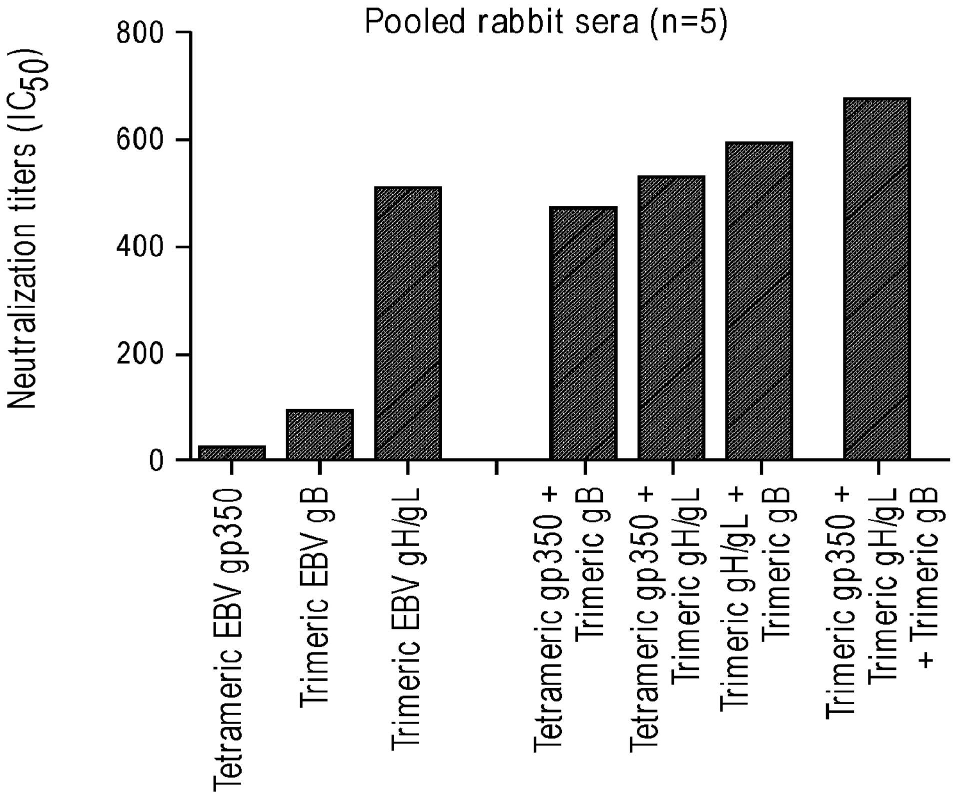
FIGS. 6A-B show EBV neutralization activity of pooled immune sera from rabbits (n=5) immunized with tetrameric EBV gp350, trimeric EBV gB, trimeric EBV gH/gL, or combinations thereof (FIG. 6A) demonstrating synergism, or with monomeric EBV gp350, trimeric EBV gB, monomeric EBV gH/gL, or synergistic combinations thereof (FIG. 6B).
Figure 6B:
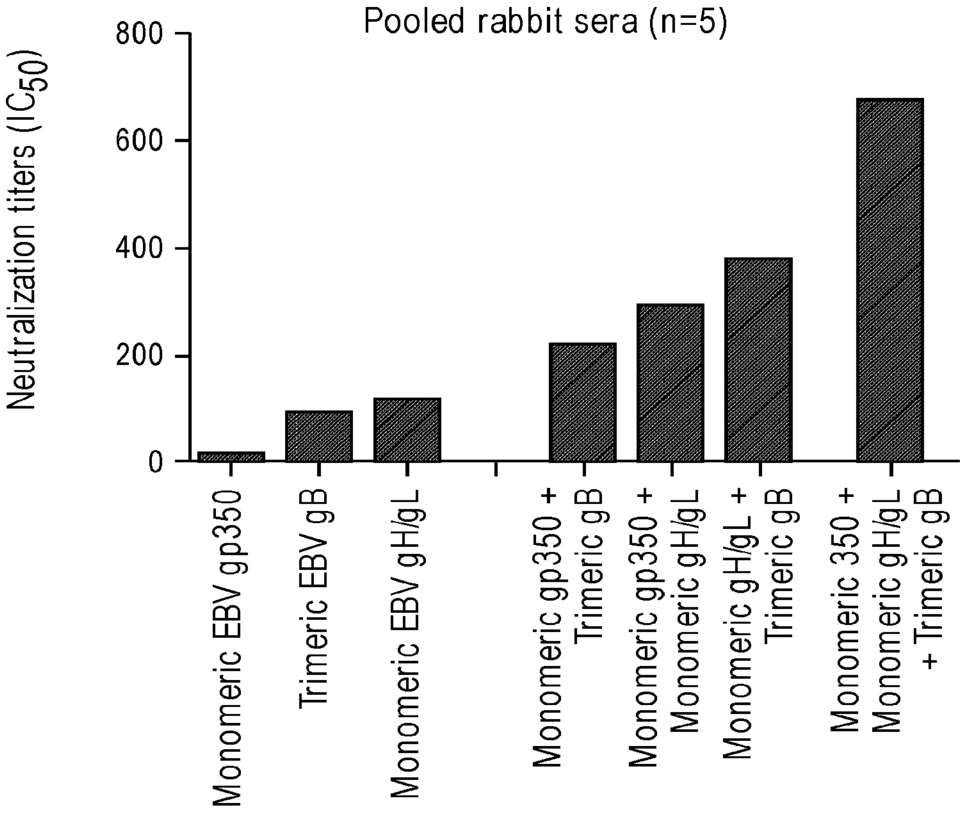

Different combinations of the sera obtained from rabbits immunized with trimeric EBV gB, monomeric EBV gH/gL, or monomeric EBV gp350, were analyzed for in vitro EBV-neutralizing titers using Raji cells. Trimeric gB+monomeric gH/gL sera, trimeric gB+monomeric gp350 sera, monomeric gH/gL+monomeric gp350 sera, and trimeric gB+monomeric gH/gL+monomeric gp350 sera, all showed more than 2-fold increased EBV neutralization activity compared to the sum of the neutralization activity of individual protein immune serum, clearly demonstrating synergistic effects in EBV neutralization activity (FIG. 6B).

Different combinations of the sera from rabbits immunized with EBV trimeric gB, trimeric gH/gL or tetrameric gp350 were also analyzed for in vitro EBV-neutralizing titers using Raji cells. Trimeric gB+trimeric gH/gL sera, trimeric gH/gL+tetrameric gp350 sera, and trimeric gB+trimeric gH/gL+tetrameric gp350 sera showed EBV neutralization activity comparable to the sum of the neutralization activity of individual protein immune serum (FIG. 6B). Trimeric gB+tetrameric gp350 sera showed more than 2-fold increased EBV neutralization activity compared to the sum of the neutralization activity of individual protein immune serum, demonstrating synergism (FIG. 6A).

The synergistic results obtained when certain EBV proteins were combined was not expected. The additive results obtained when other EBV proteins were combined were similarly unexpected given the potential for diminished antibody responses due to vaccine or immune interference.

Example 1.8—Passive Transfer of Immunity Against EBV in NOG Mice

In this study, mice were challenged with live EBV to determine whether anti-sera from the rabbits exposed to EBV polypeptides, above, can protect the mice from EBV infection, i.e. through a passive immunity transfer model. NOD/Shi-scid/IL-2R$\gamma^{null}$ (NOG) mice are an art-recognized humanized mouse model of EBV infection, mirroring key aspects of EBV infection in humans (Yajima et al., *J. Infect. Dis.,* 198:673-82, 2008). NOG mice are immunodeficient, lacking mature T, B, and natural killer cells. The immune system of NOG mice can be reconstituted with a functional human immune system to generate humanized NOG (hu-NOG) mice by transplanting hematopoietic stem cell (HSC) from human cord blood (Yajima et al., J. Infect. Dis., 198:673-82, 2008). Inoculation of the mice with about $1\times10^3$ $TD_{50}$ (50% transforming dose) of EBV causes B cell lymphoproliferation with histopathological findings and latent EBV gene expression similar to that observed in immunocompromised humans, and mortality by 10 weeks post-infection and are thus considered a useful model for EBV-driven PTLD in humans. (Dittmer et al., *Curr. Opin. Virol.,* 14:145-50, 2015).

Hu-NOG mice are still defective in eliciting specific human IgG responses to protein antigens and thus not appropriate for direct vaccination studies (Seung et al., *J. Infect. Dis.,* 208 Suppl 2:S155-9, 2013), necessitating passive immunization studies to determine a protective role for EBV-specific antibodies. In this regard, an earlier study reported that 85% of SCID mice injected i.p. with peripheral blood mononuclear cells (PBMCs) from an EBV-seropositive healthy blood donor developed B cell lymphomas over a 150-day period. However, tumor formation was prevented by weekly treatments with 2 different commercial IVIg preparations (not specifically selected for high EBV neutralizing activity) or by purified IgG from EBV-seropositive, but not seronegative donors. (Abedi et al., *Int. J. Cancer,* 71:624-9, 1997).

In this study, hu-NOG mice were derived by intravenous injection of human CD34(+) HSCs isolated from cord blood (about $1\times10^4$ to $1.2\times10^5$ cells/female mouse at 6-10-week-old). After the human hemato-immune system was reconstituted, four groups (n=4) of hu-NOG mice were injected with 300 μl i.p. of the day 52 pooled sera from rabbits immunized with tetrameric EBV gp350, trimeric EBV gH/gL, trimeric EBV gB, or control (adjuvant (alum+CpG-ODN) alone). Two hours following i.p. injection of rabbit sera, hu-NOG mice were infected intravenously with about $1\times10^3$ $TD_{50}$ of EBV (AKATA Burkitt lymphoma cell line), a dose that induces B cell lymphoproliferation and fatality within or at about 10 weeks. (Yajima et al., J. Infect. Dis., 198:673-682, 2008).

Figure 7A:
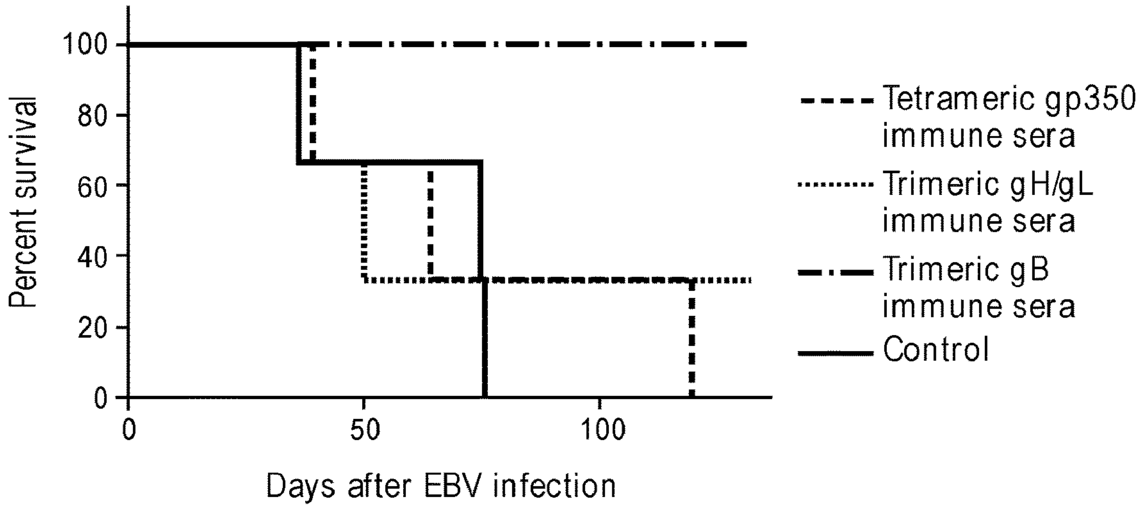
FIGS. 7A-C show that passive transfer of immune rabbit sera prior to EBV-infection of humanized mice decreased EBV DNA load and increased survival rate of challenged mice.
Figure 7B:
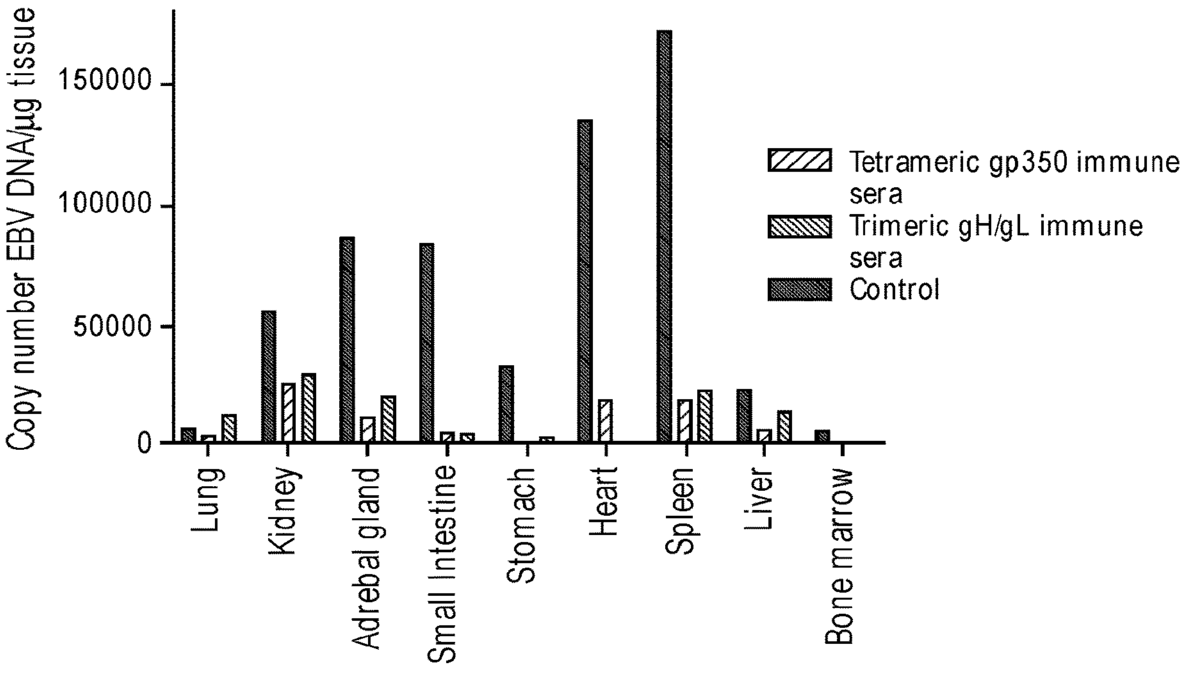
Figure 7C:
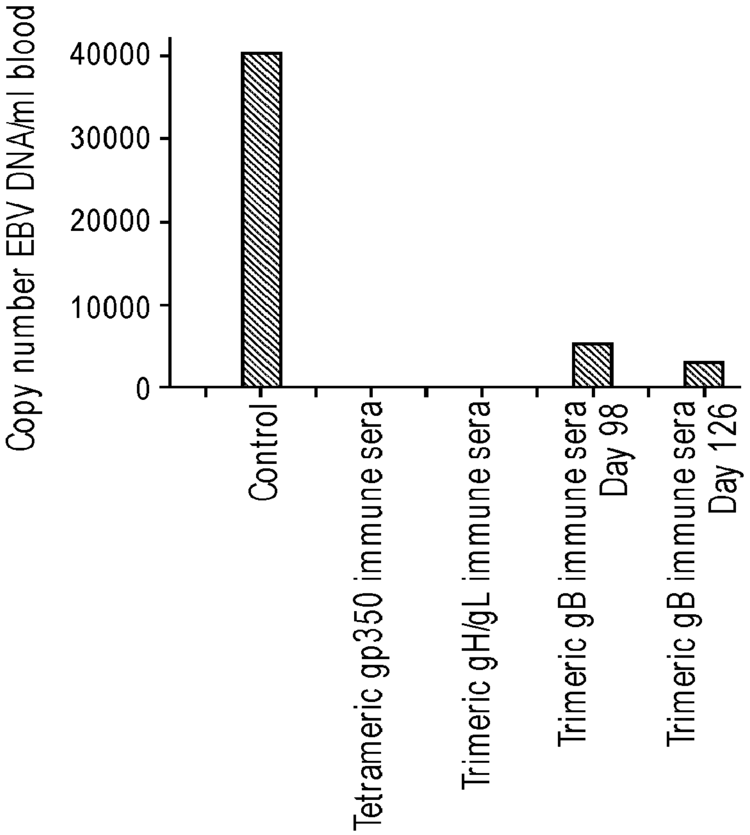

Seventy-five (75) days after EBV infection, the three hu-NOG mice receiving sera from alum+CpG-ODN-injected rabbits all died, whereas all three mice receiving trimeric gB-specific pooled antisera survived after 132 days of EBV infection (FIG. 7A). One hu-NOG mouse receiving tetrameric gp350-specific pooled antisera survived for 119 days, and one hu-NOG mouse receiving trimeric gH/gL-specific pooled antisera survived 132 days (FIG. 7A). Compared to the hu-NOG mice receiving control (alum+CpG-ODN sera), the copy number of EBV from multiple organs of the mice receiving trimeric gH/gL-specific pooled antisera or tetrameric gp350-specific pooled antisera was significantly lower relative to sera from rabbits injected with alum+CpG-ODN alone in multiple organs (FIG. 7B). The effects of gB-specific pooled antisera on EBV organ involvement were not reported as the experiment was ongoing. Hu-NOG mice receiving gB-, gH/gL-, or gp350-specific pooled antisera also showed markedly lower EBV DNA blood levels relative to the adjuvant control, though the hu-NOG mice receiving trimeric gB-specific pooled antisera had higher EBV load in peripheral blood compared to the mice receiving tetrameric gp350-specific pooled antisera or trimeric gH/gL-specific pooled antisera (FIG. 7 C).

2. Human Cytomegalovirus (HCMV)

Example 2.1—Production of Trimeric HCMV gB

The above results with EBV fusion/cell entry proteins show unexpectedly high levels of antibody induction when the EBV polypeptides were combined. Based on these novel findings, we expected to obtain similar results when combining fusion/cell entry proteins from other HHV families, such as HCMV. To this end, similar studies were designed to show that the observations made in the EBV studies can be extended to other HHV family members, like HCMV.

Figure 8:
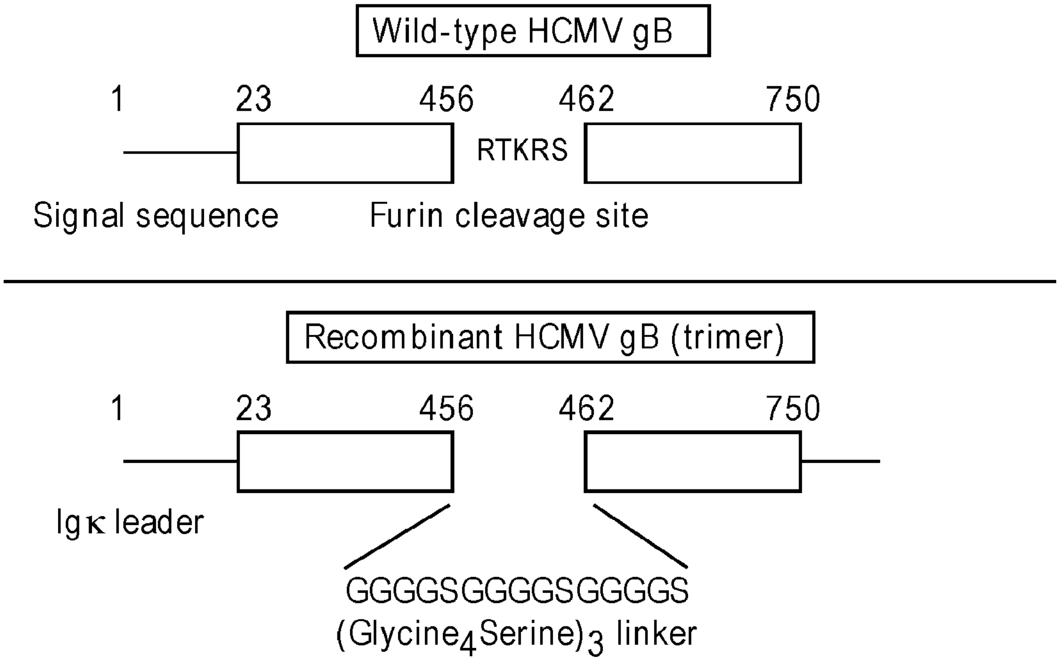
FIG. 8 shows a schematic of a wild type HCMV gB polypeptide and a recombinant construct for expressing a non-limiting embodiment of a trimeric HCMV gB polypeptide.

For HCMV, a coding sequence for HCMV gB was obtained from the NCBI website, reference sequence NC_006273.2, strain Merlin, nucleotides 82066 through 84789. The DNA sequence encoding for amino acids 23-750 of HCMV gB (corresponding to the extracellular domain of gB) was used, and the signal peptide (corresponding to amino acids 1-22) was replaced with an IgG κ leader sequence. To make a trimeric version of the gB polypeptide, the coding sequence for the cleavage site, RTKRS (SEQ ID NO: 53) between amino acids 456 (N) and 462 (T), was replaced with a 15-amino acid $(Gly_4Ser)_3$ (SEQ ID NO: 3) linker sequence (FIG. 8A). A $His_6$ (SEQ ID NO: 49) sequence was added to the 3' end for protein purification. The DNA coding for the gB protein was synthesized, cloned into pOptiVEV (Invitrogen, Carlsbad, CA, USA), and the sequence verified by sequencing. CHO cells (strain DG44; Invitrogen, Carlsbad, CA, USA) were stably transfected with pOptiVEC-gB, and positive cells selected with increasing concentrations of methotrexate up to 4 μM. Supernatants were concentrated for affinity purification using a cobalt column (Thermo Fisher Scientific, Waltham, MA, USA).

Figure 9A:
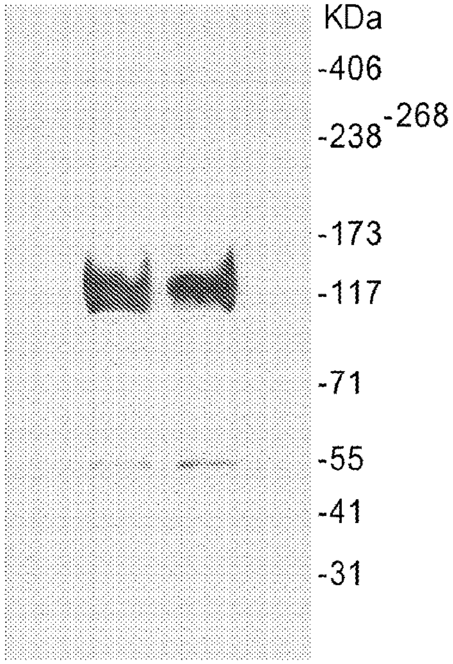
FIGS. 9A-E show images of a Western blot of monomeric HCMV gB (FIG. 9A), trimeric HCMV gB (FIG. 9B), monomeric HCMV gH/gL (FIG. 9C), trimeric HCMV gH/gL (FIG. 9D), and monomeric HCMV UL128/130/131A (FIG. 9E).
Figure 9B:
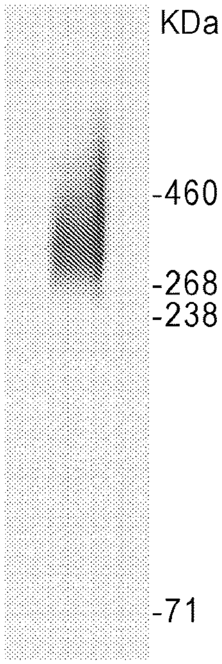

Purified proteins were analyzed by electrophoresis on 3-8% NuPAGE Tris-Acetate Mini-Gels, under reducing condition. Purified HCMV gB was boiled for 10 minutes in lithium dodecyl sulfate sample loading buffer containing 50 mM DTT, blotted with anti-gB monoclonal antibody 2F12 (Virusys Corp., Taneytown, MD, USA) or LS-C64457 (LifeSpan BioSciences, Inc., Seattle, WA, USA), and both showed 120 kDa band corresponding to monomer (FIG. 9A). Purified HCMV gB was also analyzed by PAGE under modified non-reducing condition (mixed protein with Lithium dodecyl sulfate sample buffer without DTT, resolved on 3-8% PAGE in native running buffer), and blotted with anti-gB monoclonal antibody LS-C64457, which showed a band with molecular weight of about 360 kDa, consistent with trimeric gB (FIG. 9B).

Example 2.2—Production of Monomeric and Trimeric HCMV gH/gL Polypeptides

Likewise, the coding sequences for HCMV gH and gL were obtained from the NCBI website, reference sequence NC_006273.2, strain Merlin, gH nucleotides 109224 through 111452, gL nucleotides 165022 through 165858. The construct for trimeric HCMV gH/gL expression was synthesized using MacVector (MacVector, Inc., Apex, NC, USA) and following the design used to express trimeric EBV gH/gL. The gL sequence encoding amino acids 31-278 was used, and the signal peptide corresponding to amino acids 1-30 was replaced with an IgG κ leader sequence. The gH sequence encoding amino acids 24-718 was linked to the 3' end of gL and separated by a 15-amino acid linker $(Gly_4Ser)_3$ (SEQ ID NO: 3) sequence. A foldon trimerization domain coding sequence derived from T4 phage fibritin was linked to the 3' end of gH, followed by a His6 (SEQ ID NO: 49) coding sequence for protein purification. DNA coding for the trimeric gH/gL was synthesized, cloned into pOptiVEV (Invitrogen, Carlsbad, CA, USA), and the sequence was verified by sequencing. The monomeric HCMV gH/gL construct was made by PCR amplification of the trimeric HCMV gH/gL without the foldon trimerization domain coding sequence, cloned into pOptiVEV, and the sequence verified by sequencing.

Figure 9C:
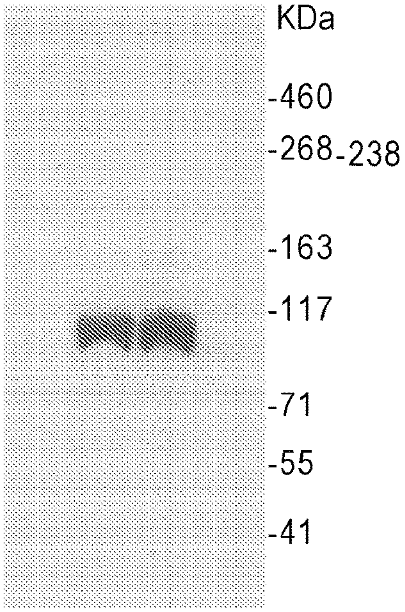
Figure 9D:
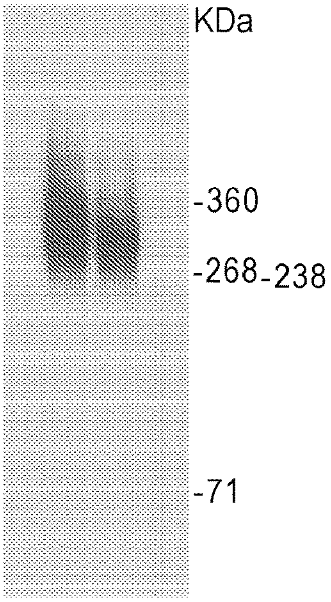

Chinese Hamster Ovary (CHO) cells (strain DG44) (Invitrogen) were stably transfected with the obtained pOptiVEC-gH/gL constructs using Free-style Max reagent (Invitrogen, Carlsbad, CA, USA), and positive transformants were selected with gradually increased concentration of methotrexate up to 4 μM. Supernatants were concentrated and purified using Cobalt affinity purification (Thermo Fisher Scientific, Waltham, MA, USA), and analyzed by Western blot using both an anti-His6 (SEQ ID NO: 49) antibody and anti HCMV gH/gL antibody (Santa Cruz Biotech, Dallas, TX, USA). Under reducing conditions, the Western blot showed monomeric gH/gL as a band of about 110 kDa (FIG. 9C), and under non-reducing conditions, the trimeric gH/gL appeared as a band of about 330 kDa (FIG. 9D).

Example 2.3—Induction of HCMV IgG with Trimeric gB and Monomeric gH/gL

Figure 11:
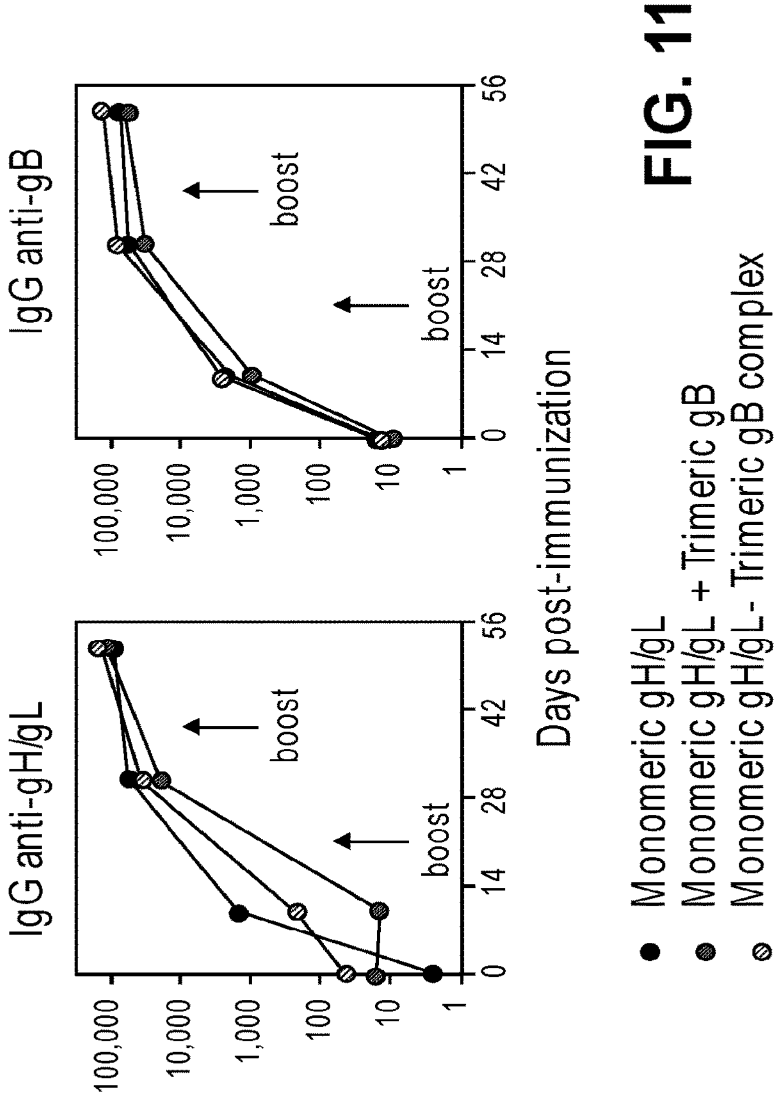
FIG. 11 shows the serum IgG titers of anti-gH/gL antibodies (left panel) and anti-gB antibodies (right panel) following immunization of rabbits with monomeric HCMV gH/gL, trimeric HCMV gB, trimeric HCMV gB+monomeric HCMV gH/gL, or a complex of trimeric HCMV gB+monomeric HCMV gH/gL.

Having generated the desired HCMV polypeptide constructs, comparative studies were conducted to determine whether multimeric polypeptides and/or various polypeptide combinations generated substantially greater immune response than monomeric polypeptides. Thus, seven groups of five male New Zealand white rabbits, 12 to 15 weeks old were immunized subcutaneously with 25 μg of a single HCMV envelope protein or a combination of HCMV envelope proteins (25 μg of each protein in the combination). Twenty-five μg of each protein was adsorbed to aluminum hydroxide (alum; 0.25 μg alum/mg protein) and mixed with 25 μg of CpG-ODN with known activity in rabbits (ODN 2007 having the sequence TCGTCGTTGTCGTTTTGTCGTT (SEQ ID NO: 51)). The HCMV proteins/combinations used were monomeric gH/gL, monomeric UL128/UL130/UL131A, monomeric gB (Sino gB), trimeric gB, monomeric gH/gL+monomeric UL128/UL130/UL131A, trimeric gB+monomeric gH/gL, or trimeric gB+monomeric gH/gL+monomeric UL128/UL130/UL131A. Rabbits were immunized on Day 0, Day 21, and Day 42, and serum samples were taken before initial immunization, and at days 10, 31, 52, and 72 following immunization. Serum titers of antigen-specific IgG against live HCMV were determined using fibroblasts (cell line MRC-5, ATCC, Manassas, VA, USA) and epithelial cells (cell line ARPE-19, ATCC, Manassas, VA, USA). Recombinant trimeric HCMV gB and monomeric HCMV gH/gL proteins were incubated together at room temperature of 30 minutes and were found to induce high titers of protein-specific IgG (FIG. 11).

HCMV neutralization assay. Pooled Day 52 and Day 72 sera from the five rabbits in each cohort immunized with a single HCMV envelope protein or a combination of HCMV envelope proteins were either heat inactivated at 56° C. for 30 minutes to eliminate complement activity or not heat treated. Serum HCMV neutralizing antibody titers were determined using ELISpot assay. Each serum sample was prepared 1:2 serial dilutions with culture medium in in quadruplicates. Each dilution was mixed with an equal volume of culture medium containing HCMV strain AD169WT131, incubated for 4 hours at 37° C. then added to the wells of 96-well plates containing ARPE-19 (epithelial line, ATCC, Manassas, VA, USA) or MRC-5 (fibroblast line, ATCC, Manassas, VA, USA) monolayers and cultured overnight at 37° C., with 5% $CO_2$. Cells were fixed with absolute ethanol, rehydrated and blocked with 5% normal horse serum in PBS, followed by incubation with anti-IE1 monoclonal antibody MAB810 (Merck Millipore, Burlington, MA, USA), goat anti-mouse secondary antibody (Jackson ImmunoResearch Labs, West Grove, PA, USA) each for 1 hour, and VECTASTAIN ABC reagent (Vector Labs, Burlingame, CA, USA) for 30 minutes. Plates were washed three times with 0.05% Tween 20 in PBS between each step, and TrueBlue (Sigma-Aldrich, St. Louis, MO, USA) was added for color development. The plates were scanned and analyzed using a CTL-ImmunoSpot® S6 Micro Analyzer (ImmunoSpot, Cellular Technology Limited, Cleveland, OH, USA). Fifty percent inhibitory concentration ($IC_{50}$) values and standard errors of the means were calculated using GraphPad Prism6 software by plotting the means of triplicate values for each serum dilution against log serum concentration, calculating the best fit four-parameter equation for the data, and interpolating the serum dilution at the mid-point of the curve as the $IC_{50}$ neutralizing titer.

Figure 12A:
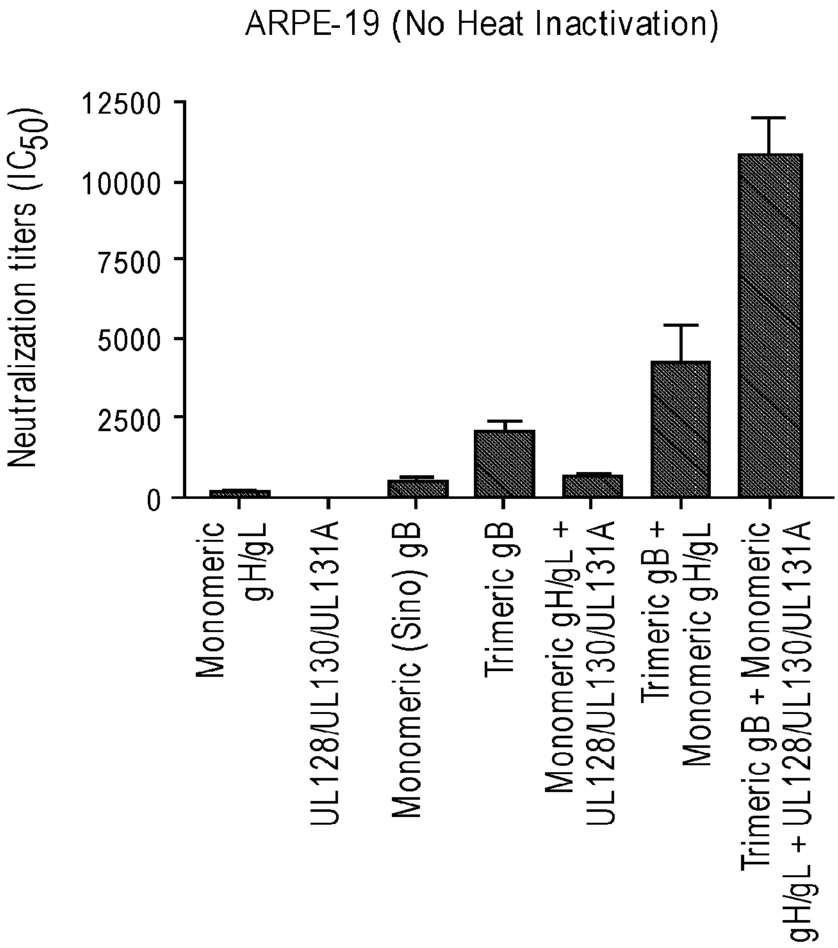
FIG. 12A shows in vitro HCMV neutralization titers ($IC_{50}$) of non-heat inactivated serum from rabbits immunized with monomeric HCMV gH/gL, HCMV UL128/UL130/UL131A, monomeric HCMV gB (Sino gB), trimeric gB, or certain synergistic combinations thereof using the ARPE19 epithelial cell line.

FIG. 12A shows the HCMV neutralization activity analyzed using ARPE-19 cells, where the rabbit immune sera were not heat inactivated. Immunization of rabbits with monomeric UL128/UL130/UL131A elicited little HCMV neutralization activity, yielding an $IC_{50}$ titer of less than 10

(FIG. 12A). Immunization with monomeric gH/gL elicited low level complement-dependent HCMV neutralization activity ($IC_{50}$ of 190.9, FIG. 12A). Immunization of rabbits with the combination of monomeric gH/gL+monomeric UL128/UL130/UL131A elicited 3-fold higher complement-dependent HCMV neutralization activity ($IC_{50}$ of 676.9) than the sum of the HCMV neutralization elicited by monomeric gH/gL or monomeric UL128/UL130/UL131A alone (FIG. 12A). Immunization of rabbits with monomeric gB (Sino gB) elicited moderate complement-dependent HCMV neutralization activity ($IC_{50}$ 528.0), and trimeric gB elicited 4-fold higher complement-dependent HCMV neutralization activity related to monomeric gB ($IC_{50}$ of 2168.8). FIG. 12A. Immunization with a combination of trimeric gB and monomeric gH/gL elicited 2-fold higher complement-dependent HCMV neutralization activity ($IC_{50}$ of 4299.2) than the sum of the HCMV neutralization elicited by trimeric gB and monomeric gH/gL individually, demonstrating a synergistic effect (FIG. 12A). Immunization of rabbits with a combination of trimeric gB, monomeric gH/gL and monomeric UL128/UL130/UL131A elicited 5-fold higher complement-dependent HCMV neutralization activity ($IC_{50}$ of 10910.8) than the sum of the HCMV neutralization elicited by trimeric gB, monomeric gH/gL and monomeric UL128/UL130/UL131A individually, demonstrating a synergistic effect (FIG. 12A). The complement-dependent HCMV neutralization activity elicited by the immunization with combination of trimeric gB, monomeric gH/gL, and monomeric UL128/UL130/UL131A is 20-fold higher than that of the monomeric gB (Sino gB), which demonstrated 50% efficacy in prevention of HCMV infection in phase II clinical trials.

Figure 12B:
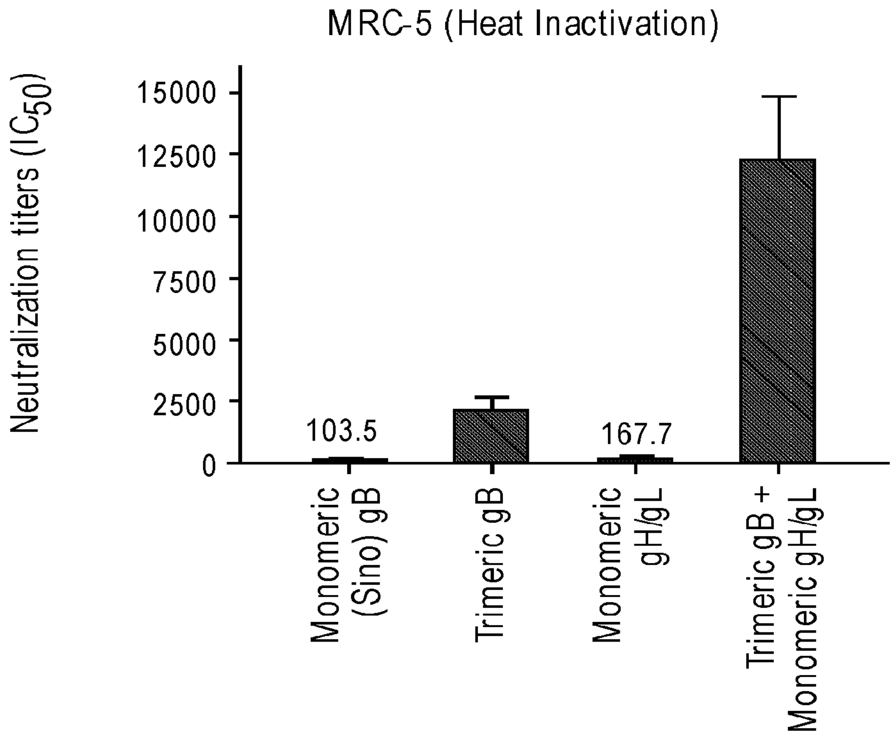
FIG. 12B shows in vitro HCMV neutralization titers ($IC_{50}$) of heat-inactivated serum from rabbits immunized with monomeric HCMV gB (Sino gB), trimeric HCMV gB, monomeric HCMV gH/gL, or a synergistic combination of trimeric HCMV gB and monomeric HCMV gH/gL using the MRC-5 fibroblast cell line.

The HCMV neutralization activity analyzed using fibroblast cell line MRC-5, where the rabbit immune sera were heat inactivated at 56° C. for 30 minutes to eliminate complement activity, is shown in FIG. 12B. Immunization of rabbits with monomeric gB (Sino gB) elicited low levels of complement-independent HCMV neutralization activity ($IC_{50}$ 103.5), and trimeric gB elicited 20-fold higher complement-independent HCMV neutralization activity as compared to monomeric gB ($IC_{50}$ of 2185.2, FIG. 12B). Immunization of rabbits with monomeric gH/gL also elicited low level complement-independent HCMV neutralization activity ($IC_{50}$ of 167.7). In contrast, immunization with a combination of trimeric gB and monomeric gH/gL elicited 5-fold higher complement-independent HCMV neutralization activity ($IC_{50}$ of 12299.4) than the sum of the HCMV neutralization activity elicited by trimeric gB and monomeric gH/gL individually, demonstrating a synergistic effect (FIG. 12B). The complement-independent HCMV neutralization activity elicited by the immunization with a combination of trimeric gB and monomeric gH/gL was more than 100-fold higher than monomeric gB (Sino gB), which demonstrated 50% efficacy in prevention of HCMV infection in phase II clinical trials.

Example 2.4—In Vitro Neutralization Assays Using HCMV gB and gHIgL Anti-Sera Serum HCMV neutralizing antibody titers were determined using an ELISpot assay. Serum samples were combined, and then divided by 1:2 serial dilutions with culture medium in triplicates. Each dilution was mixed with an equal volume of culture medium containing 200 pfu of HCMV strain AD169$^{WT131}$, incubated for 3 h at 37° C., then added to the wells of 96-well plates containing MRC-5 monolayers and cultured overnight at 37° C., with 5% $CO_2$. Cells were fixed with absolute ethanol, rehydrated, and blocked with 1% BSA in PBS, followed by incubation with anti-IE1 monoclonal antibody MAB810 (Millipore), biotin-labeled goat anti-mouse secondary antibody, and ABC reagent (Vector Laboratories) each for 1 h. Plates were washed three times with 0.05% Tween® 20 in PBS between each step, and TrueBlue was added for color development. The plates were scanned and analyzed using a CTL-ImmunoSpot® S6 Micro Analyzer (Cellular Technology Limited, Cleveland, OH). Fifty percent inhibitory concentration ($IC_{50}$) values and standard errors of the means were calculated using GraphPad Prism7 software by plotting the means of triplicate values for each serum dilution against log serum concentration, calculating the best fit four-parameter equation for the data, and interpolating the serum dilution at the mid-point of the curve as the $IC_{50}$ neutralizing titer.

Figure 15:
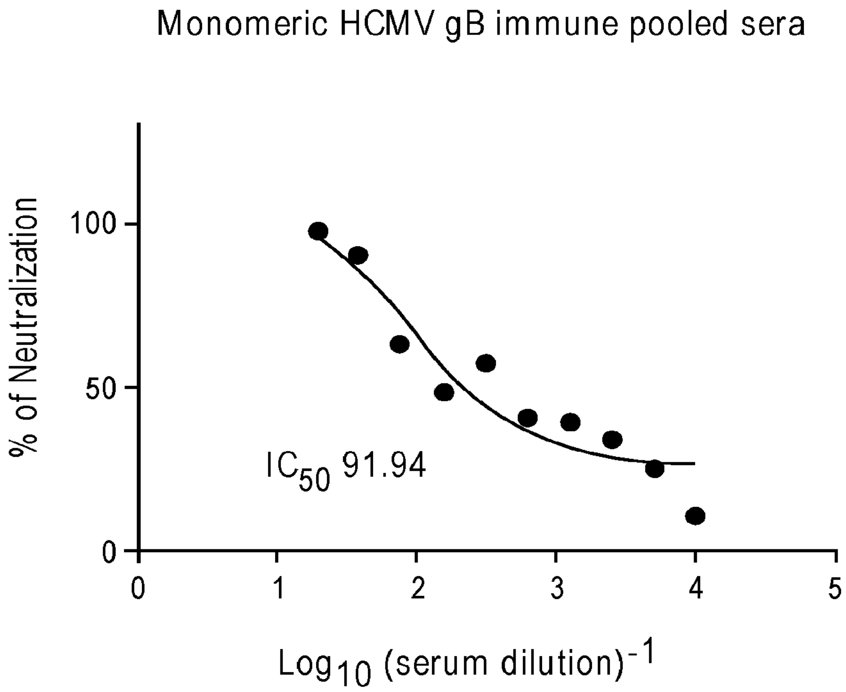
FIG. 15 shows in vitro HCMV neutralization activity of pooled immune sera from rabbits immunized with monomeric HCMV gB.
Figure 16:
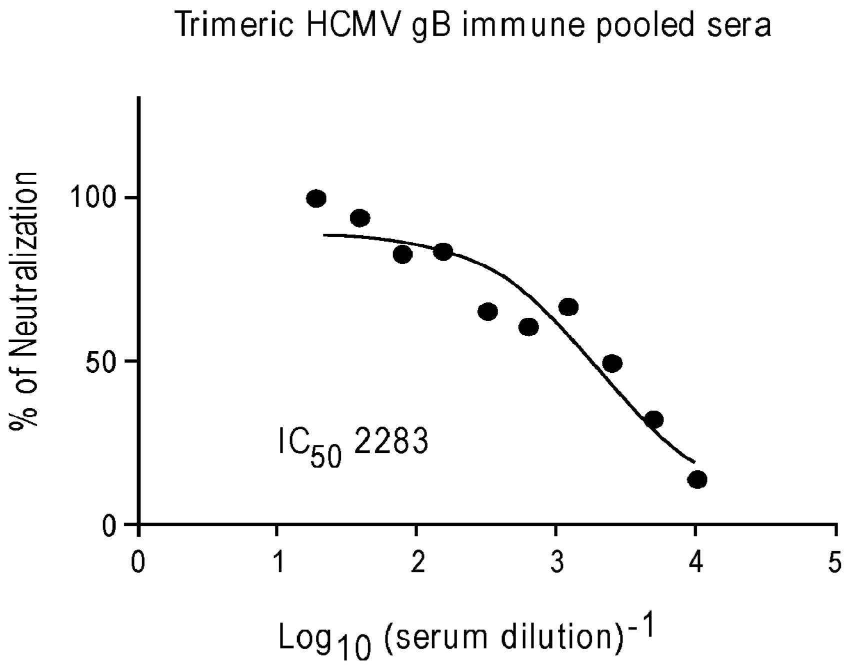
FIG. 16 shows in vitro HCMV neutralization activity of pooled immune sera from rabbits immunized with trimeric HCMV gB.
Figure 17:
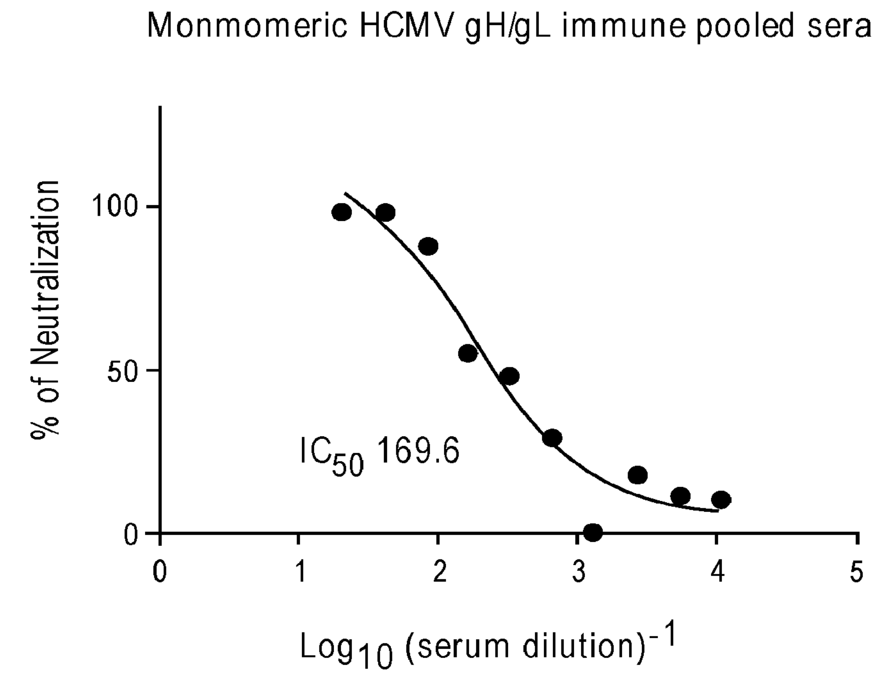
FIG. 17 shows in vitro HCMV neutralization activity of pooled immune sera from rabbits immunized with monomeric HCMV gH/gL.
Figure 18:
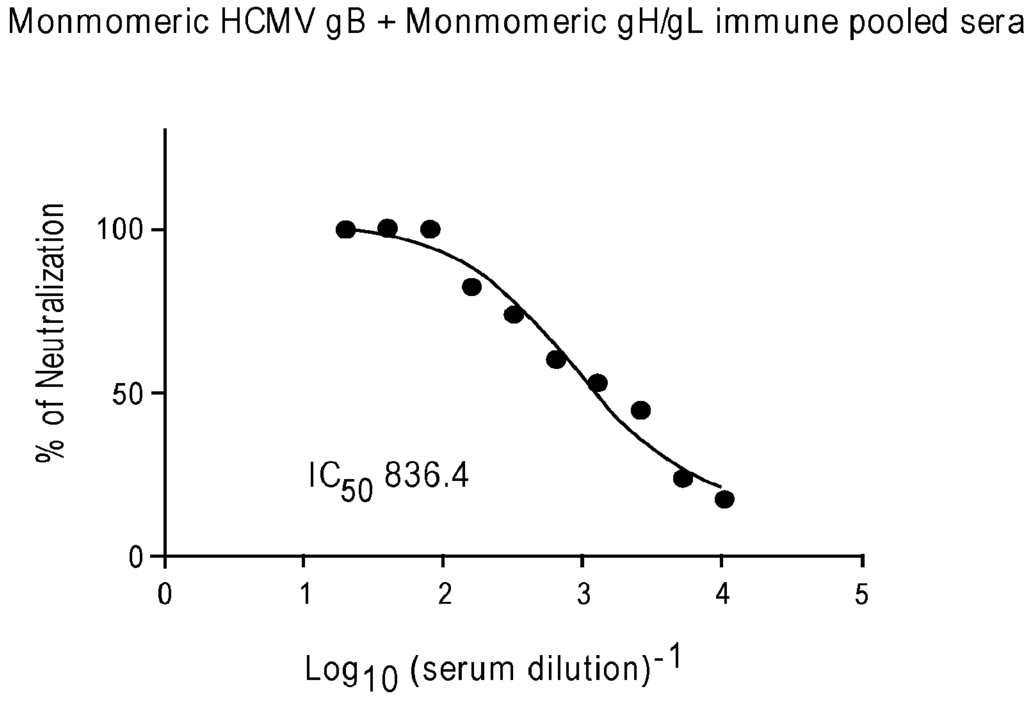
FIG. 18 shows in vitro HCMV neutralization activity of in vitro combined immune sera from rabbits immunized with monomeric HCMV gB and monomeric HMCV gH/gL.
Figure 19:
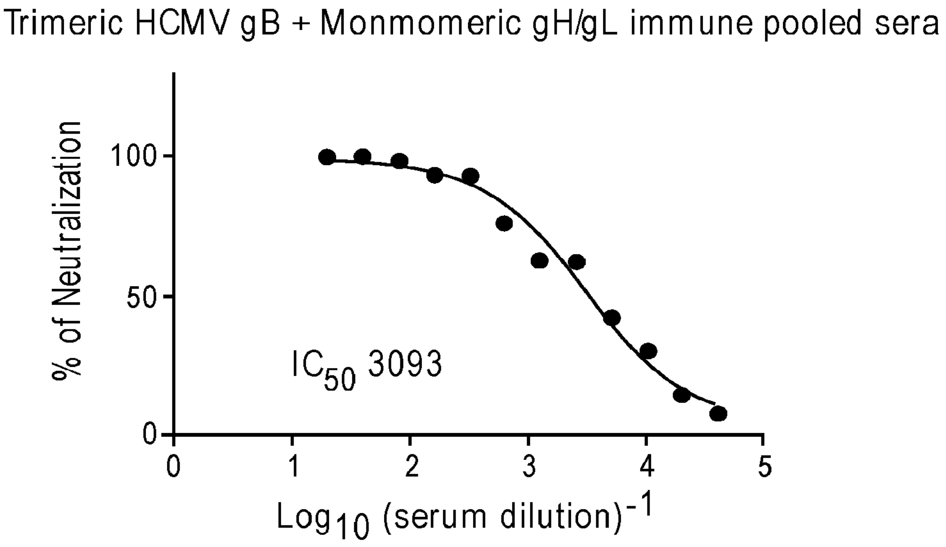
FIG. 19 shows in vitro HCMV neutralization activity of in vitro combined immune sera from rabbits immunized with trimeric HCMV gB and monomeric HMCV gH/gL.
Figure 20:
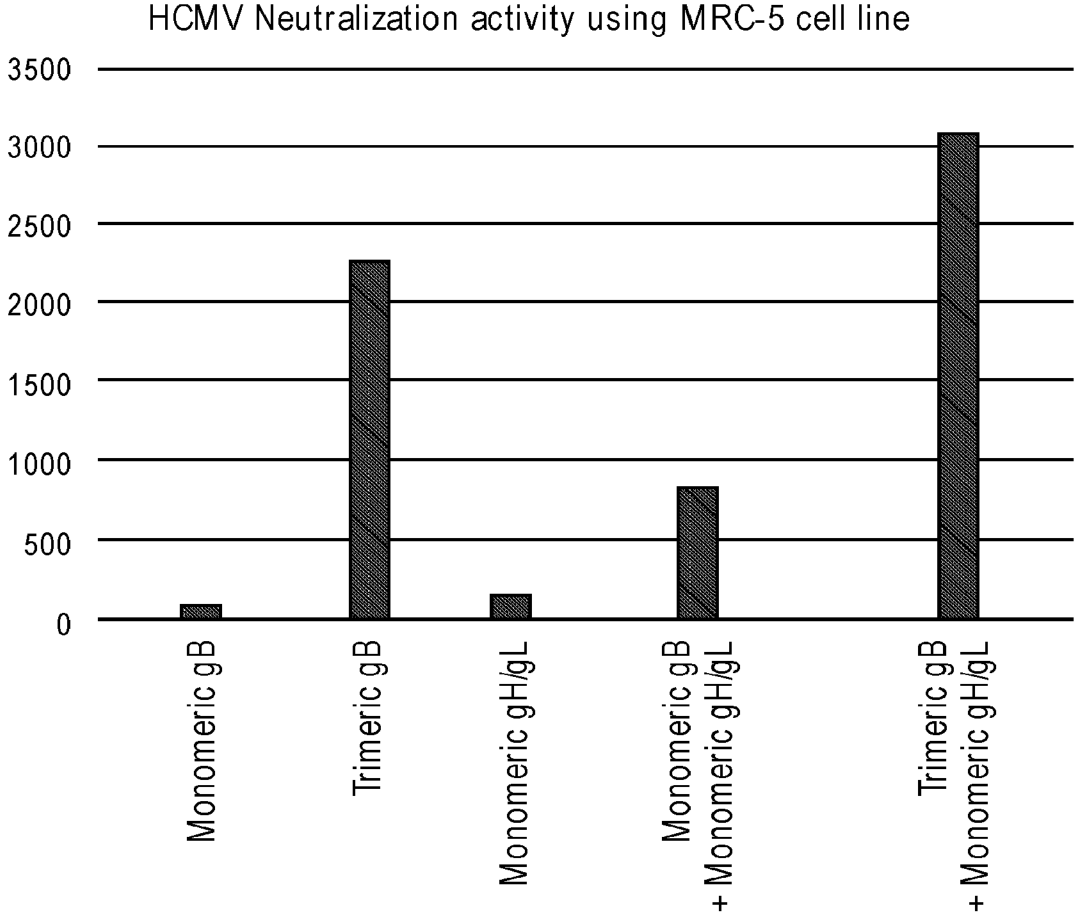
FIG. 20 compares the in vitro HCMV neutralization activity of pooled immune sera from rabbits immunized with individual HCMV proteins (monomeric gB, trimeric gB, and monomeric gH/gL) or in vitro combinations of sera from rabbits immunized with HCMV proteins (monomeric gB and monomeric gH/gL or trimeric gB and monomeric gH/gL) and shows that the combination of HCMV proteins exhibit synergy.

The in vitro HCMV neutralization results obtained using pooled immune sera from rabbits immunized with monomeric HCMV gB, trimeric HCMV gB, monomeric HCMV gH/gL, and in vitro combinations thereof are provided in FIGS. 15-20. Multimerizing the HCMV polypeptides significantly enhanced the neutralizing activity of antibodies generated against the multimerized polypeptides, as compared to a monomeric version of the polypeptide. For example, the $IC_{50}$ of monomeric HCMV gB was 91.94 compared to 2283 for trimeric HCMV gB (FIGS. 15 and 16). Combining HCMV gB immune sera and HCMV gH/gL immune sera unexpectedly induced higher HCMV neutralizing activity than the sum of the neutralizing activity induced by each of the proteins individually, demonstrating synergism. For example, the $IC_{50}$ of the in vitro combination of monomeric HCMV gB immune sera and monomeric gH/gL immune sera was 836.4 (FIG. 18), as compared to an $IC_{50}$ of 91.94 and 169.6, respectively for each of proteins individually (FIGS. 15 and 17). Similarly, the $IC_{50}$ of the in vitro combination of trimeric HCMV gB immune sera and monomeric gH/gL immune sera was 3093 (FIG. 19), as compared to an $IC_{50}$ of 2283 and 169.6 (FIGS. 16 and 17, respectively for each of the proteins individually. These synergistic results are summarized in FIG. 20.

Thus, as with EBV, these comparative tests demonstrate that combining HCMV fusion/cell entry proteins (e.g., gB and gH/gL) unexpectedly enhances HCMV neutralization activity in vivo. Immunization of rabbits with a combination of HCMV trimeric or monomeric gB and monomeric gH/gL elicited significantly higher HCMV neutralization activity than the sum of individual proteins, demonstrating unexpected synergistic effects.

Example 2.5—Production of HCMV Monomeric and Trimeric UL1281130/131 Polypeptides In an effort to further characterize the possibilities of generating heightened antibody titers by administering antigen compositions comprising HHV polypeptides, the HCMV proteins UL128, UL130, and UL131 were recombinantly produced. Briefly, the coding sequences for HCMV UL128 were obtained from the NCBI website, reference sequence GQ121041.1, strain Towne, nucleotides 175653 through 176410. Coding sequences for HCMV UL130 and UL131A were also obtained from the NCBI website, reference sequence NC_006273.2, strain Merlin, UL130 nucleotides 176984 through 177628, and UL131A nucleotides 177649 through 177802 joined to nucleotides 177911 through 178146. UL128 from strain Towne was used because the UL128 from strain Merlin has a mutation and is not functional. The construct for trimeric UL128-UL130-

Figure 10:
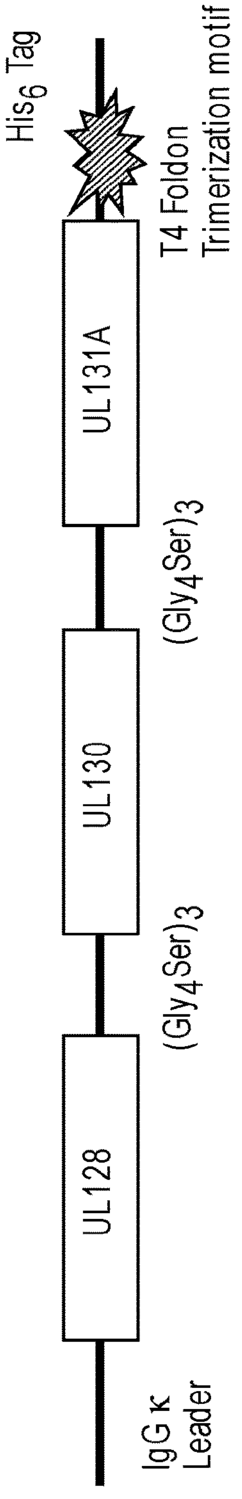
FIG. 10 shows a schematic representing a non-limiting cloning strategy for expressing recombinant trimeric UL128/130/131A.

UL131A expression was designed using MacVector. The UL128 sequence encoding amino acids 28-171, UL130 sequence encoding amino acids 26-214, and UL131A sequence encoding amino acids 19-129, were linked by a 15-amino acid linker $(Gly_4Ser)_3$ (SEQ ID NO: 3) between each coding sequence (FIG. 10). A foldon trimerization domain coding sequence derived from T4 phage fibritin was linked to the 3' end of UL131A, followed by a $His_6$ (SEQ ID NO: 49) coding sequence, and an IgGκ leader sequence was placed 5' to the UL128 sequence for secretion of recombinant protein (FIG. 10). DNA coding for the trimeric UL128-UL130-UL131A was synthesized, cloned into pOptiVEV (Invitrogen, Carlsbad, CA, USA), and the sequence was verified. The monomeric UL128-UL130-UL131A construct was made by PCR amplification of trimeric UL128-UL130-UL131A without the foldon trimerization domain coding sequence, cloned into pOptiVEV, and the sequence was verified.

Figure 9E:
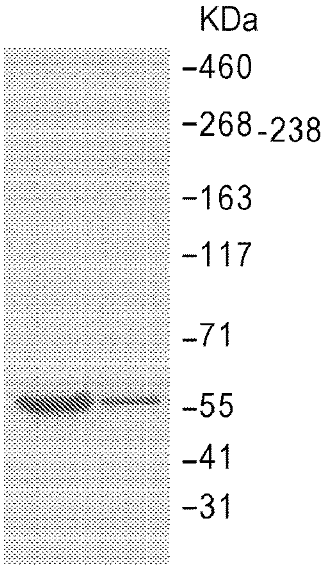

CHO cells (strain DG44, Invitrogen, Thermo Fisher Scientific, Carlsbad, CA, USA) were stably transfected with the resultant pOptiVEC-UL128-UL130-UL131A construct using the Free-style Max reagent (Invitrogen, Carlsbad, CA), and positive transfectants were selected with gradually increased concentrations of methotrexate, up to 4 μM. Supernatants were concentrated and purified using Cobalt affinity purification (Thermo Fisher Scientific, Waltham, MA, USA). Western blot analysis of the supernatants from CHO cells transfected with the monomeric UL128-UL130-UL131A construct using anti-His6 (SEQ ID NO: 49) and anti-UL128 antibodies exhibited a band of about 57 kDa, consistent with monomeric UL128/UL130/UL131A (FIG. 9E).

Example 2.6—Production of HCMV Pentameric gH/gL/UL128/130/31 Complex

The coding sequences for HCMV gH, gL, UL128, UL130 and UL131A were obtained from the NCBI website. A construct for pentameric complex gH/gL/UL128/UL130/UL131A expression was designed using MacVector and is depicted in FIG. 13. The construct includes a gL sequence encoding amino acids 31-278, a gH sequence encoding amino acids 24-718, where the signal peptide of both sequences were replaced with an IgG κ leader sequence. The EV71 Internal Ribosome Entry Site (IRES) sequence was inserted between the sequences of gH and gL, and a His6 (SEQ ID NO: 49) encoding sequence was attached to the 3' end of gH for protein purification. The signal peptides of UL128, UL130, and UL131A were also replaced with an IgG κ leader sequence, and the UL128 sequence encoding amino acids 28-171, UL130 sequence encoding amino acids 26-214, and UL131A sequence encoding amino acids 19-129, were linked together by insertion of the EV71 IRES sequence between each. The UL128, UL130, and UL131A were driven by a second CMV promoter, which was placed 5' end of UL128, and 3' end of gH-$His_6$ (SEQ ID NO: 49) coding sequence. HCMV gL and gH were driven by a first CMV promoter derived from vector pOptiVEC.

DNA coding for the pentameric complex gH/gL/UL128/UL130/UL131A will be synthesized, cloned into pOptiVEV (Invitrogen), and verified. CHO cells (strain DG44; Invitrogen) will be transfected with pOptiVEC-gH/gL/UL128/UL130/UL131A, and positive transformants can be selected with increasing concentrations of methotrexate up to 4 μM, using the procedures already outlined above for similar constructs.

Example 2.7—Production of HCMV gH/gL/gO Complex

As with the other HCMV constructs discussed above, the coding sequences for HCMV gH, gL were also obtained from the NCBI website, and the coding sequences for HCMV gO was also obtained from the NCBI website, reference sequence NC_006273.2, strain Merlin, gO nucleotides 107430 through 108848. The construct for gH/gL/gO complex expression was designed using MacVector and is depicted in FIG. 14, including the gL sequence encoding amino acids 31-278 and the gH sequence encoding amino acids 24-718. The signal peptides of both sequences were replaced with an IgGκ leader sequence. The EV71 Internal Ribosome Entry Site (IRES) sequence was inserted between the gH and gL sequences, and a $His_6$ (SEQ ID NO: 49) encoding sequence was attached to the 3' end of gH for protein purification. The signal peptide of gO was also replaced with an IgG κ leader sequence, and the gO sequence coding amino acids 31-466 was driven by the second CMV promoter, which was placed 5' end of gO, and 3' end of gH-$His_6$ (SEQ ID NO: 49) coding sequence. HCMV gH and gL were driven by the first CMV promoter derived from vector pOptiVEC.

DNA coding for the gH/gL/gO complex will be synthesized and cloned into pOptiVEV as previously described. Stable CHO transformants will be purified and analyzed with size exclusion chromatography and multi-angle light scattering (SEC-MALS).

Example 2.8—Immunization of Mice with HCMV Trimeric gB and Monomeric gB

Six groups of 7- to 10-week old Balb/c mice (n=5) were immunized by the intraperitoneal (i.p.) route with 1 μg, 5 μg, or 25 μg of HCMV trimeric gB or 1 μg, 5 μg, or 25 μg HCMV monomeric gB (Sino gB, Sino Biological Inc., China). Antigen was adsorbed to aluminum hydroxide (alum; 0.25 μg alum/mg protein) and mixed with 25 μg of a 30-mer phophorothioate-modified CpG-ODN (AAAAAAAAAAAAAACGTTAAAAAAAAAAAA (SEQ ID NO: 54)) optimized for mice. Mice immunized with only alum+CpG-ODN served as negative controls. Mice were immunized on day 0, day 21, and day 42, and serum samples were taken before initial immunization, 10 days following each immunization, and at day 63. Individual mouse serum samples were analyzed for titers of gB-specific IgG by ELISA, and in vitro neutralizing activity using fibroblasts (MRC-5) and epithelial cells (ARPE-19).

HCMV neutralization assay. Sera from mice immunized with monomeric or trimeric gB were either heat inactivated at 56° C. for 30 minutes to eliminate complement activity or not heat treated. Serum HCMV neutralizing antibody titers were determined using ELISpot assay. Each serum sample was prepared 1:2 serial dilutions with culture medium in triplicates. Each dilution was mixed with an equal volume of culture medium containing HCMV strain AD169WT131, incubated for 4 hours at 37° C. and then added to the wells of 96-well plates containing MRC-5 (fibroblast line, ATCC, Manassas, VA, USA) monolayers and cultured overnight at 37° C., with 5% $CO_2$. Cells were fixed with absolute ethanol, rehydrated, and blocked with 5% normal horse serum in PBS, followed by incubation with anti-IE1 monoclonal antibody MAB810 (Merck Millipore, Burlington, MA, USA), goat anti-mouse secondary antibody (Jackson ImmunoResearch Labs, West Grove, PA, USA) each for 1 hour, and VECTASTAIN ABC reagent (Vector Labs, Burlingame, CA, USA) for 30 minutes. Plates were washed three times with 0.1% Tween 20 in PBS between each step, and True-Blue (Sigma-Aldrich, St. Louis, MO, USA) was added for color development. The plates were scanned and analyzed using a CTL-ImmunoSpot® S6 Micro Analyzer (ImmunoSpot, Cellular Technology Limited, Cleveland, OH, USA). Fifty percent inhibitory concentration ($IC_{50}$) values and standard errors of the means were calculated using GraphPad Prism6 software by plotting the means of triplicate values for each serum dilution against log serum concentration, calculating the best fit four-parameter equation for the data, and interpolating the serum dilution at the midpoint of the curve as the $IC_{50}$ neutralizing titer.

Figure 21A:
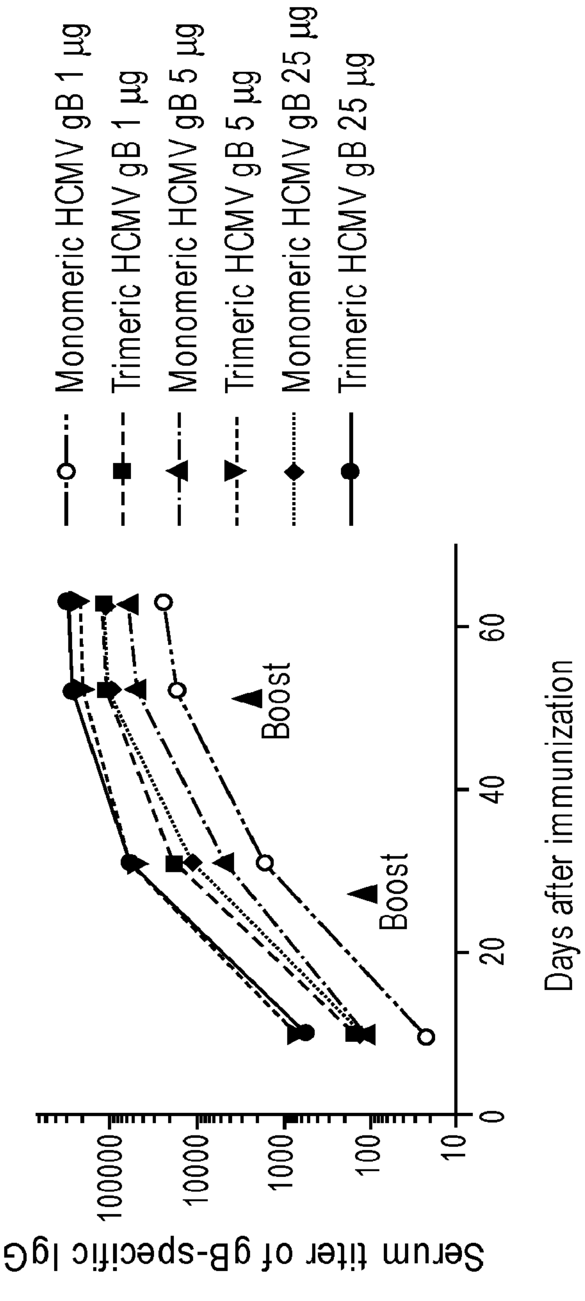
FIG. 21A shows mouse serum titers of gB-specific IgG from mice immunized with different amounts of HCMV trimeric gB or HCMV monomeric gB.

Monomeric and trimeric HCMV gB were directly compared side-by-side for elicitation of total serum titers of antigen-specific IgG. As shown in FIG. 21A, each group of the HCMV proteins induced augmented serum IgG responses following the first booster immunization, and further significant augmentation in serum IgG titers following the second booster immunization. Trimeric HCMV gB induced 5-fold to 11-fold higher serum titers of gB-specific antibody IgG titers relative to monomeric HCMV gB after the first and second immunization, with greater differences observed at the lower doses. The difference of HCMV gB specific IgG titers elicited by trimeric and monomeric HCMV gB decreased after the third immunization, with less differences observed at the higher doses. Five μg of trimeric HCMV gB elicited optimal antigen specific igG response. 25 μg of trimeric HCMV gB elicited slightly higher gB specific IgG titers, but not significantly different compared to that of 5 μg of HCMV trimeric gB.

Figure 21B:
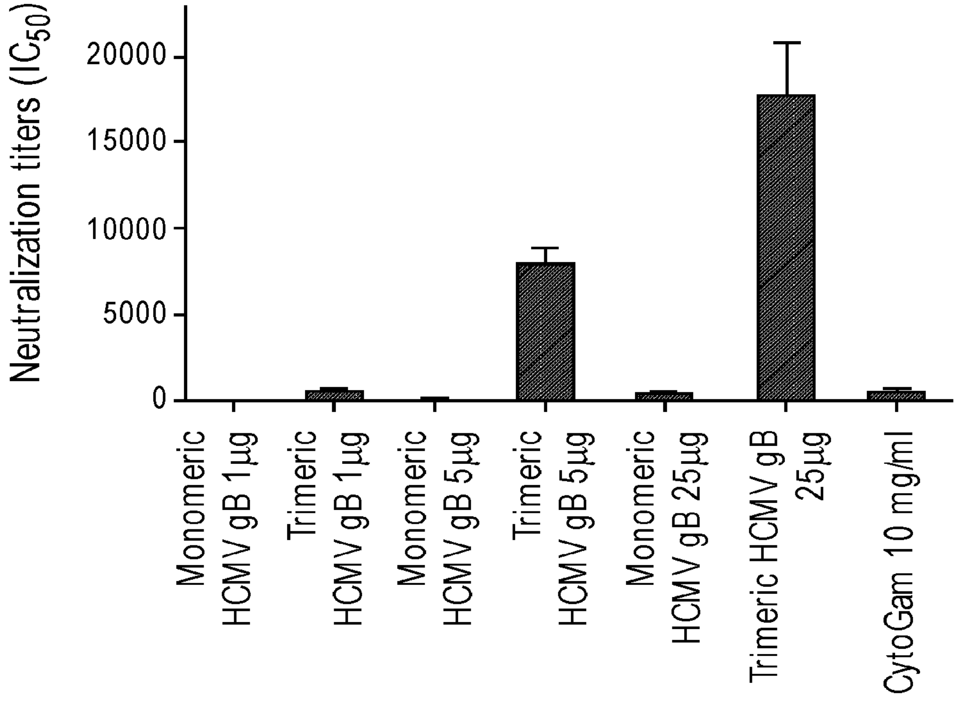
FIGS. 21B-C show neutralization titers ($IC_{50}$) of heat-inactivated serum (FIG. 21B) or non-heat inactivated-serum (FIG. 21C) from mice immunized with monomeric HCMV gB or trimeric HCMV gB at various amounts (1 μg, 5 μg, and 25 μg) or CytoGam® IVIg at 10 mg/mL as a control (CSL Behring, King of Prussia, PA, USA).
Figure 21C:
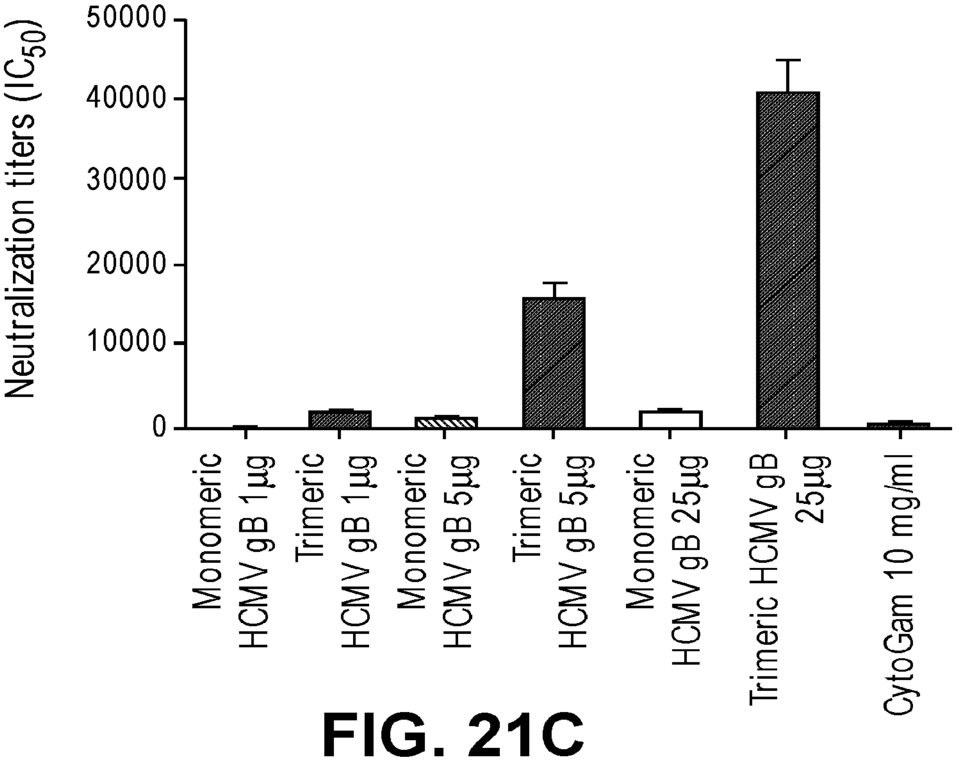

Using the MRC-5 fibroblast cell line, immune sera from mice immunized with trimeric HCMV gB that was heat inactivated at 56° C. for 30 minutes (to eliminate complement activity), demonstrated 50-fold higher HCMV neutralization activity against HCMV strain AD169wt131 compared to that of immune sera from mice immunized with monomeric HCMV gB (FIG. 21B). The non-heat inactivated sera from mice immunized with monomeric HCMV gB (FIG. 21C) demonstrated 6-fold higher HCMV neutralization activity compared to heat inactivated sera (FIG. 21B), whereas the non-heat inactivated sera from mice immunized with trimeric gB demonstrated 2 to 3-fold higher HCMV neutralization activity compared to heat inactivated sera. Without heat inactivation, the HCMV neutralization activity against HCMV strain AD169wt131 elicited by trimeric HCMV gB was 20-fold higher than that of monomeric HCMV gB, suggesting that monomeric HCMV gB induces a more complement-dependent response (FIG. 21C). CytoGam®, a commercial cytomegalovirus CMV-IgIV immunoglobulin containing high titers of HCMV neutralizing antibody derived from the plasma of HCMV seropositive healthy donors (CSL Behring, King of Prussia, PA, USA) showed much lower HCMV neutralization activity against HCMV strain AD169wt131 relative to trimeric gB. Using the MRC-5 cell line, 10 mg/ml CytoGam® demonstrated about one-thirtieth of the complement-independent HCMV neutralization activity of the sera from mice immunized with trimeric HCMV gB. Heat inactivation has no effect on CytoGam®, which made its complement-dependent HCMV neutralization activity even lower compared to non-heat inactivated sera from mice immunized with trimeric HCMV gB or monomeric HCMV gB.

SEQUENCE LISTING

```
Sequence total quantity: 55
SEQ ID NO: 1           moltype = AA  length = 907
FEATURE                Location/Qualifiers
source                 1..907
                       mol_type = protein
                       organism = Epstein-Barr virus
SEQUENCE: 1
MEAALLVCQY TIQSLIHLTG EDPGFFNVEI PEFPFYPTCN VCTADVNVTI NFDVGGKKHQ  60
LDLDFGQLTP HTKAVYQPRG AFGGSENATN LFLLELLGAG ELALTMRSKK LPINVTTGEE  120
QQVSLESVDV YFQDVFGTMW CHHAEMQNPV YLIPETVPYI KWDNCNSTNI TAVVRAQGLD  180
VTLPLSLPTS AQDSNFSVKT EMLGNEIDIE CIMEDGEISQ VLPGDNKFNI TCSGYESHVP  240
SGGILTSTSP VATPIPGTGY AYSLRLTPRP VSRFLGNNSI LYVFYSGNGP KASGGDYCIQ  300
SNIVFSDEIP ASQDMPTNTT DITYVGDNAT YSVPMVTSED ANSPNVTVTA FWAWPNNTET  360
DFKCKWTLTS GTPSGCENIS GAFASNRTFD ITVSGLGTAP KTLIITRTAT NATTTTHKVI  420
FSKAPESTTT SPTLNTTGFA DPNTTTGLPS STHVPTNLTA PASTGPTVST ADVTSPTPAG  480
TTSGASPVTP SPSPWDNGTE SKAPDMTSST SPVTTPTPNA TSPTPAVTTP TPNATSPTPA  540
VTTPTPNATS PTLGKTSPTS AVTTPTPNAT SPTLGKTSPT SAVTTPTPNA TSPTLGKTSP  600
TSAVTTPTPN ATGPTVGETS PQANATNHTL GGTSPTPVVT SQPKNATSAV TTGQHNITSS  660
STSSMSLRPS SNPETLSPST SDNSTSHMPL LTSAHPTGGE NITQVTPASI STHHVSTSSP  720
EPRPGTTSQA SGPGNSSTST KPGEVNVTKG TPPQNATSPQ APSGQKTAVP TVTSTGGKAN  780
STTGGKHTTG HGARTSTEPT TDYGGDSTTP RPRYNATTYL PPSTSSKLRP RWTFTSPPVT  840
TAQATVPVPP TSQPRFSNLS MLVLQWASLA VLTLLLLLVM ADCAFRRNLS TSHTYTTPPY  900
DDAETYV                                                            907

SEQ ID NO: 2           moltype = AA  length = 658
FEATURE                Location/Qualifiers
source                 1..658
                       mol_type = protein
                       organism = Epstein-Barr virus
SEQUENCE: 2
MEAALLVCQY TIQSLIHLTG EDPGFFNVEI PEFPFYPTCN VCTADVNVTI NFDVGGKKHQ  60
LDLDFGQLTP HTKAVYQPRG AFGGSENATN LFLLELLGAG ELALTMRSKK LPINVTTGEE  120
QQVSLESVDV YFQDVFGTMW CHHAEMQNPV YLIPETVPYI KWDNCNSTNI TAVVRAQGLD  180
VTLPLSLPTS AQDSNFSVKT EMLGNEIDIE CIMEDGEISQ VLPGDNKFNI TCSGYESHVP  240
SGGILTSTSP VATPIPGTGY AYSLRLTPRP VSRFLGNNSI LYVFYSGNGP KASGGDYCIQ  300
SNIVFSDEIP ASQDMPTNTT DITYVGDNAT YSVPMVTSED ANSPNVTVTA FWAWPNNTET  360
DFKCKWTLTS GTPSGCENIS GAFASNRTFD ITVSGLGTAP KTLIITRTAT NATTTTHKVI  420
```

-continued

```
FSKAPESTTT SPTLNTTGFA DPNTTTGLPS STHVPTNLTA PASTGPTVST ADVTSPTPAG  480
TTSGASPVTP SPSPWDNGTE STPPQNATSP QAPSGQKTAV PTVTSTGGKA NSTTGGKHTT  540
GHGARTSTEP TTDYGGDSTT PRPRYNATTY LPPSTSSKLR PRWTFTSPPV TTAQATVPVP  600
PTSQPRFSNL SMLVLQWASL AVLTLLLLLV MADCAFRRNL STSHTYTTPP YDDAETYV    658

SEQ ID NO: 3            moltype = AA  length = 15
FEATURE                 Location/Qualifiers
source                  1..15
                        mol_type = protein
                        organism = synthetic construct
SEQUENCE: 3
GGGGSGGGGS GGGGS                                                   15

SEQ ID NO: 4            moltype = AA  length = 706
FEATURE                 Location/Qualifiers
source                  1..706
                        mol_type = protein
                        organism = Epstein-Barr virus
SEQUENCE: 4
MQLLCVFCLV LLWEVGAASL SEVKLHLDIE GHASHYTIPW TELMAKVPGL SPEALWREAN  60
VTEDLASMLN RYKLIYKTSG TLGIALAEPV DIPAVSEGSM QVDASKVHPG VISGLNSPAC  120
MLSAPLEKQL FYYIGTMLPN TRPHSYVFYQ LRCHLSYVAL SINGDKFQYT GAMTSKFLMG  180
TYKRVTEKGD EHVLSLIFGK TKDLPDLRGP FSYPSLTSAQ SGDYSLVIVT TFVHYANFHN  240
YFVPNLKDMF SRAVTMTAAS YARYVLQKLV LLEMKGGCRE PELDTETLTT MFEVSVAFFK  300
VGHAVGETGN GCVDLRWLAK SFFELTVLKD IIGICYGATV KGMQSYGLER LAAVLMATVK  360
MEELGHLTTE KQEYALRLAT VGYPKAGVYS GLIGGATSVL LSAYNRHPLF QPLHTVMRET  420
LFIGSHVVLR ELRLNVTTQG PNLALYQLLS TALCSALEIG EVLRGLALGT ESGLFSPCYL  480
SLRFDLTRDK LLSMAPQEAM LDQAAVSNAV DGFLGRLSLE REDRDAWHLP AYKCVDRLDK  540
VLMIIPLINV TFIISSDREV RGSALYEAST TYLSSSLFLS PVIMNKCSQG AVAGEPRQIP  600
KIQNFTRTQK SCIFCGFALL SYDEKEGLET TTYITSQEVQ NSILSSNYFD FDNLHVHYLL  660
LTTNGTVMEI AGLYEERAHV VLAIILYFIA FALGIFLVHK IVMFFL                 706

SEQ ID NO: 5            moltype = AA  length = 137
FEATURE                 Location/Qualifiers
source                  1..137
                        mol_type = protein
                        organism = Epstein-Barr virus
SEQUENCE: 5
MRTVGVFLAT CLVTIFVLPT WGNWAYPCCH VTQLRAQHLL ALENISDIYL VSNQTCDGFS  60
LASLNSPKNG SNQLVISRCA NGLNVVSFFI SILKRSSSAL TGHLRELLTT LETLYGSFSV  120
EDLFGANLNR YAWHRGG                                                 137

SEQ ID NO: 6            moltype = AA  length = 857
FEATURE                 Location/Qualifiers
source                  1..857
                        mol_type = protein
                        organism = Epstein-Barr virus
SEQUENCE: 6
MTRRRVLSVV VLLAALACRL GAQTPEQPAP PATTVQPTAT RQQTSFPFRV CELSSHGDLF  60
RFSSDIQCPS FGTRENHTEG LLMVFKDNII PYSFKVRSYT KIVTNILIYN GWYADSVTNR  120
HEEKFSVDSY ETDQMDTIYQ CYNAVKMTKD GLTRVYVDRD GVNITVNLKP TGGLANGVRR  180
YASQTELYDA PGWLIWTYRT RTTVNCLITD MMAKSNSPFD FFVTTTGQTV EMSPFYDGKN  240
KETFHERADS FHVRTNYKIV DYDNRGTNPQ GERRAFLDKG TYTLSWKLEN RTAYCPLQHW  300
QTFDSTIATE TGKSIHFVTD EGTSSFVTNT TVGIELPDAF KCIEEQVNKT MHEKYEAVQD  360
RYTKGQEAIT YFITSGGLLL AWLPLTPRSL ATVKNLTELT TPTSSPPSSP SPPAPPAARG  420
STSAAVLRRR RRDAGNATTP VPPAAPGKSL GTLNNPATVQ IQFAYDSLRR QINRMLGDLA  480
RAWCLEQKRQ NMVLRELTKI NPTTVMSSIY GKAVAAKRLG DVISVSQCVP VNQATVTLRK  540
SMRVPGSETM CYSRPLVSFS FINDTKTYEG QLGTDNEIFL TKKMTEVCQA TSQYYFQSGN  600
EIHVYNDYHH FKTIELDGIA TLQTFISLNT SLIENIDFAS LELYSRDEQR ASNVFDLEGI  660
FREYNFQAQN IAGLRKDLDN AVSNGRNQFV DGLGELMDSL GSVGQSITNL VSTVGGLFSS  720
LVSGFISFFK NPFGGMLILV LVAGVVILVI SLTRRTRQMS QQPVQMLYPG IDELAQQHAS  780
GEGPGINPIS KTELQAIMLA LHEQNQEQKR AAQRAAGPSV ASRALQAARD RFPGLRRRRY  840
HDPETAAALL GEAETEF                                                 857

SEQ ID NO: 7            moltype = AA  length = 223
FEATURE                 Location/Qualifiers
source                  1..223
                        mol_type = protein
                        organism = Epstein-Barr virus
SEQUENCE: 7
MVSFKQVRVP LFTAIALVIV LLLAYFLPPR VRGGGRVSAA AITWVPKPNV EVWPVDPPPP  60
VNFNKTAEQE YGDKEIKLPH WTPTLHTFQV PKNYTKANCT YCNTREYTFS YKERCFYFTK  120
KKHTWNGCFQ ACAELYPCTY FYGPTPDILP VVTRNLNAIE SLWVGVYRVG EGNWTSLDGG  180
TFKVYQIFGS HCTYVSKFST VPVSHHECSF LKPCLCVSQR SNS                    223

SEQ ID NO: 8            moltype = AA  length = 357
FEATURE                 Location/Qualifiers
source                  1..357
                        mol_type = protein
```

```
                        organism = Epstein-Barr virus
SEQUENCE: 8
MFSCKQHLSL GACVFCLGLL ASTPFIWCFV FANLLSLEIF SPWQTHVYRL GFPTACLMAV  60
LWTLVPAKHA VRAVTPAIML NIASALIFFS LRVYSTSTWV SAPCLFLANL PLLCLWPRLA  120
IEIVYICPAI HQRFFELGLL LACTIFALSV VSRALEVSAV FMSPFFIFLA LGSGSLAGAR  180
RNQIYTSGLE RRRSIFCARG DHSVASLKET LHKCPWDLLA ISALTVLVVC VMIVLHVHAE  240
VFFGLSRYLP LFLCGAMASG GLYLGHSSII ACVMATLCTL TSVVVYFLHE TLGPLGKTVL  300
FISIFVYYFS GVAALSAAMR YKLKKFVNGP LVHLRVVYMC CFVFTFCEYL LVTFIKS     357

SEQ ID NO: 9            moltype = AA  length = 420
FEATURE                 Location/Qualifiers
source                  1..420
                        mol_type = protein
                        organism = Epstein-Barr virus
SEQUENCE: 9
MVDEQVAVEH GTVSHTISRE EDGVVHERRV LASGERVEVF YKAPAPRPRE GRASTFHDFT  60
VPAAAAVPGP EPEPEPHPPM PIHANGGGET KTNTQDQNQN QTTRTRTNAK AEERTAEMDD  120
TMASSGGQRG APISADLLSL SSLTGRMAAM APSWMKSEVC GERMRFKEDV YDGEAETLAE  180
PPRCFMLSFV FIYYCCYLAF LALLAFGFNP LFLPSFMPVG AKVLRGKGRD FGVPLSYGCP  240
TNPFCKVYTL IPAVVINNVT YYPNNTDSHG GHGGFEAAAL HVAALFESGC PNLQAVTNRN  300
RTFNVTRASG RVERRLVQDM QRVLASAVVV MHHHCHYETY YVFDGVGPEF GTIPTPCFKD  360
VLAFRPSLVT NCTAPLKTSV KGPNWSGAAG GMKRKQCRVD RLTDRSFPAY LEEVMYVMVQ  420

SEQ ID NO: 10           moltype = AA  length = 228
FEATURE                 Location/Qualifiers
source                  1..228
                        mol_type = protein
                        organism = Kaposi's sarcoma-associated herpesvirus
SEQUENCE: 10
MSSTQIRTEI PVALLILCLC LVACHANCPT YRSHLGFWQE GWSGQVYQDW LGRMNCSYEN  60
MTALEAVSLN GTRLAAGSPS SEYPNVSVSV EDTSASGSGE DAIDESGSGE EERPVTSHVT  120
FMTQSVQATT ELTDALISAF SGSYSSGEPS RTTRIRVSPV AENGRNSGAS NRVPFSATTT  180
TTRGRDAHYN AEIRTHLYIL WAVGLLLGLV LILYLCVPRC RRKKPYIV                228

SEQ ID NO: 11           moltype = AA  length = 167
FEATURE                 Location/Qualifiers
source                  1..167
                        mol_type = protein
                        organism = Kaposi's sarcoma-associated herpesvirus
SEQUENCE: 11
MSSTQIRTEI PVALLILCLC LVACHANCPT YRSHLGFWQE GWSGQVYQDW LGRMNCSYEN  60
MTALEAVSLN GTRLAAGSPS RSYSSGEPSR TTRIRVSPVA ENGRNSGASN RVPFSATTTT  120
TRGRDAHYNA EIRTHLYILW AVGLLLGLVL ILYLCVPRCR RKKPYIV                167

SEQ ID NO: 12           moltype = AA  length = 730
FEATURE                 Location/Qualifiers
source                  1..730
                        mol_type = protein
                        organism = Kaposi's sarcoma-associated herpesvirus
SEQUENCE: 12
MQGLAFLAAL ACWRCISLTC GATGALPTTA TTITRSATQL INGRTNLSIE LEFNGTSFFL  60
NWQNLLNVIT EPALTELWTS AEVAEDLRVT LKKRQSLFFP NKTVVISGDG HRYTCEVPTS  120
SQTYNITKGF NYSALPGHLG GFGINARLVL GDIFASKWSL FARDTPEYRV FYPMNVMAVK  180
FSISIGNNES GVALYGVVSE DFVVVTLHNR SKEANETASH LLFGLPDSLP SLKGHATYDE  240
LTFARNAKYA LVAILPKDSY QTLLTENYTR IFLNMTESTP LEFTRTIQTR IVSIEARRAC  300
AAQEAAPDIF LVLFQMLVAH FLVARGIAEH RFVEVDCVCR QYAELYFLRR ISRLCMPTFT  360
TVGYNHTTLG AVAATQIARV SATKLASLPR SSQETVLAMV QLGARDGAVP SSILEGIAMV  420
VEHMYTAYTY VYTLGDTERK LMLDIHTVLT DSCPPKDSGV SEKLLRTYLM FTSMCTNIEL  480
GEMIARFSKP DSLNIYRAFS PCFLGLRYDL HPAKLRAEAP QSSALTRTAV ARGTSGFAEL  540
LHALHLDSLN LIPAINCSKI TADKIIATVP LPHVTYIISS EALSNAVVYE VSEIFLKSAM  600
FISAIKPDCS GFNFSQIDRH IPIVYNISTP RRGCPLCDSV IMSYDESDGL QSLMYVTNER  660
VQTNLFLDKS PFFDNNNLHI HYLWLRDNGT VVEIRGMYRR RAASALFLIL SFIGFSGVIY  720
FLYRLFSILY                                                          730

SEQ ID NO: 13           moltype = AA  length = 167
FEATURE                 Location/Qualifiers
source                  1..167
                        mol_type = protein
                        organism = Kaposi's sarcoma-associated herpesvirus
SEQUENCE: 13
MGIFALFAVL WTTLLVTSHA YVALPCCAIQ ASAASTLPLF FAVHSIHFAD PNHCNGVCIA  60
KLRSKTGDIT VETCVNGFNL RSFLVAVVRR LGSWASQENL RLLWYLQRSL TAYTVGFNAT  120
TADSSIHNVN IIIISVGKAM NRTGSVSGSQ TRAKSSSRRA HAGQKGK                 167

SEQ ID NO: 14           moltype = AA  length = 110
FEATURE                 Location/Qualifiers
source                  1..110
                        mol_type = protein
                        organism = Kaposi's sarcoma-associated herpesvirus
```

```
SEQUENCE: 14
MTASTVALAL FVASILGHCW VTANSTGVAS STERSSPSTA GLSARPSPGP TSVTTPGFYD  60
VACSADSFSP SLSSFSSVWA LINALLVVVA TFFYLVYLCF FKFVDEVVHA             110

SEQ ID NO: 15          moltype = AA  length = 400
FEATURE                Location/Qualifiers
source                 1..400
                       mol_type = protein
                       organism = Kaposi's sarcoma-associated herpesvirus
SEQUENCE: 15
MRASKSDRFL MSSWVKLLFV AVIMYICSAV VPMAATYEGL GFPCYFNNLV NYSALNLTVR  60
NSAKHLTPTL FLEKPEMLVY IFWTFIVDGI AIVYYCLAAV AVYRAKHVHA TTMMSMQSWI  120
ALLGSHSVLY VAILRMWSMQ LFIHVLSYKH VLMAAFVYCI HFCISFAHIQ SLITCNSAQW  180
EIPLLEQHVP DNTMMESLLT RWKPVCVNLY LSTTALEMLL FSLSTMMAVG NSFYVLVSDA  240
IFGAVNMFLA LTVVWYINTE FFLVKFMRRQ VGFYVGVFVG YLILLLPVIR YENAFVQANL  300
HYIVAINISC IPILCILAIV IRVIRSDWGL CTPSAAYMPL ATSAPTVDRT PTVHQKPPPL  360
PAKTRARAKV KDISTPAPRT QYQSDHESDS EIDETQMIFI                        400

SEQ ID NO: 16          moltype = AA  length = 467
FEATURE                Location/Qualifiers
source                 1..467
                       mol_type = protein
                       organism = Kaposi's sarcoma-associated herpesvirus
SEQUENCE: 16
MFVPWQLGTI TRHRDELQKL LAASLLPEHP EESLGNPIMT QIHQSLQPSS PCRVCQLLFS  60
LVRDSSTPMG FFEDYACLCF FCLYAPHCWT STMAAAADLC EIMHLHFPEE EATYGLFGPG  120
RLMGIDLQLH FFVQKCFKTT AAEKILGISN LQFLKSEFIR GMLTGTITCN FCFKTSWPRT  180
DKEEATGPTP CCQITDTTTA PASGIPELAR ATFCGASRPT KPSLLPALID IWSTSSELLD  240
EPRPRLIASD MSELKSVVAS HDPFFSPPLQ ADTSQGPCLM HPTLGLRYKN GTASVCLLCE  300
CLAAHPEAPK ALQTLQCEVM GHIENNVKLV DRIAFVLDNP FAMPYVSDPL LRELIRGCTP  360
QEIHKHLFCD PLCALNAKVV SEDVLFRLPR EQEYKKLRAS AAAGQLLDAN TLFDCEVVQT  420
LVFLFKGLQN ARVGKTTSLD IIRELTAQLK RHRLDLAHPS QTSHLYA                467

SEQ ID NO: 17          moltype = AA  length = 743
FEATURE                Location/Qualifiers
source                 1..743
                       mol_type = protein
                       note = Human cytomegalovirus
                       organism = unidentified
SEQUENCE: 17
MRPGLPPYLT VFTVYLLSHL PSQRYGADAA SEALDPHAFH LLLNTYGRPI RFLRENTTQC  60
TYNSSLRNST VVRENAISFN FFQSYNQYYV FHMPRCLFAG PLAEQFLNQV DLTETLERYQ  120
QRLNTYALVS KDLASYRSFS QQLKAQDSLG QQPTTVPPPI DLSIPHVWMP PQTTPHDWKG  180
SHTTSGLHRP HFNQTCILFD GHDLLFSTVT PCLHQGFYLM DELRYVKITL TEDFFVVTVS  240
IDDDTPMLLI FGHLPRVLFK APYQRDNFIL RQTEKHELLV LVKKAQLNRH SYLKDSDFLD  300
AALDFNYLDL SALLRNSFHR YAVDVLKSGR CQMLDRRTVE MAFAYALALF AAARQEEAGT  360
EISIPRALDR QAALLQIQEF MITCLSQTPP RTTLLLYPTA VDLAKRALWT PDQITDITSL  420
VRLVYILSKQ NQQHLIPQWA LRQIADFALQ LHKTHLASFL SAFARQELYL MGSLVHSMLV  480
HTTERREIFI VETGLCSLAE LSHFTQLLAH PHHEYLSDLY TPCSSSGRRD HSLERLTRLF  540
PDATVPATVP AALSILSTMQ PSTLETFPDL FCLPLGESFS ALTVSEHVSY VVTNQYLIKG  600
ISYPVSTTVV GQSLIITQTD SQTKCELTRN MHTTHSITAA LNISLENCAF CQSALLEYDD  660
TQGVINIMYM HDSDDVLFAL DPYNEVVVSS PRTHYLMLLK NGTVLEVTDV VVDATDSRLL  720
MMSVYALSAI IGIYLLYRML KTC                                          743

SEQ ID NO: 18          moltype = AA  length = 278
FEATURE                Location/Qualifiers
source                 1..278
                       mol_type = protein
                       note = Human cytomegalovirus
                       organism = unidentified
SEQUENCE: 18
MCRRPDCGFS FSPGPVILLW CCLLLPIVSS AAVSVAPTAA EKVPAECPEL TRRCLLGEVF  60
EGDKYESWLR PLVNVTGRDG PLSQLIRYRP VTPEAANSVL LDEAFLDTLA LLYNNPDQLR  120
ALLTLLSSDT APRWMTVMRG YSECGDGSPA VYTCVDDLCR GYDLTRLSYG RSIFTEHVLG  180
FELVPPSLFN VVVAIRNEAT RTNRAVRLPV STAAAPEGIT LFYGLYNAVK EFCLRHQLDP  240
PLLRHLDKYY AGLPPELKQT RVNLPAHSRY GPQAVDAR                          278

SEQ ID NO: 19          moltype = AA  length = 906
FEATURE                Location/Qualifiers
source                 1..906
                       mol_type = protein
                       note = Human cytomegalovirus
                       organism = unidentified
SEQUENCE: 19
MESRIWCLVV CVNLCIVCLG AAVSSSSTSH ATSSTHNGSH TSRTTSAQTR SVYSQHVTSS  60
EAVSHRANET IYNTTLKYGD VVGVNTTKYP YRVCSMAQGT DLIRFERNII CTSMKPINED  120
LDEGIMVVYK RNIVAHTFKV RVYQKVLTFR RSYAYIYTTY LLGSNTEYVA PPMWEIHHIN  180
KFAQCYSSYS RVIGGTVFVA YHRDSYENKT MQLIPDDYSN THSTRYVTVK DQWHSRGSTW  240
LYRETCNLNC MLTITTARSK YPYHFFATST GDVVYISPFY NGTNRNASYF GENADKFFIF  300
```

```
PNYTIVSDFG RPNAAPETHR LVAFLERADS VISWDIQDEK NVTCQLTFWE ASERTIRSEA  360
EDSYHFSSAK MTATFLSKKQ EVNMSDSALD CVRDEAINKL QQIFNTSYNQ TYEKYGNVSV  420
FETSGGLVVF WQGIKQKSLV ELERLANRSS LNITHRTRRS TSDNNTTHLS SMESVHNLVY  480
AQLQFTYDTL RGYINRALAQ IAEAWCVDQR RTLEVFKELS KINPSAILSA IYNKPIAARF  540
MGDVLGLASC VTINQTSVKV LRDMNVKESP GRCYSRPVVI FNFANSSYVQ YGQLGEDNEI  600
LLGNHRTEEC QLPSLKIFIA GNSAYEYVDY LFKRMIDLSS ISTVDSMIAL DIDPLENTDF  660
RVLELYSQKE LRSSNVFDLE EIMREFNSYK QRVKYVEDKV VDPLPPYLKG LDDLMSGLGA  720
AGKAVGVAIG AVGGAVASVV EGVATFLKNP FGAFTIILVA IAVVIITYLI YTRQRRLCTQ  780
PLQNLFPYLV SADGTTVTSG STKDTSLQAP PSYEESVYNS GRKGPGPPSS DASTAAPPYT  840
NEQAYQMLLA LARLDAEQRA QQNGTDSLDG QTGTQDKGQK PNLLDRLRHR KNGYRHLKDS  900
DEEENV                                                            906

SEQ ID NO: 20          moltype = AA  length = 138
FEATURE                Location/Qualifiers
source                 1..138
                       mol_type = protein
                       note = Human cytomegalovirus
                       organism = unidentified
SEQUENCE: 20
MEWNTLVLGL LVLSVVAESS GNNSSTSTSA TTSKSSASVS TTKLTTVATT SATTTTTTTL  60
STTSTKLSST THDPNVMRRH ANDDFYKAHC TSHMYELSLS SFAAWWTMLN ALILMGAFCI  120
VLRHCCFQNF TATTTKGY                                               138

SEQ ID NO: 21          moltype = AA  length = 372
FEATURE                Location/Qualifiers
source                 1..372
                       mol_type = protein
                       note = Human cytomegalovirus
                       organism = unidentified
SEQUENCE: 21
MAPSHVDKVN TRTWSASIVF MVLTFVNVSV HLVLSNFPHL GYPCVYYHVV DFERLNMSAY  60
NVMHLHTPML FLDSVQLVCY AVFMQLVFLA VTIYYLVCWI KISMRKDKGM SLNQSTRDIS  120
YMGDSLTAFL FILSMDTFQL FTLTMSFRLP SMIAFMAAVH FFCLTIFNVS MVTQYRSYKR  180
SLFFFSRLHP KLKGTVQFRT LIVNLVEVAL GFNTTVVAMA LCYGFGNNFF VRTGHMVLAV  240
FVVYAIISII YFLLIEAVFF QYVKVQFGYH LGAFFGLCGL IYPIVQYDTF LSNEYRTGIS  300
WSFGMLFFIW AMFTTCRAVR YFRGRGSGSV KYQALATASG EEVAVLSHHD SLESRRLREE  360
EDDDDDEDFE DA                                                     372

SEQ ID NO: 22          moltype = AA  length = 466
FEATURE                Location/Qualifiers
source                 1..466
                       mol_type = protein
                       note = Human cytomegalovirus
                       organism = unidentified
SEQUENCE: 22
MGRKEMMVRD VPKMVFLISI SFLLVSFINC KVMSKALYNR PWRGLVLSKI GKYKLDQLKL  60
EILRQLETTI STKYNVSKQP VKNLTMNMTE FPQYYILAGP IQNYSITYLW FDFYSTQLRK  120
PAKYVYSQYN HTAKTITFRP PPCGTVPSMT CLSEMLNVSK RNDTGEQGCG NFTTFNPMFF  180
NVPRWNTKLY VGPTKVNVDS QTIYFLGLTA LLLRYAQRNC THSFYLVNAM SRNLFRVPKY  240
INGTKLKNTM RKLKRKQAPV KEQFEKKAKK TQSTTTPYFS YTTSAALNVT TNVTYSITTA  300
ARRVSTSTIA YRPDSSFMKS IMATQLRDLA TWVYTTLRYR QNPFCEPSRN RTAVSEFMKN  360
THVLIRNETP YTIYGTLDMS SLYYNETMFV ENKTASDSNK TTPTSPSMGF QRTFIDPLWD  420
YLDSLLFLDE IRNFSLRSPT YVNLTPPEHR RAVNLSTLNS LWWWLQ                  466

SEQ ID NO: 23          moltype = AA  length = 171
FEATURE                Location/Qualifiers
source                 1..171
                       mol_type = protein
                       note = Human cytomegalovirus
                       organism = unidentified
SEQUENCE: 23
MSPKNLTPFL TALWLLLGHS RVPRVRAEEC CEFINVNHPP ERCYDFKMCN RFTVALRCPD  60
GEVCYSPEKT AEIRGIVTTM THSLTRQVVH NKLTSCNYNP LYLEADGRIR CGKVNDKAQY  120
LLGAAGSVPY RWINLEYDKI TRIVGLDQYL ESVKKHKRLD VCRAKMGYML Q            171

SEQ ID NO: 24          moltype = AA  length = 214
FEATURE                Location/Qualifiers
source                 1..214
                       mol_type = protein
                       note = Human cytomegalovirus
                       organism = unidentified
SEQUENCE: 24
MLRLLLRHYF HCLLLCAVWA TPCLASSWST LTANQNPSPP WSKLTYSKPH DAATFYCPFL  60
YPSPPRSPSQ FSGFQRVSTG PECRNETLYL LYNREGQTLV ERSSTWVKKV IWYLSGRNQT  120
ILQRMPRTAS KPSDGNVQIS VEDAKIFGAH MVPKQTKLLR FVVNDGTRYQ MCVMKLESWA  180
HVFRDYSVSF QVRLTFTEAN NQTYTFCTHP NLIV                               214

SEQ ID NO: 25          moltype = AA  length = 129
FEATURE                Location/Qualifiers
```

```
source                  1..129
                        mol_type = protein
                        note = Human cytomegalovirus
                        organism = unidentified
SEQUENCE: 25
MRLCRVWLSV CLCAVVLGQC QRETAEKNDY YRVPHYWDAC SRALPDQTRY KYVEQLVDLT  60
LNYHYDASHG LDNFDVLKRI NVTEVSLLIS DFRRQNRRGG TNKRTTFNAA GSLAPHARSL  120
EFSVRLFAN                                                          129

SEQ ID NO: 26           moltype = AA  length = 694
FEATURE                 Location/Qualifiers
source                  1..694
                        mol_type = protein
                        note = Human herpes virus 6a
                        organism = unidentified
SEQUENCE: 26
MLLRLWVFVL LTPCYGWRPL NISNSSHCRN GNFENPIVRP GFITFNFYTK NDTRIYQVPK  60
CLLGSDITYH LFDAINTTES LTNYEKRVTR FYEPPMNDIL RLSPVPSVKQ FNLDRSIQPQ  120
VVYSLNMYPS QGIYYVRVVE VRQMQYDNVS CKLPNSLKEL IFPVQVRCAK ITRYVGEDIY  180
THFFTPDFMI LYIQNPAGDL TMMYGNTTSI NFKAPYKKSS FIFKQTLTDD LLLIVEKDVI  240
DVQYRFISDA TFVDETLNDV DEVEALLLKF NNLGIQTLLR GDCKKPNYAG IPQMMFLYGI  300
VHFSYSTKNT GPMPVLRVLK THENLLSIDS FVNRCVNVSE GTLQYPKMKE FLKYEPSDYS  360
YITKNKSISV STLLTYLATA YESNVTISKY KWTDIANTLQ NIYEKHMFFT NLTFSDRETL  420
FMLAEIANII PTDERMQRHM QLLIGNLCNP VEIVSWARML TADRAPNLEN IYSPCASPVR  480
RDVTNSFLKT VLTYASLDRY RSDMMEMLSV YRPPNMERVA AIQCLSPSEP AASLTLPNVT  540
FVISPSYVIK GVSLTITTTI VATSIIITAI PLNSTCVSTN YKYAGQDLLV LRNISSQTCE  600
FCQSVVMEYD DIDGPLQYIY IKNIDELKTL TDPNNNLLVP NTRTHYLLLA KNGSVFEMSE  660
VGIDIDQVSI ILVIIYILIA IIALFGLYRL IRLC                              694

SEQ ID NO: 27           moltype = AA  length = 694
FEATURE                 Location/Qualifiers
source                  1..694
                        mol_type = protein
                        note = Human herpes virus 6b
                        organism = unidentified
SEQUENCE: 27
MLFRLWVFVL LTPCYSWRPW TISDESHCKN GNSENPIVRP GFITFNFYTK NDTRIYQVPK  60
CLLGSDITYH LFDAINTTES LTNYEKRVTR FYEPPMNDIL RLSTVPAVKQ FNLDHSIQPQ  120
IVYSLNLYPS HGIYYIRVVE VRQMQYDNVS CKLPNSLNEL IFPVQVRCAK ITRYAGENIY  180
THFFTPDFMI LYIQNPAGDL TMMYGNTTDI NFKAPYRKSS FIFKQTLTDD LLLIVEKDVV  240
DEEYRFISDA TFVDETLDDV DEVEALLLKF NNLGIQTLLR GDCKKPDYAG IPQMMFLYGI  300
VHFSYSTKNT GPMPVLRVLK THENLLSIDS FVNRCVNVSE GTIQYPKMKE FLKYEPSDYS  360
YITKNKSIPV STLLTYLATA YETNVTISRY KWSDIANTLQ KIYEKHMFFT NLTFSDRETL  420
FMLAEIANFI PADERMQRHM QLLIGNLCNP VEIVSWAHML TADKAPNLEN IYSPCASPVR  480
RDVTNSFVKT VLTYASLDRY RSDMMEMLSV YRPPDMARVA AIQCLSPSEP AASLPLPNVT  540
FVISPSYVIK GVSLTITTTI VATSIIITAI PLNSTCVSTN YKYAGQDLLV LRNISSQTCE  600
FCQSVVMEYD DIDGPLQYIY IKNIDELKTL TDPNNNLLVP NTRTHYLLLA KNGSVFEMSE  660
VGIDIDQVSI ILVIIYVLIA IIALFGLYRL IRLC                              694

SEQ ID NO: 28           moltype = AA  length = 250
FEATURE                 Location/Qualifiers
source                  1..250
                        mol_type = protein
                        note = Human herpes virus 6a
                        organism = unidentified
SEQUENCE: 28
MELLLFVMSL ILLTFSKAIP LFNHNSFYFE KLDDCIAAVI NCTKSEVPLL LEPIYQPPAY  60
NEDVMSILLQ PPTKKKPFSR IMVTDEFLSD FLLLQDNPEQ LRTLFALIRD PESRDNWLNF  120
FNGFQTCSPS VGITTCIRDN CRKYSPEKIT YVNNFFVDNI AGLEFNISEN TDSFYSNIGF  180
LLYLENPAKG VTKIIRFPFN SLTLFDTILN CLKYFHLKTG VELDLLKHME TYNSKLPFRS  240
SRPTILIRNT                                                         250

SEQ ID NO: 29           moltype = AA  length = 250
FEATURE                 Location/Qualifiers
source                  1..250
                        mol_type = protein
                        note = Human herpes virus 6b
                        organism = unidentified
SEQUENCE: 29
MELLLFVMSL ILLTFSKAMP LFDHNSFYFE KLDDCIAAVI NCTRSEVPLL LEPIYQPPVY  60
NEDVMSILLK PPTKKKPFSR IMVTNEFLSD FLLLQDNPEQ LRTLFALIGD PESRDNWLNF  120
FNGFQTCSPS VGITTCISDN CRKYLPERIT YVNNFFVDNI AGLEFNISEN TDSFYSNIGF  180
LLYLENPATG ITKIIRFPFN SLTLFDTILN CLKYFHLKTG VEFDLLKQME AYNSKLPFRS  240
SRPTILIRNT                                                         250

SEQ ID NO: 30           moltype = AA  length = 830
FEATURE                 Location/Qualifiers
source                  1..830
                        mol_type = protein
```

```
                        note = Human herpes virus 6a
                        organism = unidentified
SEQUENCE: 30
MSKMAVLFLA VFLMNSVLMI YCDPDHYIRA GYNHKYPFRI CSIAKGTDLM RFDRDISCSP  60
YKSNAKMSEG FFIIYKTNIE TYTFPVRTYK KELTFQSSYR DVGVVYFLDR TVMGLAMPVY  120
EANLVNSHAQ CYSAVAMKRP DGTVFSAFHE DNNKNNTLNL FPLNFKSITN KRFITTKEPY  180
FARGPLWLYS TSTSLNCIVT EATAKAKYPF SYFALTTGEI VEGSPFFNGS NGKHFAEPLE  240
KLTILENYTM IEDLMNGMNG ATTLVRKIAF LEKADTLFSW EIKEENESVC MLKHWTTVTH  300
GLRAETNETY HFISKELTAA FVAPKESLNL TDPKQTCIKN EFEKIINEVY MSDYNDTYSM  360
NGSYQIFKTT GDLILIWQPL VQKSLMFLEQ GSEKIRRRRD VGDVKSRHDI LYVQLQYLYD  420
TLKDYINDAL GNLAESWCLD QKRTITMLHE LSKISPSSIV SEVYGRPISA QLHGDVLAIS  480
KCIEVNQSSV QLHKSMRVVD AKGVRSETMC YNRPLVTFSF VNSTPEVVPG QLGLDNEILL  540
GDHRTEECEI PSTKIFLSGN HAHVYTDYTH TNSTPIEDIE VLDAFIRLKI DPLENADFKV  600
LDLYSPDELS RANVFDLENI LREYNSYKSA LYTIEAKIAT NTPSYVNGIN SFLQGLGAIG  660
TGLGSVISVT AGALGDIVGG VVSFLKNPFG GGLMLILAIV VVVIIIVVFV RQRHVLSKPI  720
DMMFPYATNP VTTVSSVTGT TVVKTPSVKD VDGGTSVAVS EKEEGMADVS GQVSDDEYSQ  780
EDALKMLKAI KSLDESYRRK PSSSESHASK PSLIDRIRYR GYKSVNVEEA             830

SEQ ID NO: 31           moltype = AA  length = 830
FEATURE                 Location/Qualifiers
source                  1..830
                        mol_type = protein
                        note = Human herpes virus 7
                        organism = unidentified
SEQUENCE: 31
MSKMRVLFLA VFLMNSVLMI YCDSDDYIRA GYNHKYPFRI CSIAKGTDLM RFDRDISCSP  60
YKSNAKMSEG FFIIYKTNIE TYTFPVRTYK NELTFPTSYR DVGVVYFLDR TVMGLAMPVY  120
EANLVNSRAQ CYSAVAIKRP DGTVFSAYHE DNNKNETLEL FPLNFKSVTN KRFITTKEPY  180
FARGPLWLYS TSTSLNCIVT EATAKAKYPF SYFALTTGEI VEGSPFFDGS NGKHFAEPLE  240
KLTILENYTM IEDLMNGMNG ATTLVRKIAF LEKGDTLFSW EIKEENESVC MLKHWTTVTH  300
GLRAETDETY HFISKELTAA FVASKESLNL TDPKQTCIKN EFEKIITDVY MSDYNDAYSM  360
NGSYQIFKTT GDLILIWQPL VQKSLMVLEQ GSVNLRRRRD LVDVKSRHDI LYVQLQYLYD  420
TLKDYINDAL GNLAESWCLD QKRTITMLHE LSKISPSSIV SEVYGRPISA QLHGDVLAIS  480
KCIEVNQSSV QLYKSMRVVD AKGVRSETMC YNRPLVTFSF VNSTPEVVLG QLGLDNEILL  540
GDHRTEECEI PSTKIFLSGN HAHVYTDYTH TNSTPIEDIE VLDAFIRLKI DPLENADFKL  600
LDLYSPDELS RANVFDLENI LREYNSYKSA LYTIEAKIAT NTPSYVNGIN SFLQGLGAIG  660
TGLGSVISVT AGALGDIVGG VVSFLKNPFG GGLMLILAIV VVVIIIVVFV RQKHVLSKPI  720
DMMFPYATNP VTTVSSVTGT TVVKTPSVKD ADGGTSVAVS EKEEGMADVS GQISGDEYSQ  780
EDALKMLKAI KSLDESYRRK PSSSESHASK PSLIDRIRYR GYKSVNVEEA             830

SEQ ID NO: 32           moltype = AA  length = 690
FEATURE                 Location/Qualifiers
source                  1..690
                        mol_type = protein
                        note = Human herpes virus 7
                        organism = unidentified
SEQUENCE: 32
MYFYINSLLL IVSINGWKHW NILNSSICVN EKTNQTIIQP GLITFNFHDY NETRVYQIPK  60
CLFGYTFVSN LFDSVNFDES FDQYKHRITR FFNPSTEKAV KIYAQKFQTN IKPVSHTKTI  120
TVSFLPLFYE KDVYFANVSE IRKLYYNQYI CTLSNGLTDY LFPITERCVM RHYNYLNTVF  180
MLALTPSFFI ISVETGMDDV VFIFGNVSRI FFKAPFRKSS FIYRQTVSDD LLLITKKTTI  240
ERFYPFLKID FLDDIWKQNY DISFLIAKFN KLATVYIMEG FCGKPVNKDT FHLMFLFGLT  300
HFLYSTRGDG LLPLLEILNT HQSIITMGRF LEKCFKMTKS HLLYPEMEKL QNFQLVDYSY  360
ITSDLTIPIS AKLAFLSLAD GRIVTVPQNK WKEIENNIET LYEKHKLFTN LTQPERANLF  420
LLSEIGNSLV FQEKIKRKIH VLLASLCNPL EMYFWTHMLD NVMDIETMFS PCATATRKDL  480
TQRVVNNILS YKNLDAYTNK VMNTLSVYRK KRLDMFKSIS CVSNEQAAFL TLPNITYTIS  540
SKYILAGTSF SVTSTVISTT IIITVVPLNS TCTPTNYKYS VKNIKPIYNI SSHDCVFCES  600
LVVEYDDIDG IIQFVYIMDD KQLLKLIDPD TNFIDVNPRT HYLLFLRNGS VFEITALDLK  660
SSQVSIMLVL LYLIIIIIVL FGIYHVFRLF                                   690

SEQ ID NO: 33           moltype = AA  length = 246
FEATURE                 Location/Qualifiers
source                  1..246
                        mol_type = protein
                        note = Human herpes virus 7
                        organism = unidentified
SEQUENCE: 33
MKTNIFFIFL ISILNQIYAL FNNSYYSNLE QECIKNILNC TQSKTLSLLE PIDQAPIPKS  60
DIISRLLYHT PYISRRDQVL IDEDFLETFY LLYNNPNQLH TLLSLIKDSE SGHNWLGFLN  120
NFERCLSDNT LLTCRDNVCK SYSYEKLKFT GNIFVENIIG FEFNIPSNMI NFNMSILIYL  180
ENEETRTQRI VRIDHHGINV FDALLNCLRY FSRYYNFSFP LIQEMEKYNE VLPFRSEFSN  240
LLIRTY                                                             246

SEQ ID NO: 34           moltype = AA  length = 822
FEATURE                 Location/Qualifiers
source                  1..822
                        mol_type = protein
                        note = Human herpes virus 7
                        organism = unidentified
```

```
SEQUENCE: 34
MKILFLSVFI TFSLQLSLQT EADFVMTGHN QHLPFRICSI ATGTDLVRFD REVSCASYGS  60
NIKTTEGILI IYKTKIEAHT FSVRTFKKEL TFQTTYRDVG TVYFLDRTVT TLPMPIEEVH  120
MVNTEARCLS SISVKRSEEE EYVAYHKDEY VNKTLDLIPL NFKSDTVRRY ITTKEPFLRN  180
GPLWFYSTST SINCIVTDCI AKTKYPFDFF ALSTGETVEG SPFYNGINSK TFNEPTEKIL  240
FRNNYTMLKT FDDGSKGNFV TLTKMAFLEK GNTIFSWEVQ NEESSICLLK HWMTIPHALR  300
AENANSFHFI AQELTASFVT GKSNYTLSDS KYNCINSNYT SILDEIYQTQ YNNSHDKNGS  360
YEIFKTEGDL ILIWQPLIQR KLTVLENFSN ASRKRRKREL ETNKDIVYVQ LQYLYDTLKD  420
YINTALGKLA EAWCLNQKRT ITVLHELSKI SPSGIISAVY GKPMSAKLIG DVLAVSKCIE  480
VNQTSVQLHK SMRLTKDSSY DALRCYSRPL LTYSFANSSK ETYLGQLGLD NEILLGNHRT  540
EECEQSNTKI FLSGKFAHIF KDYTYVNSSL ITEIEALDAF VDLNIDPLEN ADFTLLELYT  600
KDELSKANVF DLETILREYN SYKSALHHIE TKIATVTPTY IGGIDTFFKG LGALGLGLGA  660
VLGVTAGALG DVVNGVFSFL KNPFGGALTI LLTLGVIGLV IFLFLRHKRL AQTPIDILFP  720
YTSKSTNSVL QATQSVQAQV KEPLDSSPPY LKTNKDTEPQ GDDITHTNEY SQVEALKMLK  780
AIKLLDESYK KAEIAEAKKS QRPSLLERIQ YRGYQKLSTE EL                    822

SEQ ID NO: 35          moltype = AA  length = 841
FEATURE                Location/Qualifiers
source                 1..841
                       mol_type = protein
                       organism = Varicella-zoster virus
SEQUENCE: 35
MFALVLAVVI LPLWTTANKS YVTPTPATRS IGHMSALLRE YSDRNMSLKL EAFYPTGFDE  60
ELIKSLHWGN DRKHVFLVIV KVNPTTHEGD VGLVIFPKYL LSPYHFKAEH RAPFPAGRFG  120
FLSHPVTPDV SFFDSSFAPY LTTQHLVAFT TFPPNPLVWH LERAETAATA ERPFGVSLLP  180
ARPTVPKNTI LEHKAHFATW DALARHTFFS AEAIITNSTL RIHVPLFGSV WPIRYWATGS  240
VLLTSDSGRV EVNIGVGFMS SLISLSSGPP IELIVVPHTV KLNAVTSDTT WFQLNPPGPD  300
PGPSYRVYLL GRGLDMNFSK HATVDICAYP EESLDYRYHL SMAHTEALRM TTKADQHDIN  360
EESYYHIAAR IATSIFALSE MGRTTEYFLL DEIVDVQYQL KFLNYILMRI GAGAHPNTIS  420
GTSDLIFADP SQLHDELSLL FGQVKPANVD YFISYDEARD QLKTAYALSR GQDHVNALSL  480
ARRVIMSIYK GLLVKQNLNA TERQALFFAS MILLNFREGL ENSSRVLDGR TTLLLMTSMC  540
TAAHATQAAL NIQEGLAYLN PSKHMFTIPN VYSPCMGSLR TDLTEEIHVM NLLSAIPTRP  600
GLNEVLHTQL DESEIFDAAF KTMMIFTTWT AKDLHILHTH VPEVFTCQDA AARNGEYVLI  660
LPAVQGHSYV ITRNKPQRGL VYSLADVDVY NPISVVYLSR DTCVSEHGVI ETVALPHPDN  720
LKECLYCGSV FLRYLTTGAI MDIIIIDSKD TERQLAAMGN STIPPFNPDM HGDDSKAVLL  780
FPNGTVVTLL GFERRQAIRM SGQYLGASLG GAFLAVVGFG IIGWMLCGNS RLREYNKIPL  840
T                                                                 841

SEQ ID NO: 36          moltype = AA  length = 159
FEATURE                Location/Qualifiers
source                 1..159
                       mol_type = protein
                       organism = Varicella-zoster virus
SEQUENCE: 36
MASHKWLLQI VFLKTITIAY CLHLQDDTPL FFGAKPLSDV SLIITEPCVS SVYEAWDYAA  60
PPVSNLSEAL SGIVVKTKCP VPEVILWFKD KQMAYWTNPY VTLKGLAQSV GEEHKSGDIR  120
DALLDALSGV WVDSTPSSTN IPENGCVWGA DRLFQRVCQ                         159

SEQ ID NO: 37          moltype = AA  length = 931
FEATURE                Location/Qualifiers
source                 1..931
                       mol_type = protein
                       organism = Varicella-zoster virus
SEQUENCE: 37
MSPCGYYSKW RNRDRPEYRR NLRFRRFFSS IHPNAAAGSG FNGPGVFITS VTGVWLCFLC  60
IFSMFVTAVV SVSPSSFYES LQVEPTQSED ITRSAHLGDG DEIREAIHKS QDAETKPTFY  120
VCPPPTGSTI VRLEPTRTCP DYHLGKNFTE GIAVVYKENI AAYKFKATVY YKDVIVSTAW  180
AGSSYTQITN RYADRVPIPV SEITDTIDKF GKCSSKATYV RNNHKVEAFN EDKNPQDMPL  240
IASKYNSVGS KAWHTTNDTY MVAGTPGTYR TGTSVNCIIE EVEARSIFPY DSFGLSTGDI  300
IYMSPFFGLR DGAYREHSNY AMDRFHQFEG YRQRDLDTRA LLEPAARNFL VTPHLTVGWN  360
WKPKRTEVCS LVKWREVEDV VRDEYAHNFR FTMKTLSTTF ISETNEFNLN QIHLSQCVKE  420
EARAIINRIY TTRYNSSHVR TGDIQTYLAR GGFVVVFQPL LSNSLARLYL QELVRENTNH  480
SPQKHPTRNT RSRRSVPVEL RANRTITTTS SVEFAMLQFT YDHIQEHVNE MLARISSSWC  540
QLQNRERALW SGLFPINPSA LASTILDQRV KARILGDVIS VSNCPELGSD TRIILQNSMR  600
VSGSTTRCYS RPLISIVSLN GSGTVEGQLG TDNELIMSRD LLEPCVANHK RYFLFGHHYV  660
YYEDYRYVRE IAVHDVGMIS TYVDLNLTLL KDREFMPLQV YTRDELRDTG LLDYSEIQRR  720
NQMHSLRFYD IDKVVQYDSG TAIMQGMAQF FQGLGTAGQA VGHVVLGATG ALLSTVHGFT  780
TFLSNPFGAL AVGLLVLAGL VAAFFAYRYV LKLKTSPMKA LYPLTTKGLK QLPEGMDPFA  840
EKPNATDTPI EEIGDSQNTE PSVNSGFDPD KFREAQEMIK YMTLVSAAER QESKARKKNK  900
TSALLTSRLT GLALRNRRGY SRVRTENVTG V                                 931

SEQ ID NO: 38          moltype = AA  length = 354
FEATURE                Location/Qualifiers
source                 1..354
                       mol_type = protein
                       organism = Varicella-zoster virus
SEQUENCE: 38
MFLIQCLISA VIFYIQVTNA LIFKGDHVSL QVNSSLTSIL IPMQNDNYTE IKGQLVFIGE  60
QLPTGTNYSG TLELLYADTV AFCFRSVQVI RYDGCPRIRT SAFISCRYKH SWHYGNSTDR  120
```

```
ISTEPDAGVM LKITKPGIND AGVYVLLVRL DHSRSTDGFI LGVNVYTAGS HHNIHGVIYT  180
SPSLQNGYST RALFQQARLC DLPATPKGSG TSLFQHMLDL RAGKSLEDNP WLHEDVVTTE  240
TKSVVKEGIE NHVYPTDMST LPEKSLNDPP ENLLIIIPIV ASVMILTAMV IVIVISVKRR  300
RIKKHPIYRP NTKTRRGIQN ATPESDVMLE AAIAQLATIR EESPPHSVVN PFVK        354

SEQ ID NO: 39          moltype = AA  length = 560
FEATURE                Location/Qualifiers
source                 1..560
                       mol_type = protein
                       organism = Varicella-zoster virus
SEQUENCE: 39
MKRIQINLIL TIACIQLSTE SQPTPVSITE LYTSAATRKP DPAVAPTSAA SRKPDPAVAP  60
TSAASRKPDP AVAPTSAASR KPDPAVAPTS AATRKPDPAV APTSAASRKP DPAVAPTSAA  120
TRKPDPAVAP TSAASRKPDP AANTQHSQPP FLYENIQCVH GGIQSIPYFH TFIMPCYMRL  180
TTGQQAAFKQ QQKTYEQYSL DPEGSNITRW KSLIRPDLHI EVWFTRHLID PHRQLGNALI  240
RMPDLPVMLY SNSADLNLIN NPEIFTHAKE NYVIPDVKTT SDFSVTILSM DATTEGTYIW  300
RVVNTKTKNV ISEHSITVTT YYRPNITVVG DPVLTGQTYA AYCNVSKYYP PHSVRVRWTS  360
RFGNIGKNFI TDAIQEYANG LFSYVSAVRI PQQKQMDYPP PAIQCNVLWI RDGVSNMKYS  420
AVVTPDVYPF PNVSIGIIDG HIVCTAKCVP RGVVHFVWWV NDSPINHENS EITGVCDQNK  480
RFVNMQSSCP TSELDGPITY SCHLDGYPKK FPPFSAVYTY DASTYATTFS VVAVIIGVIS  540
ILGTLGLIAV IATLCIRCCS                                               560

SEQ ID NO: 40          moltype = AA  length = 623
FEATURE                Location/Qualifiers
source                 1..623
                       mol_type = protein
                       organism = Varicella-zoster virus
SEQUENCE: 40
MGTVNKPVVG VLMGFGIITG TLRITNPVRA SVLRYDDFHT DEDKLDTNSV YEPYYHSDHA  60
ESSWVNRGES SRKAYDHNSP YIWPRNDYDG FLENAHEHHG VYNQGRGIDS GERLMQPTQM  120
SAQEDLGDDT GIHVIPTLNG DDRHKIVNVD QRQYGDVFKG DLNPKPQGQR LIEVSVEENH  180
PFTLRAPIQR IYGVRYTETW SFLPSLTCTG DAAPAIQHIC LKHTTCFQDV VVDVDCAENT  240
KEDQLAEISY RFQGKKEADQ PWIVVNTSTL FDELELDPPE IEPGVLKVLR TEKQYLGVYI  300
WNMRGSDGTS TYATFLVTWK GDEKTRNPTP AVTPQPRGAE FHMWNYHSHV FSVGDTFSLA  360
MHLQYKIHEA PFDLLLEWLY VPIDPTCQPM RLYSTCLYHP NAPQCLSHMN SGCTFTSPHL  420
AQRVASTVYQ NCEHADNYTA YCLGISHMEP SFGLILHDGG TTLKFVDTPE SLSGLYVFVV  480
YFNGHVEAVA YTVVSTVDHF VNAIEERGFP PTAGQPPATT KPKEITPVNP GTSPLLRYAA  540
WTGGLAAVVL LCLVIFLICT AKRMRVKAYR VDKSPYNQSM YYAGLPVDDF EDSESTDTEE  600
EFGNAIGGSH GGSSYTVYID KTR                                           623

SEQ ID NO: 41          moltype = AA  length = 838
FEATURE                Location/Qualifiers
source                 1..838
                       mol_type = protein
                       organism = Herpes simplex virus 1
SEQUENCE: 41
MGNGLWFVGV IILGAAWGQV HDWTEQTDPW FLDGLGMDRM YWRDTNTGRL WLPNTPDPQK  60
PPRGFLAPPD ELNLTTASLP LLRWYEERFC FVLVTTAEFP RDPGQLLYIP KTYLLGRPPN  120
ASLPAPTTVE PTAQPPPAVA PLKGLLHNPT ASVLLRSRAW VTFSAVPDPE ALTFPRGDNV  180
ATASHPSGPR DTPPPRPPVG ARRHPTTELD ITHLHNASTT WLATRGLLRS PGRYVYFSPS  240
ASTWPVGIWT TGELVLGCDA ALVRARYGRE FMGLVISMHD SPPAEVMVVP AGQTLDRVGD  300
PADENPPGAL PGPPGGPRYR VFVLGSLTRA DNGSALDALR RVGGYPEEGT NYAQFLSRAY  360
AEFFSGDAGA EQGPRPPLFW RLTGLLATSG FAFVNAAHAN GAVCLSDLLG FLAHSRALAG  420
LAARGAAGCA ADSVFFNVSV LDPTARLQLE ARLQHLVAEI LEREQSLALH ALGYQLAFVL  480
DSPSAYDAVA PSAAHLIDAL YAEFLGGRVV TTPVVHRALF YASAVLRQPF LAGVPSAVQR  540
ERARRSLLIA SALCTSDVAA ATNADLRTAL ARADHQKTLF WLPDHFSPCA ASLRFDLDES  600
VFILDALAQA TRSETPVEVL AQQTHGLAST LTRWAHYNAL IRAFVPEASH RCGGQSANVE  660
PRILVPITHN ASYVVTHSPL PRGIGYKLTG VDVRRPLFLT YLTATCEGST RDIESKRLVR  720
TQNQRDLGLV GAVFMRYTPA GEVMSVLLVD TDNTQQQIAA GPTEGAPSVF SSDVPSTALL  780
LFPNGTVIHL LAFDTQPVAA IAPGFLAASA LGVVMITAAL AGILKVLRTS VPFFWRRE    838

SEQ ID NO: 42          moltype = AA  length = 224
FEATURE                Location/Qualifiers
source                 1..224
                       mol_type = protein
                       organism = Herpes simplex virus 1
SEQUENCE: 42
MGILGWVGLI AVGVLCVRGG LPSTEYVIRS RVAREVGDIL KVPCVPLPSD DLDWRYETPS  60
AINYALIDGI FLRYHCPGLD TVLWDRHAQK AYWVNPFLFV AGFLEDLSYP AFPANTQETE  120
TRLALYKEIR QALDSRKQAA SHTPVKAGCV NFDYSRTRRC VGRQDLGPTN GTSGRTPVLP  180
PDDEAGLQPK PLTTPPPIIA TSDPTPRRDA ATKSRRRRPH SRRL                    224

SEQ ID NO: 43          moltype = AA  length = 904
FEATURE                Location/Qualifiers
source                 1..904
                       mol_type = protein
                       organism = Herpes simplex virus 1
SEQUENCE: 43
MHQGAPSWGR RWFVVWALLG LTLGVLVASA APTSPGTPGV AAATQAANGG PATPAPPPLG  60
```

```
AAPTGDPKPK KNKKPKNPTP PRPAGDNATV AAGHATLREH LRDIKAENTD ANFYVCPPPT  120
GATVVQFEQP RRCPTRPEGQ NYTEGIAVVF KENIAPYKFK ATMYYKDVTV SQVWFGHRYS  180
QFMGIFEDRA PVPFEEVIDK INAKGVCRST AKYVRNNLET TAFHRDDHET DMELKPANAA  240
TRTSRGWHTT DLKYNPSRVE AFHRYGTTVN CIVEEVDARS VYPYDEFVLA TGDFVYMSPF  300
YGYREGSHTE HTTYAADRFK QVDGFYARDL TTKARATAPT TRNLLTTPKF TVAWDWVPKR  360
PSVCTMTKWQ EVDEMLRSEY GGSFRFSSDA ISTTFTTNLT EYPLSRVDLG DCIGKDARDA  420
MDRIFARRYN ATHIKVGQPQ YYQANGGFLI AYQPLLSNTL AELYVREHLR EQSRKPPNPT  480
PPPPGASANA SVERIKTTSS IEFARLQFTY NHIQRHVNDM LGRVAIAWCE LQNHELTLWN  540
EARKLNPNAI ASVTVGRRVS ARMLGDVMAV STCVPVAADN VIVQNSMRIS SRPGACYSRP  600
LVSFRYEDQG PLVEGQLGEN NELRLTRDAI EPCTVGHRRY FTFGGGYVYF EEYAYSHQLS  660
RADITTVSTF IDLNITMLED HEFVPLEVYT RHEIKDSGLL DYTEVQRRNQ LHDLRFADID  720
TVIHADANAA MFAGLGAFFE GMGDLGRAVG KVVMGIVGGV VSAVSGVSSF MSNPFGALAV  780
GLLVLAGLAA AFFAFRYVMR LQSNPMKALY PLTTKELKNP TNPDASGEGE EGGDFDEAKL  840
AEAREMIRYM ALVSAMERTE HKAKKKGTSA LLSAKVTDMV MRKRRNTNYT QVPNKDGDAD  900
EDDL                                                               904

SEQ ID NO: 44          moltype = AA  length = 394
FEATURE                Location/Qualifiers
source                 1..394
                       mol_type = protein
                       organism = Herpes simplex virus 1
SEQUENCE: 44
MGGAAARLGA VILFVVIVGL HGVRGKYALA DASLKMADPN RFRGKDLPVP DRLTDPPGVR  60
RVYHIQAGLP DPFQPPSLPI TVYYAVLERA CRSVLLNAPS EAPQIVRGGS EDVRKQPYNL  120
TIAWFRMGGN CAIPITVMEY TECSYNKSLG ACPIRTQPRW NYYDSFSAVS EDNLGFLMHA  180
PAFETAGTYL RLVKINDWTE ITQFILEHRA KGSCKYALPL RIPPSACLSP QAYQQGVTVD  240
SIGMLPRFIP ENQRIVAVYS LKIAGWHGPK APYTSTLLPP ELSETPNATQ PELAPEDPED  300
SALLEDPVGT VAPQIPPNWH IPSIQDAATP YHPPATPNNM GLIAGAVGGS LLAALVICGI  360
VYWMRRRTQK GPKRIRLPHI REDDQPSSHQ PLFY                              394

SEQ ID NO: 45          moltype = AA  length = 838
FEATURE                Location/Qualifiers
source                 1..838
                       mol_type = protein
                       organism = Herpes simplex virus 2
SEQUENCE: 45
MGPGLWVVMG VLVGVAGGHD TYWTEQIDPW FLHGLGLART YWRDTNTGRL WLPNTPDASD  60
PQRGRLAPPG ELNLTTASVP MLRWYAERFC FVLVTTAEFP RDPGQLLYIP KTYLLGRPRN  120
ASLPELPEAG PTSRPPAEVT QLKGLSHNPG ASALLRSRAW VTFAAAPDRE GLTFPRGDDG  180
ATERHPDGRR NAPPPGPPAG APRHPTTNLS IAHLHNASVT WLAARGLLRT PGRYVYLSPS  240
ASTWPVGVWT TGGLAFGCDA ALVRARYGKG FMGLVISMRD SPPAEIIVVP ADKTLARVGN  300
PTDENAPAVL PGPPAGPRYR VFVLGAPTPA DNGSALDALR RVAGYPEEST NYAQYMSRAY  360
AEFLGEDPGS GTDARPSLFW RLAGLLASSG FAFINAAHAH DAIRLSDLLG FLAHSRVLAG  420
LAARGAAGCA ADSVFLNVSV LDPAARLRLE ARLGHLVAAI LEREQSLAAH ALGYQLAFVL  480
DSPAAYGAVA PSAARLIDAL YAEFLGGRAL TAPMVRRALF YATAVLRAPF LAGAPSAEQR  540
ERARRGLLIT TALCTSDVAA ATHADLRAAL ARTDHQKNLF WLPDHFSPCA ASLRFDLAEG  600
GFILDALAMA TRSDIPADVM AQQTRGVASA LTRWAHYNAL IRAFVPEATH QCSGPSHNAE  660
PRILVPITHN ASYVVTHTPL PRGIGYKLTG VDVRRPLFIT YLTATCEGHA REIEPKRLVR  720
TENRRDLGLV GAVFLRYTPA GEVMSVLLVD TDATQQQLAQ GPVAGTPNVF SSDVPSVALL  780
LFPNGTVIHL LAFDTLPIAT IAPGFLAASA LGVVMITAAL AGILRVVRTC VPFLWRRE    838

SEQ ID NO: 46          moltype = AA  length = 516
FEATURE                Location/Qualifiers
source                 1..516
                       mol_type = protein
                       organism = Herpes simplex virus 2
SEQUENCE: 46
MGFVCLFGLV VMGAWGAWGG SQATEYVLRS VIAKEVGDIL RVPCMRTPAD DVSWRYEAPS  60
VIDYARIDGI FLRYHCPGLD TFLWDRHAQR AYLVNPFLFA AGFLEDLSHS VFPADTQETT  120
TRRALYKEIR DALGSRKQAV SHAPVRAGCV NFDYSRTRRC VGRRDLRPAN TTSTWEPPVS  180
SDDEASSQSK PLATQPPVLA LSNAPHGGSP RREVGAGILA SDATSHVCIA SHPGSGAGQP  240
TRLAAGSAVQ RRRPRGCPPG VMFSASTTPE QPLGLSGDAT PPLPTSVPLD WAAFRRAFLI  300
DDAWRPLLEP ELANPLTARL LAEYDRRCQT EEVLPPREDV FSWTRYCTPD DVRVVIIGQD  360
PYHHPGQAHG LAFSVRADVP VPPSLRNVLA AVKNCYPDAR MSGRGCLEKW ARDGVLLLNT  420
TLTVKRGAAA SHSKLGWDRF VGGVVRRLAA RRPGLVFMLW GAHAQNAIRP DPRQHYVLKF  480
SHPSPLSKVP FGTCQHFLAA NRYLETRDIM PIDWSV                            516

SEQ ID NO: 47          moltype = AA  length = 904
FEATURE                Location/Qualifiers
source                 1..904
                       mol_type = protein
                       organism = Herpes simplex virus 2
SEQUENCE: 47
MRGGGLICAL VVGALVAAVA SAAPAAPAAP RASGGVAATV AANGGPASRP PPVPSPATTK  60
ARKRKTKKPP KRPEATPPPD ANATVAAGHA TLRAHLREIK VENADAQFYV CPPPTGATVV  120
QFEQPRRCPT RPEGQNYTEG IAVVFKENIA PYKFKATMYY KDVTVSQVWF GHRYSQFMGI  180
FEDRAPVPFE EVIDKINTKG VCRSTAKYVR NNMETTAFHR DDHETDMELK PAKVATRTSR  240
GWHTTDLKYN PSRVEAFHRY GTTVNCIVEE VDARSVYPYD EFVLATGDFV YMSPFYGYRE  300
GSHTEHTSYA ADRFKQVDGF YARDLTTKAR ATSPTTRNLL TTPKFTVAWD WVPKRPAVCT  360
```

```
MTKWQEVDEM LRAEYGGSFR FSSDAISTTF TTNLTEYSLS RVDLGDCIGR DAREAIDRMF  420
ARKYNATHIK VGQPQYYLAT GGFLIAYQPL LSNTLAELYV REYMREQDRK PRNATPAPLR  480
EAPSANASVE RIKTTSSIEF ARLQFTYNHI QRHVNDMLGR IAVAWCELQN HELTLWNEAR  540
KLNPNAIASA TVGRRVSARM LGDVMAVSTC VPVAPDNVIV QNSMRVSSRP GTCYSRPLVS  600
FRYEDQGPLI EGQLGENNEL RLTRDALEPC TVGHRRYFIF GGGYVYFEEY AYSHQLSRAD  660
VTTVSTFIDL NITMLEDHEF VPLEVYTRHE IKDSGLLDYT EVQRRNQLHD LRFADIDTVI  720
RADANAAMFA GLCAFFEGMG DLGRAVGKVV MGVVGGVVSA VSGVSSFMSN PFGALAVGLL  780
VLAGLVAAFF AFRYVLQLQR NPMKALYPLT TKELKTSDPG GVGGEGEEGA EGGGFDEAKL  840
AEAREMIRYM ALVSAMERTE HKARKKGTSA LLSSKVTNMV LRKRNKARYS PLHNEDEAGD  900
EDEL                                                              904

SEQ ID NO: 48          moltype = AA  length = 393
FEATURE                Location/Qualifiers
source                 1..393
                       mol_type = protein
                       organism = Herpes simplex virus 2
SEQUENCE: 48
MGRLTSGVGT AALLVVAVGL RVVCAKYALA DPSLKMADPN RFRGKNLPVL DRLTDPPGVK  60
RVYHIQPSLE DPFQPPSIPI TVYYAVLERA CRSVLLHAPS EAPQIVRGAS DEARKHTYNL  120
TIAWYRMGDN CAIPITVMEY TECPYNKSLG VCPIRTQPRW SYYDSFSAVS EDNLGFLMHA  180
PAFETAGTYL RLVKINDWTE ITQFILEHRA RASCKYALPL RIPPAACLTS KAYQQGVTVD  240
SIGMLPRFIP ENQRTVALYS LKIAGWHGPK PPYTSTLLPP ELSDTTNATQ PELVPEDPED  300
SALLEDPAGT VSSQIPPNWH IPSIQDVAPH HAPAAPSNPG LIIGALAGST LAVLVIGGIA  360
FWVRRRAQMA PKRLRLPHIR DDDAPPSHQP LFY                               393

SEQ ID NO: 49          moltype = AA  length = 6
FEATURE                Location/Qualifiers
source                 1..6
                       mol_type = protein
                       organism = synthetic construct
SEQUENCE: 49
HHHHHH                                                            6

SEQ ID NO: 50          moltype = AA  length = 5
FEATURE                Location/Qualifiers
source                 1..5
                       mol_type = protein
                       organism = synthetic construct
SEQUENCE: 50
RRRRD                                                             5

SEQ ID NO: 51          moltype = DNA  length = 22
FEATURE                Location/Qualifiers
source                 1..22
                       mol_type = other DNA
                       organism = synthetic construct
SEQUENCE: 51
tcgtcgttgt cgttttgtcg tt                                          22

SEQ ID NO: 52          moltype = DNA  length = 12
FEATURE                Location/Qualifiers
source                 1..12
                       mol_type = other DNA
                       organism = synthetic construct
SEQUENCE: 52
tcataacgtt cc                                                     12

SEQ ID NO: 53          moltype = AA  length = 5
FEATURE                Location/Qualifiers
source                 1..5
                       mol_type = protein
                       note = Human cytomegalovirus
                       organism = unidentified
SEQUENCE: 53
RTKRS                                                             5

SEQ ID NO: 54          moltype = DNA  length = 30
FEATURE                Location/Qualifiers
source                 1..30
                       mol_type = other DNA
                       organism = synthetic construct
SEQUENCE: 54
aaaaaaaaaa aaaacgttaa aaaaaaaaaa                                  30
```

-continued

```
SEQ ID NO: 55          moltype = AA  length = 6
FEATURE                Location/Qualifiers
source                 1..6
                       mol_type = protein
                       organism = synthetic construct
SEQUENCE: 55
RRRRRD                                                         6
```

What is claimed is:

1. An antigenic composition comprising the following polypeptides:

a first recombinant fusion protein comprising human cytomegalovirus (HCMV) glycoprotein L (gL) polypeptide and an HCMV glycoprotein H (gH) polypeptide comprising an extracellular domain, wherein the first recombinant fusion protein is a monomeric HCMV gL/g H heterodimer in which the HCMV gL polypeptide and the HCMV gH polypeptide are covalently joined by a first flexible linker;

a second recombinant fusion protein comprising an HCMV unique long 128 (UL128) polypeptide, an HCMV unique long 130 (UL130) polypeptide and an HCMV unique long 131A (UL131A) polypeptide, wherein the second recombinant fusion protein is a monomeric HCMV UL128/UL130/UL131A in which the HCMV UL128 polypeptide is covalently joined to the HCMV UL130 polypeptide through a second flexible linker and the HCMV UL130 polypeptide is covalently joined to the HCMV UL131A polypeptide through a third flexible linker; and a trimeric HCMV glycoprotein B (gB) in native conformation, wherein the HCMV gB comprises an extracellular domain, wherein a furin recognition site in the HCMV gB is replaced by a fourth flexible linker sequence that allows the trimeric HCMV gB to adopt its native conformation.

2. The antigen composition of claim 1, wherein the first, second, third, or fourth flexible linker sequence comprises glycine and serine amino acids and has a length of 10-25 amino acids.

3. A composition of nucleic acids, comprising:

a first nucleic acid encoding a first recombinant fusion protein comprising a human cytomegalovirus (HMCV) glycoprotein L (gL) polypeptide and an HMCV glycoprotein (gH) polypeptide comprising an extracellular domain, wherein the fusion protein is a monomeric HCMV gL/gH heterodimer in which the HCMV gL polypeptide and the HCMV gH polypeptide are covalently joined by a first flexible linker;

a second nucleic acid encoding a second recombinant fusion protein comprising an HCMV unique long 128 (UL128) polypeptide, an HCMV unique long 130 (UL130) polypeptide and an HCMV unique long 131A (UL131A) polypeptide, wherein the second recombinant fusion protein is a monomeric HCMV UL128/UL130/UL131A in which the HCMV UL128 polypeptide is covalently joined to the HCMV UL130 polypeptide through a second flexible linker and the HCMV UL130 polypeptide is covalently joined to the HCMV UL131A polypeptide through a third flexible linker; and a third nucleic acid encoding an HCMV glycoprotein B (gB), wherein the HCMV gB comprises an extracellular domain and forms a trimeric gB in native conformation when expressed in a host cell, wherein a furin recognition site in the encoded HCMV gB is replaced by a fourth flexible linker sequence that allows the trimeric HCMV gB to adopt its native conformation when expressed in the host cell.

4. A method for inhibiting or treating an HCMV infection in a subject, comprising administering a therapeutically effective amount of the antigenic composition of claim 1 to a subject.

5. The antigenic composition of claim 2, wherein the first, second, third, or fourth flexible linker sequence comprises the amino acid sequence of SEQ ID NO: 3.

6. An antigenic composition comprising:

a recombinant fusion protein comprising a human cytomegalovirus (HCMV) glycoprotein L (gL) polypeptide and an HCMV glycoprotein H (gH) polypeptide comprising an extracellular domain, wherein the recombinant fusion protein is a monomeric HCMV gL/gH heterodimer in which the HCMV gL polypeptide and the HCMV gH polypeptide are covalently joined by a first flexible linker; and a trimeric HCMV glycoprotein B (gB) in native conformation, wherein the HCMV gB comprises an extracellular domain, wherein a furin recognition site in the HCMV gB is replaced by a second flexible linker sequence that allows the trimeric HCMV gB to adopt its native conformation.

7. The antigenic composition of claim 6, wherein the first or second flexible linker sequence comprises glycine and serine amino acids and has a length of 10-25 amino acids.

8. The antigenic composition of claim 7, wherein the first or second flexible linker sequence comprises the amino acid sequence of SEQ ID NO: 3.

9. The antigenic composition of claim 6, wherein:

the HCMV gB comprises amino acids 23-750 of the amino acid sequence of SEQ ID NO: 19, except that amino acids 457 to 461 are replaced by the second flexible linker sequence; and the HCMV gL polypeptide comprises amino acids 31-278 of the amino acid sequence of SEQ ID NO: 18, the HCMV gH polypeptide comprises amino acids 24-718 of the amino acid sequence of SEQ ID NO: 17, and the first flexible linker sequence comprises glycine and serine amino acids and has a length of 10-25 amino acids.

10. The antigenic composition of claim 9, wherein each of the first and second flexible linker sequences comprises the amino acid sequence of SEQ ID NO: 3.

11. The antigenic composition of claim 1, wherein:

the HCMV gB comprises amino acids 23-750 of the amino acid sequence of SEQ ID NO: 19, except that amino acids 457 to 461 are replaced by the fourth flexible linker sequence;

the HCMV gL polypeptide comprises amino acids 31-278 of the amino acid sequence of SEQ ID NO: 18, the HCMV gH polypeptide comprises amino acids 24-718 of the amino acid sequence of SEQ ID NO: 17, and the first flexible linker sequence comprises glycine and serine amino acids and having a length of 10-25 amino acids; and the HCMV UL128 polypeptide comprises amino acids 28-171 of the amino acid sequence of SEQ ID NO: 23; the HCMV UL130 polypeptide comprises amino acids 26-214 of the amino acid sequence of SEQ ID NO: 24; the HCMV UL131A polypeptide comprises amino acids 19-129 of the amino acid sequence of SEQ ID NO: 25; and the second and third flexible linker sequences each comprise glycine and serine amino acids and have a length of 10-25 amino acids.

12. The antigenic composition of claim 11, wherein each of the first, second, third, and fourth flexible linker sequences comprises the amino acid sequence of SEQ ID NO: 3.

13. The antigenic composition of claim 9, wherein the HCMV gL signal peptide is replaced by a Igk leader sequence.

14. The antigenic composition of claim 13, wherein the HCMV gB signal peptide is replaced by a Igk leader sequence.

15. The antigenic composition of claim 14, wherein the HCMV UL128 polypeptide signal peptide is replaced by a Igk leader sequence.

16. The antigenic composition of claim 11, wherein the HCMV gL signal peptide is replaced by a Igk leader sequence.

17. The antigenic composition of claim 16, wherein the HCMV gB signal peptide is replaced by a Igk leader sequence.

18. The antigenic composition of claim 17, wherein the HCMV UL128 polypeptide signal peptide is replaced by a Igk leader sequence.

* * * * *